United States Patent
Kim et al.

(10) Patent No.: US 11,071,735 B2
(45) Date of Patent: Jul. 27, 2021

(54) TREATMENT OF INFLAMMATORY CONDITIONS AND AUTOIMMUNE DISEASES WITH GLUCOSE UPTAKE INHIBITORS

(71) Applicant: Kadmon Corporation, LLC, New York, NY (US)

(72) Inventors: Ji-In Kim, Princeton, NJ (US); Kellen L. Olszewski, Brooklyn, NY (US); Anthony M. Barsotti, New York, NY (US); Masha V. Poyurovsky, New York, NY (US); Kevin G. Liu, West Windsor, NJ (US); Koi Morris, Plainsboro, NJ (US); Xuemei Yu, Livingston, NJ (US)

(73) Assignee: KADMON CORPORATION, LLC, New York, NY (US)

( * ) Notice: Subject to any disclaimer, the term of this patent is extended or adjusted under 35 U.S.C. 154(b) by 0 days.

(21) Appl. No.: 16/608,233

(22) PCT Filed: Apr. 27, 2018

(86) PCT No.: PCT/US2018/029880
§ 371 (c)(1),
(2) Date: Oct. 25, 2019

(87) PCT Pub. No.: WO2018/201006
PCT Pub. Date: Nov. 1, 2018

(65) Prior Publication Data
US 2020/0046702 A1 Feb. 13, 2020

Related U.S. Application Data

(60) Provisional application No. 62/513,099, filed on May 31, 2017, provisional application No. 62/491,977, filed on Apr. 28, 2017.

(51) Int. Cl.
*A61K 31/517* (2006.01)
*A61P 29/00* (2006.01)
*A61K 31/5377* (2006.01)

(52) U.S. Cl.
CPC ........ *A61K 31/517* (2013.01); *A61K 31/5377* (2013.01); *A61P 29/00* (2018.01)

(58) Field of Classification Search
CPC .................................................. A61K 31/517
See application file for complete search history.

(56) References Cited

FOREIGN PATENT DOCUMENTS

| WO | 2006/105081 A2 | 10/2006 |
| WO | 2012/040499 A2 | 3/2012 |
| WO | WO2012040499 * | 3/2012 |
| WO | 2016/210330 A1 | 12/2016 |

* cited by examiner

*Primary Examiner* — Paul V Ward
(74) *Attorney, Agent, or Firm* — Fox Rothschild LLP

(57) ABSTRACT

This invention provides methods of treating inflammatory conditions and autoimmune diseases in a mammal, comprising administering to the mammalian subject in need thereof a therapeutically effective amount of a compound, or pro-drug thereof, or pharmaceutically acceptable salt or ester of said compound or pro-drug, wherein the compound is an inhibitor of glucose uptake. In particular aspects, the present invention provides a method of treating inflammatory conditions and autoimmune diseases in a mammal, and preferably a human, in which the glucose uptake inhibitor modulates the glucose transport of GLUT1 and GLUT3.

36 Claims, 10 Drawing Sheets

A.

B.

| IC50 (nM) | Bay876 | Cytochalasin B | Example 2 | Example 13 | Example 18 | Example 3 |
|---|---|---|---|---|---|---|
| DLD1 WT | 65 | 1231 | 139.5 | 86.87 | 99.5 | 59.63 |
| DLD1 GLUT1 -/- | 4809 | 171.6 | 30.92 | 38.91 | 43.95 | 33.64 |

| IC50 (µM) | Example 2 | Example 26 | Example 13 |
|---|---|---|---|
| Proliferation | 1.70 | 0.923 | 0.678 |
| IL17 | 0.367 | 0.199 | 0.211 |
| IL2 | 0.233 | 0.190 | N/A |

A.

B.

A.

1. n.s.
2. Th17 skewing: DMSO
3. Th17 skewing: Example 2 [1 µM]

B.

1. DMSO
2. Example 2 (1 µM)
3. Bayer GLUT1/3i (5 µM)*
   *BMCL 26 (2016) 1732-1737
4. 2-DG (20 mM)
5. AICAR (2 mM)
6. Temsirolimus (1 µM)
7. Tofacitinib (1 µM)
8. Non-stimulated

TREATMENT OF INFLAMMATORY CONDITIONS AND AUTOIMMUNE DISEASES WITH GLUCOSE UPTAKE INHIBITORS

FIELD OF THE INVENTION

This invention provides methods for the treatment of inflammatory conditions and autoimmune diseases by administering compounds that modulate glucose uptake activity. Particularly, the present invention provides methods for treating inflammatory conditions and autoimmune diseases by modulators of cellular transport/uptake of glucose, and particularly GLUT1 and GLUT3, but also including but not limited to GLUT1-14 (SLC2A1-SLC2A14).

BACKGROUND OF THE INVENTION

Glucose is an essential source of energy for mammalian cells, and is also used as a substrate in protein and lipid synthesis. Glucose transporters enable the movement of glucose across the cell membrane. GLUT1 is one of several transporters that facilitate transport of glucose and/or other molecules, GLUT1 is ubiquitously expressed, however the expression of this transporter is elevated in the cells of the endothelial barriers, developing embryo and activated immune cells. GLUT3 is a facilitative glucose transporter that can also mediate the uptake of various other monosaccharides across the cell membrane including 2-deoxyglucose, galactose, mannose, xylose and fucose.

Glucose represents a central nutrient for many organisms, and control of glucose signaling and consumption is tightly regulated. Accordingly, many disease states are associated with defects in this regulation and therefore may be susceptible to therapeutic intervention using glucose uptake inhibitors. Certain glucose transporters facilitate glucose uptake by tumors, in which they are frequently overexpressed. In particular, increased GLUT1 expression has been found to provide a mechanism for increased metabolism necessary for sustained tumor growth. Similar to cancer cells, certain immune cell subsets express high levels of GLUT transporters and require increased glucose metabolism for their growth, differentiation, and effector function.

SUMMARY OF THE INVENTION

In one aspect, the invention features a method of treating inflammatory conditions and autoimmune diseases in a mammal, comprising administering to a mammalian subject in need thereof a therapeutically effective amount of a compound, or pro-drug thereof, or pharmaceutically acceptable salt or ester of said compound or pro-drug, wherein the compound is an inhibitor of glucose uptake. In particular aspects, the present invention provides a method of treating inflammatory conditions and autoimmune diseases in a mammal, and preferably a human, in which the glucose uptake inhibitor modulates the glucose transport of GLUT1 and GLUT3.

BRIEF DESCRIPTION OF THE FIGURES

FIG. 1A shows the plot of the concentration versus the % glycolysis. FIG. 1B reports the the $IC_{50}$ of glycolysis inhibition for selected compounds.

In FIG. 2A, human CD4 positive T cells were activated for 24 hours prior to a one hour treatment with the indicated glucose uptake inhibitors combined with 10 μM oligomycin. In FIG. 2B, human CD4 T cells were activated for 48 hours in the presence of the glucose uptake inhibitors. IL-17 and IL-2 secreted into the supernatant was measured by ELISA (R&D systems). Proliferation was measured by Cell Titer Glo (Promega). FIG. 2C lists the IC50 values (μM) for the glucose uptake inhibitors against activated T cell glycolysis, IL-17 secretion and proliferation.

In FIG. 3A, human CD4 positive T cells were activated for 24 hours prior to a one hour treatment with Bay876 combined with 1 μM oligomycin. In FIG. 3B, human CD4 T cells were activated for 48 hours in the presence of Bay876. L-17 secreted into the supernatant was measured by ELISA (R&D systems). Proliferation was measured by Cell Titer Glo (Promega).

In FIG. 5A, THP1 cells were activated with 1 μg/ml LPS for 16 hrs prior to a one-hour glycolysis assay (Example 2+Oligomycin). In FIG. 5B, THP1 cells were treated with Example 2 one hour prior to a 16 hour treatment with 1 μg/ml LPS, after which MCP-1 secretion into the media was measured by ELISA (R&D systems) and cell number measured by Cell Titer Glo (Promega).

FIG. 7A. CD4 T cells were activated for 48 hrs in the presence of IL-1β, TGF-β and 1 μM of the Example 2 compound. For the last 5 hrs, PMA/Ionomycin/Brefeldin A was added and intracellular staining for cytokines was performed. Flow cytometry was used to assess INFγ and IL-17A levels (gated on live cells). Quantification of percent positive cells positive is shown in FIG. 7A. FIG. 7B. Cells were cultured and treated as in FIG. 7A, excluding PMA/Ionomycin/Brefeldin A treatment. Flow cytometry was used to assess levels of CD4 T cell lineage defining transcription factors.

FIG. 8A. CD4 T cells were activated for 48 hrs in the presence of IL-1β, TGF-β and 1 μM of the Example 2 compound. Western blotting analysis was used to determine the activation status of Stat3, Stat1 and pS6K (as a marker of mTORC1 activity) and the expression of GLUT1 protein. FIG. 8B. CD4 T cells were activated for 48 hrs and treated with the indicated compounds for 1.5 or 4 hrs. Western blotting analysis was used to determine the activation status of Stat3, Stat1 and pS6K (as a marker of mTORC1 activity).

DETAILED DESCRIPTION OF THE INVENTION

Figure 1:
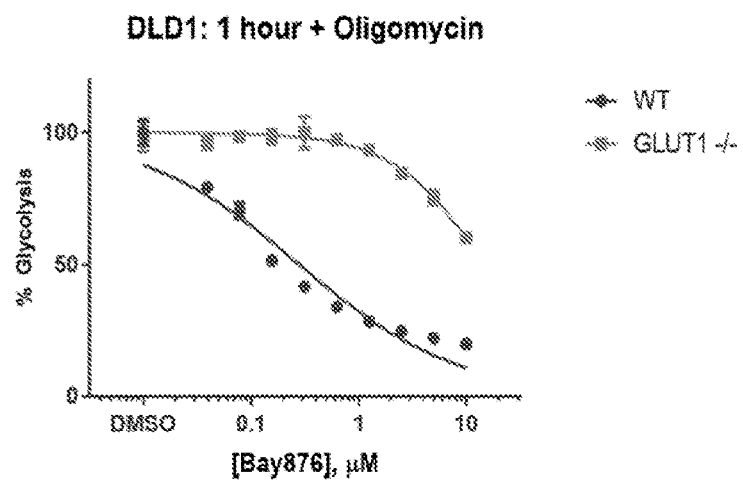
FIG. 1 shows the results from a glycolysis assay in syngeneic DLD1 cancer cells, either WT (wild-type) or GLUT1−/−. Cells were treated with GLUT inhibitors plus oligomycin and subsequently ATP levels were determined using Cell Titer Glo. The compounds disclosed herein inhibit both GLUT1 and GLUT3 while Bay876 selectively inhibits GLUT1 (A/B).
Figure 1:
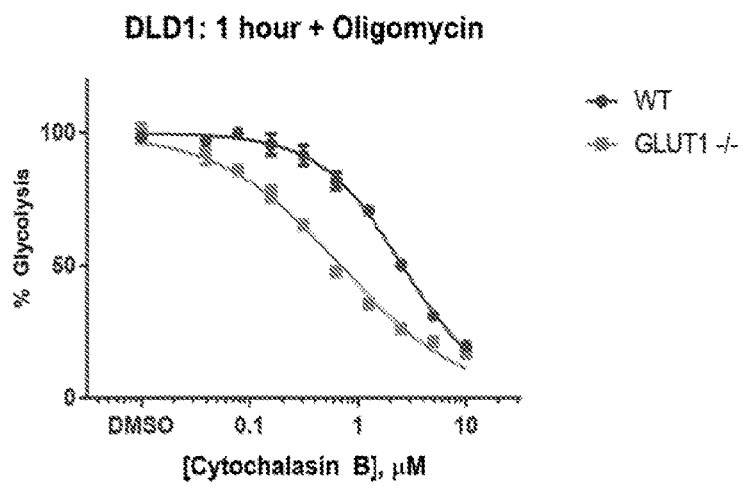
Figure 1:
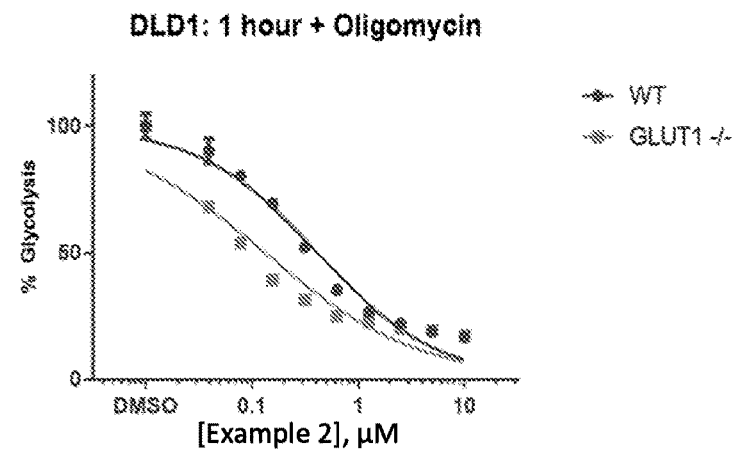

Glucose represents a central nutrient for many organisms, and control of glucose signaling and consumption is tightly regulated. Accordingly, many disease states are associated with defects in this regulation and therefore may be susceptible to therapeutic intervention using glucose uptake inhibitors. The present invention provides glucose uptake inhibitors that have utility in inflammatory conditions and autoimmunity diseases, and methods of treatment of such diseases and conditions.

The metabolism of immune cells is increasingly being recognized as major regulator of immune cell fate and function. The field of immunometabolism has made great insights into the precise metabolic pathways utilized by various immune cell subsets that allows for therapeutic intervention to control immune cell activity. Central to the activity of most pro-inflammatory immune cell subsets is glucose metabolism. Similar to cancer cells, certain activated immune cells adopt the process of "aerobic glycolysis." While normal cells maintain a low rate of glycolysis, followed by full oxidization of pyruvate in the mitochondria, the pro-inflammatory immune cells rely on an increased rate of glycolysis followed by lactic acid fermentation (even in the presence of oxygen). Since mitochondrial oxidative phosphorylation generates more ATP than glycolysis alone, activated pro-inflammatory cells rely heavily on increased rates of glucose consumption.

For example, activated T effector cells (both CD4 and CD8 positive T cells) switch to the process of aerobic glycolysis to meet their energetic demands (MacIver, N. J., R. D. Michalek, and J. C. Rathmell, Metabolic regulation of T lymphocytes. Annu Rev Immunol, 2013. 31: p. 259-83.) Since hyper-activation of helper T-cells (e.g. Th17, Th2, Th1) plays a large role in autoimmune disorders and inflammatory conditions, decreasing the rate of glycolysis in these cells would be predicted to curb secretion of inflammatory cytokines. In addition, as inhibition of glucose uptake activates AMPK, a master regulator of T regulatory cells (Michalek, R. D., et al., Cutting edge: distinct glycolytic and lipid oxidative metabolic programs are essential for effector and regulatory CD4+ T cell subsets. J Immunol, 2011. 186(6): p. 3299-303)), the use of glucose uptake inhibitors would also be predicted to increase the T regulatory cell population (which suppress inflammation), thereby "rebalancing" the immune system. In addition to CD4+ T cells, other cells of the immune system (including but not limited to CD8+ T cells, Gamma-Delta T cells, B cells, innate lymphoid cells, monocytes, macrophages, dendritic cells, neutrophils) rely heavily on glycolysis for their development, activation and effector functions. It has now been found that the glucose uptake inhibitors as described herein have utility as immunosuppressants and provide benefit in many autoimmune diseases and inflammatory conditions.

As cellular metabolism is highly adaptable in general, targeting the transport of glucose is the most reliable way to disrupt glucose metabolism of activated pro-inflammatory immune cells.

Activated T cells are known to upregulate GLUT1 upon activation and this has been shown to be essential for pro-inflammatory effector T cell function. For example, mouse GLUT1 KO CD4+ T cells are unable to differentiate (in vitro or in vivo) into Th1, Th2 or Th17 cells, but can still differentiate into T regulatory cells (anti-inflammatory). In addition, mouse GLUT1 KO CD4+ T cells are unable to cause disease pathology in mouse models of GVHD and Colitis (Cell Metab. 2014 Jul. 1; 20(1):61-72). Interestingly, additional GLUT transporters are also expressed in activated T cells, including but not limited to GLUT3 (Cell Metab. 2014 Jul. 1; 20(1):61-72).

Accordingly, we have investigated the use of inhibitors of GLUT transporters against activated pro-inflammatory immune cells, including but not limited to activated human CD4+ T cells. In order to understand what GLUT transporters are required to sustain glycolysis in activated T cells, we first utilized the syngeneic cancer cell lines DLD1 WT and DLD GLUT1−/− that rely on GLUT1 and GLUT3 expression, respectively, for glucose transport. Within this system, we have identified small molecules that simultaneously have the property of inhibiting both GLUT1 and GLUT3 mediated glucose transport. In addition, we have confirmed the GLUT1-selective nature of a published small molecule inhibitor of GLUT1 (Chem Med Chem. 2016 Oct. 19; 11(20):2261-2271).

Using these compounds, we have found that the inhibition of GLUT1 alone is not sufficient to substantially decrease glycolysis in activated human CD4+ T cells (as measured by glycolytically-derived ATP levels). Rather, small molecule inhibitors that are also able to antagonize GLUT3 function did significantly reduce glycolysis in activated human CD4+ T cells. In addition, a GLUT1 selective inhibitor failed to suppress IL-17 secretion of human CD4+ T cells skewed toward the Th17 lineage, whereas inhibitors of GLUT1/3 substantially abrogated IL-17 secretion. Therefore, we have demonstrated that the suppression of both glycolysis and function of activated human CD4+ T cells by targeting glucose transport requires inhibition of GLUT3. In addition, we have shown that inhibitors of GLUT1/3 suppress glycolysis and selectively abrogate functions of activated THP1 monocytes, suggesting that small molecule inhibitors of glucose transport will effect of the function of not only activated T cells, but also pro-inflammatory innate immune cells.

Compounds for use in the methods of the invention include small molecules. As used herein, the terms "chemical agent" and "small molecule" are used interchangeably, and both terms refer to substances that have a molecular weight up to about 4000 atomic mass units (Daltons), preferably up to about 2000 Daltons, and more preferably up to about 1000 Daltons. Unless otherwise stated herein, the term "small molecule" as used herein refers exclusively to chemical agents, and does not refer to biological agents. As used herein, "biological agents" are molecules which include proteins, polypeptides, and nucleic acids, and have molecular weights equal to or greater than about 2000 atomic mass units (Daltons). Compounds of the invention include salts, esters, and other pharmaceutically acceptable forms of such compounds.

Compounds useful according to the methods of the present invention include those having the formula I:

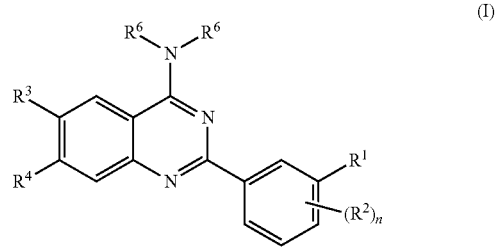

(I)

wherein:
$R^1$ is selected from the group consisting of aryl, —$(CH_2)_y$—$NR^{13}R^{14}$, —X—$R^{12}$, —$(CH_2)_y$—C(=O) $NR^{13}R^{14}$, —O—$(CH_2)_y$—$CO_2R^{12}$, —O—$(CH_2)_y$—C (=O)NR$^{13}$R$^{14}$, —O—(CH$_2$)$_y$-cycloalkyl, —(CH$_2$)$_y$—O—C(=O)—NR$^{13}$R$^{14}$, —NH—C(=O)—(CH$_2$)$_y$—NR$^{13}$R$^{14}$, —NH—C(=O)—X—R$^{15}$, —(CH$_2$)$_y$—S(=O)$_2$NR$^{13}$R$^{14}$, —O—(CH$_2$)$_y$—S(=O)$_2$NR$^{13}$R$^{14}$, —NH—S(=O)$_2$—X—R$^{15}$, —NH—(CH$_2$)$_y$—NR$^{13}$R$^{14}$, —O—(CH$_2$)$_y$-heteroaryl, —O—C(=O)—(CH$_2$)$_y$—NR$^{13}$R$^{14}$, and —O—(CH$_2$)$_z$—NR$^{13}$R$^{14}$;

R$^{12}$ is selected from the group consisting of C$_1$-C$_{10}$ alkyl, —(C$_1$-C$_6$ alkyl)-O—(C$_1$-C$_6$ alkyl), —(C$_1$-C$_6$ alkyl)-C(=O)NR$^{16}$R$^{17}$, —(C$_1$-C$_6$ alkyl)-O—(C$_1$-C$_6$ alkyl)-O—(C$_1$-C$_6$ alkyl), —(C$_1$-C$_6$ alkyl)-NR$^{16}$R$^{17}$, aryl, —(C$_1$-C$_6$ alkyl)-O-(aryl), aralkyl, C$_3$-C$_7$ cycloalkyl, a three to twelve membered heterocyclic ring containing up to 3 heteroatoms, each of which may be optionally substituted at one or more carbon atoms by from 1 to 3 substituents independently selected from halo, C$_1$-C$_6$ alkyl, C$_1$-C$_6$ alkoxy, hydroxy, cyano, and C$_1$-C$_3$ perfluoro alkyl;

R$^{13}$ and R$^{14}$ are independently selected from the group consisting of H, C$_1$-C$_8$ alkyl, C$_2$-C$_8$ alkenyl, C$_2$-C$_8$ alkynyl, —(C$_1$-C$_6$ alkyl)-O—(C$_1$-C$_6$ alkyl), —(C$_1$-C$_6$ alkyl)-C(=O)NR$^{16}$R$^{17}$, —(C$_1$-C$_6$ alkyl)-NR$^{16}$R$^{17}$, aryl, aralkyl, heteroaryl, C$_3$-C$_7$ cycloalkyl, a three to twelve membered heterocyclic ring containing up to 3 heteroatoms, each of which may be optionally substituted by from 1 to 3 substituents independently selected from halo, C$_1$-C$_6$ alkyl, C$_2$-C$_6$ alkenyl, C$_3$-C$_7$ cycloalkyl, C$_1$-C$_6$ alkoxy, —SO$_2$-alkyl, hydroxy, amino, cyano and C$_1$-C$_3$ perfluoro alkyl;

or R$^{13}$ and R$^{14}$ may be taken together to form a three to twelve membered heterocyclic ring having up to 3 heteroatoms which is optionally substituted by from 1 to 3 substituents independently selected from halo, C$_1$-C$_6$ alkyl, C$_2$-C$_6$ alkenyl, C$_1$-C$_6$ alkoxy, C$_3$-C$_7$ cycloalkyl, —SO$_2$-alkyl, oxo, hydroxy, cyano and C$_1$-C$_3$ perfluoro alkyl;

X is selected from a covalent bond, O, and C$_1$-C$_6$ alkyl;

R$^{15}$ is selected from the group consisting of H, C$_1$-C$_8$ alkyl, aryl, heteroaryl, C$_3$-C$_7$ cycloalkyl, —(C$_1$-C$_6$ alkyl)-O—(C$_1$-C$_6$ alkyl), —(C$_1$-C$_6$ alkyl)-O-(aryl), —(C$_1$-C$_6$ alkyl)-C(=O)NR$^{16}$R$^{17}$, —O—(CH$_2$)$_x$—CO$_2$R$^{18}$, —O—(CH$_2$)$_x$—C(=O)NR$^{16}$R$^{17}$, —(C$_1$-C$_6$ alkyl)-CO$_2$R$^{18}$, and a three to twelve membered heterocyclic ring containing up to 3 heteroatoms, each of which may be optionally substituted by from 1 to 3 substituents independently selected from halo, C$_1$-C$_6$ alkyl, C$_2$-C$_6$ alkenyl, C$_1$-C$_6$ alkoxy, hydroxy, cyano and C$_1$-C$_3$ perfluoro alkyl;

R$^{16}$ and R$^{17}$ are independently selected from the group consisting of H, C$_1$-C$_8$ alkyl, C$_2$-C$_8$ alkenyl, C$_2$-C$_8$ alkynyl, —(C$_1$-C$_6$ alkyl)-O—(C$_1$-C$_6$ alkyl), aryl, aralkyl, heteroaryl, C$_3$-C$_7$ cycloalkyl, a three to twelve membered heterocyclic ring containing up to 3 heteroatoms, each of which may be optionally substituted by from 1 to 3 substituents independently selected from halo, C$_1$-C$_6$ alkyl, C$_2$-C$_6$ alkenyl, C$_1$-C$_6$ alkoxy, hydroxy, cyano and C$_1$-C$_3$ perfluoro alkyl;

or R$^{16}$ and R$^{17}$ may be taken together to form a three to twelve membered heterocyclic ring having up to 3 heteroatoms which is optionally substituted by from 1 to 3 substituents independently selected from halo, C$_1$-C$_6$ alkyl, C$_2$-C$_6$ alkenyl, C$_1$-C$_6$ alkoxy, oxo, hydroxy, cyano and C$_1$-C$_3$ perfluoro alkyl;

R$^{18}$ is selected from the group consisting of aryl, aralkyl, heteroaryl, C$_1$-C$_6$ alkyl, —(C$_1$-C$_6$ alkyl)-O—(C$_1$-C$_6$ alkyl), —(C$_1$-C$_6$ alkyl)-NR$^{16}$R$^{17}$, —(C$_1$-C$_6$ alkyl)-O—(C$_1$-C$_6$ alkyl)-O—(C$_1$-C$_6$ alkyl), each of which may be optionally substituted by from 1 to 3 substituents independently selected from halo, C$_1$-C$_6$ alkoxy, hydroxy, cyano and C$_1$-C$_3$ perfluoroalkyl;

x is selected from 1 to 6;
y is selected from 0 to 6;
z is selected from 2 to 6;

each R$^2$ is independently selected from the group consisting of lower alkyl, CN, halo, hydroxy, lower alkoxy, amino, and perfluoro lower alkyl;

n is selected from 0 to 4;

R$^3$ is selected from the group consisting of H, lower alkyl, CN, halo, hydroxy, lower alkoxy, amino, perfluoro lower alkyl, —(CH$_2$)$_a$—NR$^{33}$R$^{34}$, —Y—R$^{32}$, —O—(CH$_2$)$_a$—CO$_2$R$^{32}$, —O—(CH$_2$)$_a$—C(=O)NR$^{33}$R$^{34}$, —O—(CH$_2$)$_a$-heteroaryl, —O—(CH$_2$)$_a$-cycloalkyl, —O—C(=O)—(CH$_2$)$_a$—NR$^{33}$R$^{34}$, —O—(CH$_2$)$_c$—NR$^{33}$R$^{34}$, —NH—C(=O)—(CH$_2$)$_a$—NR$^{33}$R$^{34}$, —NH—C(=O)—Y—R$^{35}$, —NH—C(=O)—(CH$_2$)$_a$—NR$^{33}$R$^{34}$;

R$^{32}$ is selected from the group consisting of C$_1$-C$_6$ alkyl, —(C$_1$-C$_6$ alkyl)-O—(C$_1$-C$_6$ alkyl), —(C$_1$-C$_6$ alkyl)-NR$^{36}$R$^{37}$, —(C$_1$-C$_6$ alkyl)-C(=O)NR$^{36}$R$^{37}$, —(C$_1$-C$_6$ alkyl)-O—(C$_1$-C$_6$ alkyl)-O—(C$_1$-C$_6$ alkyl), each of which may be optionally substituted at one or more carbon atoms by from 1 to 3 substituents independently selected from halo, C$_1$-C$_6$ alkoxy, hydroxy, amino, cyano and C$_1$-C$_3$ perfluoro alkyl;

R$^{33}$ and R$^{34}$ are independently selected from the group consisting of H, C$_1$-C$_8$ alkyl, C$_2$-C$_8$ alkenyl, C$_2$-C$_8$ alkynyl, —(C$_1$-C$_6$ alkyl)-O—(C$_1$-C$_6$ alkyl), —(C$_1$-C$_6$ alkyl)-NR$^{36}$R$^{37}$, —(C$_1$-C$_6$ alkyl)-C(=O)NR$^{36}$R$^{37}$, aryl, aralkyl, heteroaryl, C$_3$-C$_7$ cycloalkyl, a three to twelve membered heterocyclic ring containing up to 3 heteroatoms, each of which may be optionally substituted by from 1 to 3 substituents independently selected from halo, C$_1$-C$_6$ alkyl, C$_2$-C$_6$ alkenyl, C$_3$-C$_7$ cycloalkyl, C$_1$-C$_6$ alkoxy, hydroxy, amino, cyano and C$_1$-C$_3$ perfluoro alkyl;

or R$^{33}$ and R$^{34}$ may be taken together to form a three to twelve membered heterocyclic ring having up to 3 heteroatoms which is optionally substituted by from 1 to 3 substituents independently selected from halo, C$_1$-C$_6$ alkyl, C$_2$-C$_6$ alkenyl, C$_1$-C$_6$ alkoxy, oxo, hydroxy, amino, cyano and C$_1$-C$_3$ perfluoro alkyl;

Y is selected from a covalent bond, O, NH, and C$_1$-C$_6$ alkyl;

R$^{35}$ is selected from the group consisting of H, aryl, —(C$_1$-C$_6$ alkyl)-O—(C$_1$-C$_6$ alkyl), —(C$_1$-C$_6$ alkyl)-NR$^{36}$R$^{37}$, —CO$_2$R$^{38}$, —O—(CH$_2$)$_b$—CO$_2$R$^{38}$, and —C(=O)NR$^{36}$R$^{37}$, R$^{36}$ and R$^{37}$ are independently selected from the group consisting of H, C$_1$-C$_8$ alkyl, C$_2$-C$_8$ alkenyl, C$_2$-C$_8$ alkynyl, —(C$_1$-C$_6$ alkyl)-O—(C$_1$-C$_6$ alkyl), aryl, aralkyl, heteroaryl, C$_3$-C$_7$ cycloalkyl, a three to twelve membered heterocyclic ring containing up to 3 heteroatoms, each of which may be optionally substituted by from 1 to 3 substituents independently selected from halo, C$_1$-C$_6$ alkyl, C$_2$-C$_6$ alkenyl, C$_1$-C$_6$ alkoxy, hydroxy, amino, cyano and C$_1$-C$_3$ perfluoro alkyl;

or R$^{36}$ and R$^{37}$ may be taken together to form a three to twelve membered heterocyclic ring having up to 3 heteroatoms which is optionally substituted by from 1 to 3 substituents independently selected from halo, C$_1$-C$_6$ alkyl, C$_2$-C$_6$ alkenyl, C$_1$-C$_6$ alkoxy, oxo, hydroxy, amino, cyano and C$_1$-C$_3$ perfluoro alkyl;

R$^{38}$ is selected from the group consisting of H, aryl, aralkyl, heteroaryl, C$_1$-C$_6$ alkyl, —(C$_1$-C$_6$ alkyl)-O—(C$_1$-C$_6$ alkyl), —(C$_1$-C$_6$ alkyl)-NR$^{36}$R$^{37}$, —(C$_1$-C$_6$ alkyl)-O—(C$_1$-C$_6$ alkyl)-O—(C$_1$-C$_6$ alkyl), each of which may be optionally substituted by from 1 to 3 substituents independently selected from halo, C$_1$-C$_6$ alkoxy, hydroxy, amino, cyano and C$_1$-C$_3$ perfluoroalkyl;

R$^4$ is selected from the group consisting of H, lower alkyl, CN, halo, hydroxy, lower alkoxy, amino, perfluoro lower alkyl, —(CH$_2$)$_a$—NR$^{43}$R$^{44}$, —Z—R$^{42}$, —O—(CH$_2$)$_a$—CO$_2$R$^{42}$, —O—(CH$_2$)$_a$—C(=O)NR$^{43}$R$^{44}$, —O—(CH$_2$)$_a$-heteroaryl, —O—(CH$_2$)$_a$-cycloalkyl, —O—C(=O)—(CH$_2$)$_a$—NR$^{43}$R$^{44}$, —O—(CH$_2$)$_c$—NR$^{43}$R$^{44}$, —NH—C(=O)—(CH$_2$)$_a$—NR$^{43}$R$^{44}$, —NH—C(=O)—Z—R$^{45}$, —NH—C(=O)—(CH$_2$)$_a$—NR$^{43}$R$^{44}$;

R$^{42}$ is selected from the group consisting of C$_1$-C$_6$ alkyl, —(C$_1$-C$_6$ alkyl)-O—(C$_1$-C$_6$ alkyl), —(C$_1$-C$_6$ alkyl)-NR$^{46}$R$^{47}$, —(C$_1$-C$_6$ alkyl)-C(=O)NR$^{46}$R$^{47}$, —(C$_1$-C$_6$ alkyl)-O—(C$_1$-C$_6$ alkyl)-O—(C$_1$-C$_6$ alkyl), each of which may be optionally substituted at one or more carbon atoms by from 1 to 3 substituents independently selected from halo, C$_1$-C$_6$ alkoxy, hydroxy, amino, cyano and C$_1$-C$_3$ perfluoro alkyl;

R$^{43}$ and R$^{44}$ are independently selected from the group consisting of H, C$_1$-C$_8$ alkyl, C$_2$-C$_8$ alkenyl, C$_2$-C$_8$ alkynyl, —(C$_1$-C$_6$ alkyl)-O—(C$_1$-C$_6$ alkyl), —(C$_1$-C$_6$ alkyl)-NR$^{46}$R$^{47}$, —(C$_1$-C$_6$ alkyl)-C(=O)NR$^{46}$R$^{47}$, aryl, aralkyl, heteroaryl, C$_3$-C$_7$ cycloalkyl, a three to twelve membered heterocyclic ring containing up to 3 heteroatoms, each of which may be optionally substituted by from 1 to 3 substituents independently selected from halo, C$_1$-C$_6$ alkyl, C$_2$-C$_6$ alkenyl, C$_3$-C$_7$ cycloalkyl, C$_1$-C$_6$ alkoxy, hydroxy, amino, cyano and C$_1$-C$_3$ perfluoro alkyl;

or R$^{43}$ and R$^{44}$ may be taken together to form a three to twelve membered heterocyclic ring having up to 3 heteroatoms which is optionally substituted by from 1 to 3 substituents independently selected from halo, C$_1$-C$_6$ alkyl, C$_2$-C$_6$ alkenyl, C$_1$-C$_6$ alkoxy, oxo, hydroxy, amino, cyano and C$_1$-C$_3$ perfluoro alkyl;

Z is selected from a covalent bond, O, NH, and C$_1$-C$_6$ alkyl;

R$^{45}$ is selected from the group consisting of H, aryl, —(C$_1$-C$_6$ alkyl)-O—(C$_1$-C$_6$ alkyl), —(C$_1$-C$_6$ alkyl)-NR$^{46}$R$^{47}$, —CO$_2$R$^{48}$, —O—(CH$_2$)$_b$—CO$_2$R$^{48}$, and —C(=O)NR$^{46}$R$^{47}$;

R$^{46}$ and R$^{47}$ are independently selected from the group consisting of H, C$_1$-C$_8$ alkyl, C$_2$-C$_8$ alkenyl, C$_2$-C$_8$ alkynyl, —(C$_1$-C$_6$ alkyl)-O—(C$_1$-C$_6$ alkyl), aryl, aralkyl, heteroaryl, C$_3$-C$_7$ cycloalkyl, a three to twelve membered heterocyclic ring containing up to 3 heteroatoms, each of which may be optionally substituted by from 1 to 3 substituents independently selected from halo, C$_1$-C$_6$ alkyl, C$_2$-C$_6$ alkenyl, C$_1$-C$_6$ alkoxy, hydroxy, amino, cyano and C$_1$-C$_3$ perfluoro alkyl;

or R$^{46}$ and R$^{47}$ may be taken together to form a three to twelve membered heterocyclic ring having up to 3 heteroatoms which is optionally substituted by from 1 to 3 substituents independently selected from halo, C$_1$-C$_6$ alkyl, C$_2$-C$_6$ alkenyl, C$_1$-C$_6$ alkoxy, oxo, hydroxy, amino, cyano and C$_1$-C$_3$ perfluoro alkyl;

R$^{48}$ is selected from the group consisting of H, aryl, aralkyl, heteroaryl, C$_1$-C$_6$ alkyl, —(C$_1$-C$_6$ alkyl)-O—(C$_1$-C$_6$ alkyl), —(C$_1$-C$_6$ alkyl)-NR$^{46}$R$^{47}$, —(C$_1$-C$_6$ alkyl)-O—(C$_1$-C$_6$ alkyl)-O—(C$_1$-C$_6$ alkyl), each of which may be optionally substituted by from 1 to 3 substituents independently selected from halo, C$_1$-C$_6$ alkoxy, hydroxy, amino, cyano and C$_1$-C$_3$ perfluoroalkyl;

each a is independently selected from 0 to 6;
each b is independently selected from 0 to 6;
each c is independently selected from 2 to 6;
R$^5$ is selected from the group consisting of H and C$_1$-C$_6$ alkyl;
R$^6$ is selected from the group of formula (IA) and (IB):

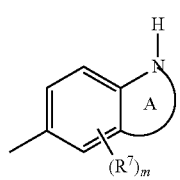

(IA)

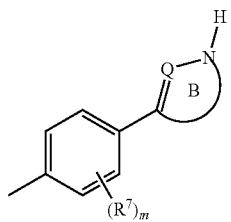

(IB)

wherein

Ring A is a 5- or 6-membered ring which may comprise 0-2 additional ring heteroatoms selected from N, O and S, and may be unsubstituted or may be substituted with 1 to 3 substituents selected from halo, CN, oxo, hydroxy, amino, lower alkyl, perfluoro lower alkyl, and lower alkoxy;

Ring B is a 5- or 6-membered ring which may comprise 0-2 additional ring heteroatoms selected from N, O and S, and may be unsubstituted or may be substituted with 1 to 3 substituents selected from halo, CN, oxo, hydroxy, amino, lower alkyl, perfluoro lower alkyl, and lower alkoxy;

R$^7$ is selected from the group consisting of halo, CN, oxo, hydroxy, amino, lower alkyl, perfluoro lower alkyl, and lower alkoxy; and m is 0 to 2.

In certain embodiments of the invention, the group of formula IA is selected from:

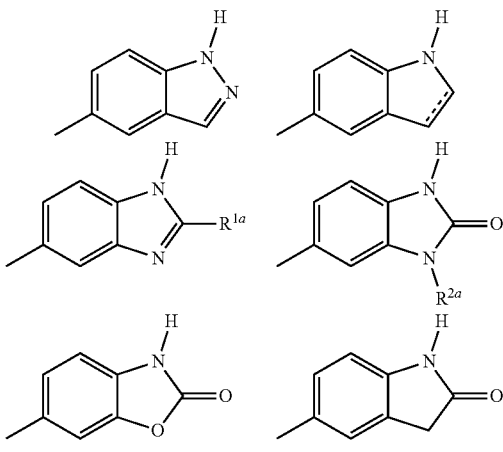

wherein the dotted line represents an optional double bond; R$^{1a}$ is selected from the group consisting of H, lower alkyl, and perfluoro lower alkyl; and R$^{2a}$ is selected from the group consisting of H and lower alkyl.

In certain embodiments of the invention, the group of formula IB is selected from:

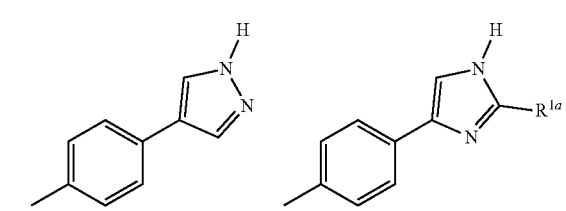

-continued

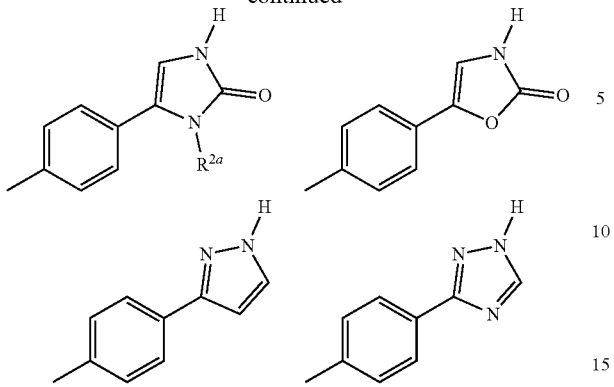

wherein R$^{1a}$ is selected from the group consisting of H, lower alkyl, and perfluoro lower alkyl; and R$^{2a}$ is selected from the group consisting of H and lower alkyl.

In a certain embodiments of the present invention, there is provided a compound of the formula II:

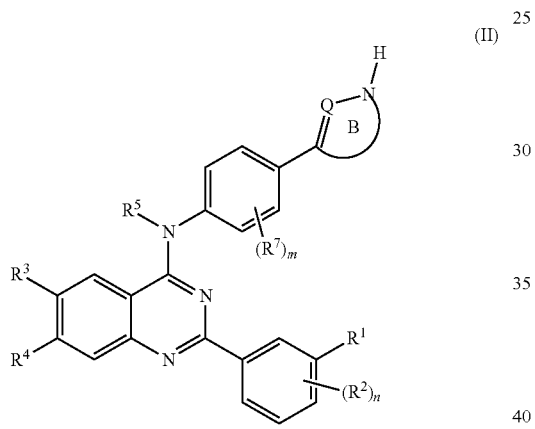

wherein R$^1$, R$^2$, R$^3$, R$^4$, R$^5$, R$^7$, Ring B, n and m are as stated above for formula I.

In a certain embodiments of the present invention, there is provided a compound of the formula III:

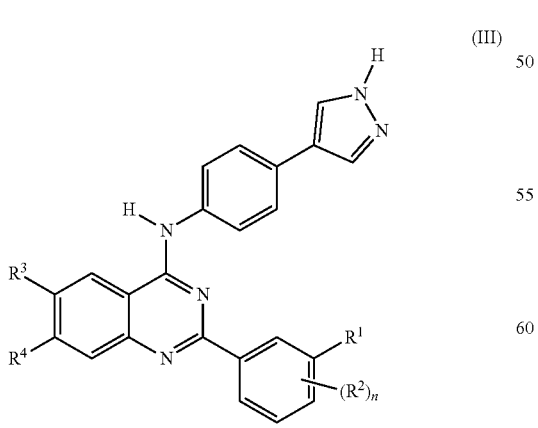

wherein R$^1$, R$^2$, R$^3$, R$^4$, n and m are as stated above for formula I.

In a certain embodiments of the present invention, there is provided a compound of the formula IV:

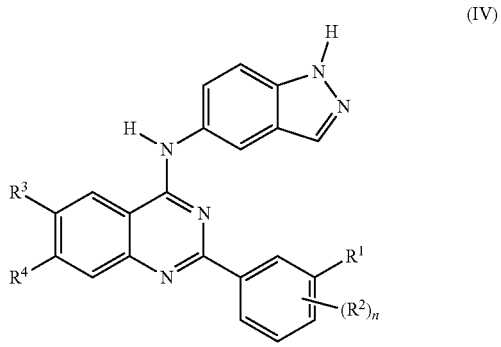

wherein R$^1$, R$^2$, R$^3$, R$^4$, n and m are as stated above for formula I.

In a certain embodiments of the present invention, there is provided a compound of the formula V:

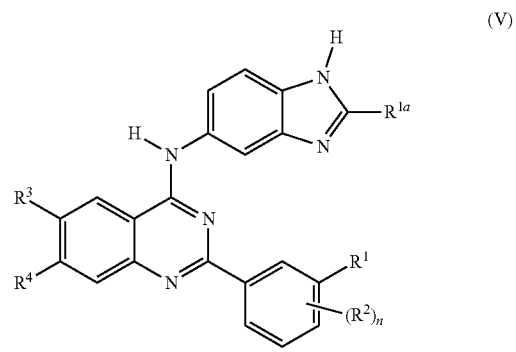

wherein R$^{1a}$ is selected from the group consisting of H, lower alkyl, and perfluoro lower alkyl; and R$^1$, R$^2$, R$^3$, R$^4$, n and m are as stated above for formula I.

In preferred embodiments of the present invention, there is provided a compound of the formula IIIa:

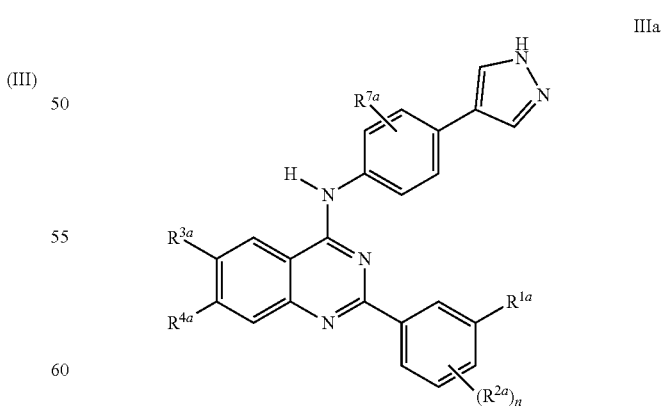

wherein:
R$^{1a}$ is selected from the group consisting of
O—(CH$_2$)$_y$—C(=O)—NR$^{13a}$R$^{14a}$ and
—NH—C(=O)—(CH$_2$)$_y$—NR$^{13a}$R$^{14a}$;

$R^{13a}$ and $R^{14a}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), each of which may be optionally substituted by from 1 to 3 substituents independently selected from halo, hydroxy, amino, cyano and $C_1$-$C_3$ perfluoro alkyl;

alternatively, $R^{13a}$ and $R^{14a}$ may be taken together to form a three to six membered heterocyclic ring having 1 to 3 heteroatoms, and which is optionally substituted by from 1 to 3 substituents independently selected from halo, $C_1$-$C_6$ alkyl, $C_2$-$C_6$ alkenyl, $C_1$-$C_6$ alkoxy, —$SO_2$-alkyl, oxo, hydroxy, cyano and $C_1$-$C_3$ perfluoro alkyl;

y is 0 to 6;

$R^{2a}$ is selected from the group consisting of H, lower alkyl, halo, lower alkoxyl, hydroxy, and perfluoro lower alkyl;

$R^{3a}$ is selected from the group consisting of H, lower alkyl, halo, hydroxy, lower alkoxy, amino, and perfluoro lower alkyl, wherein the lower alkyl and lower alkoxy may be optionally substituted by halo or lower alkoxy;

$R^{4a}$ is selected from the group consisting of H, lower alkyl, halo, hydroxy, lower alkoxy, amino, and perfluoro lower alkyl, wherein the lower alkyl and lower alkoxy may be optionally substituted by halo or lower alkoxy; and $R^{7a}$ is selected from the group consisting of H and halo.

In embodiments of the present invention, for the compound of the formula IIIa any one or more of the following selections is preferred:

y is 1 to 3, and preferably is 1;

$R^{13a}$ and $R^{14a}$ are independently selected from the group consisting of H, $C_1$-$C_8$ alkyl;

$R_{13a}$ is H;

$R_{13a}$ is H, and $R^{14a}$ is $C_1$ to $C_8$ alkyl, or $C_4$ to $C_8$ alkyl, or $C_1$ to $C_6$ alkyl, or $C_4$ to $C_6$ alkyl;

$R^{2a}$ is selected from the group consisting of H and halo;

$R^{3a}$ is selected from the group consisting of H, halo, and lower alkoxy, optionally substituted with halo or lower alkoxyl; and $R^{4a}$ is H or halo.

In preferred embodiments of for compounds of Formula IIIa, there is provided a compound of the formula IIIb:

IIIb wherein:

$R^{14b}$ is $C_1$-$C_6$ alkyl, which may be branched, straight chain or cyclic, and which is optionally substituted with 1 to 3 substituents selected from halo and hydroxy; and $R^{3b}$ is selected from the group consisting of H, halo, and lower alkoxy, which may be unsubstituted or substituted by halo or lower alkoxy.

In embodiments of the present invention, for the compound of the formula IIIb any one or more of the following selections is preferred:

$R^{14b}$ is $C_1$-$C_5$ alkyl, or $C_2$-$C_5$, which may be branched, straight chain or cyclic, and which is optionally substituted with 1 to 3 substituents selected from halo and hydroxy;

$R^{14b}$ is $C_4$-$C_6$ alkyl, which may be branched, straight chain or cyclic, and which is optionally substituted with 1 to 3 substituents selected from halo and hydroxy;

the optional substituents, if present on $R^{14b}$ are halo, and most preferably are fluoro; and $R^{3b}$ is lower alkoxy, which may be unsubstituted or substituted by halo or lower alkoxy.

In preferred embodiments of for compounds of Formula IIIa, there is provided a compound of the formula IIIc:

IIIc wherein:

$R^{14c}$ is $C_4$-$C_6$ alkyl, and preferably $C_4$-$C_5$ alkyl, which may be branched, straight chain or cyclic, and which is optionally substituted with 1 to 3 substituents selected from halo and hydroxy; and $R^{3c}$ is selected from the group consisting of H and lower alkoxy, which may be unsubstituted or substituted by halo or lower alkoxy.

In preferred embodiments of the present invention, there is provided a compound of the formula IIId:

IIId wherein:

$R^{13d}$ and $R^{14d}$ are independently selected from the group consisting of H and $C_1$-$C_6$ alkyl, which may be branched, straight chain or cyclic, and which is optionally substituted with 1 to 3 substituents selected from halo and hydroxy;

alternatively, $R^{13d}$ and $R^{14d}$ may be taken together to form a five or six membered heterocyclic ring having 1 to 3 heteroatoms, and which is optionally substituted by from 1 to 3 substituents independently selected from halo, $C_1$-$C_3$ alkyl, $C_1$-$C_3$ alkoxy, oxo, and hydroxy; and $R^{3d}$ is selected from the group consisting of H and lower alkoxy, which may be optionally substituted by halo or lower alkoxy.

In preferred embodiments for the compound of formula IIId, $R^{13c}$ and $R^{14c}$ are be taken together form a morpholine group.

The term "heteroatom" as used herein means an atom of any element other than carbon or hydrogen. Preferred heteroatoms are boron, nitrogen, oxygen, phosphorus, sulfur and selenium. Most preferred are nitrogen or oxygen.

The term "alkyl" refers to the radical of saturated aliphatic groups, including straight-chain alkyl groups, branched-chain alkyl groups, cycloalkyl(alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to four carbons, and more preferably from one to three carbon atoms. Likewise, "lower alkenyl" and "lower alkynyl" have similar chain lengths. Preferred alkyl groups are lower alkyls. In preferred embodiments, a substituent designated herein as alkyl is a lower alkyl.

The term "cycloalkyl" refers to saturated, carbocyclic groups having from 3 to 7 carbons in the ring. Preferred cycloalkyl groups include cyclopropyl, cyclobutyl, cyclopentyl and cyclohexyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5- and 6-membered single-ring aromatic groups that may include from zero to four heteroatoms, for example, benzene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, aryls and/or heterocyclic groups.

The terms "heterocyclyl" or "heterocyclic group" refer to 3- to 10-membered ring structures, more preferably 5- or 6-membered rings, whose ring structures include one to four heteroatoms. Heterocycles can also be polycycles. Heterocyclic groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, aryls and/or heterocyclyls) in which two or more carbons are common to two adjoining rings, e.g., the rings are "fused rings". Rings that are joined through non-adjacent atoms are termed "bridged" rings. Each of the rings of the polycyclic group can be substituted with such substituents as described above, for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" or "halo" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

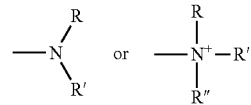

wherein R, R' and R" each independently represent a group permitted by the rules of valence, preferably H, alkyl, alkenyl, alkynyl, aralkyl, aryl, and heterocyclic groups.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. The term lower alkoxy refers to an alkoxy group having from 1 to 4 carbon atoms.

The term "oxo" as used herein refers to an oxygen atom that has a double bond to a carbon.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

As used herein, the definition of each expression, e.g. alkyl, m, n, R, R'', $R^2$, $R^7$, $R^9$, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, stereoisomers, etc., as well as mixtures thereof, are included in this invention.

The invention provides a method of inhibiting one or more glucose transporters in a mammal. In particular, the invention provides a method of inhibiting GLUT1 and GLUT3 in a mammal. The invention provides a method of treating a patient suffering from a disease comprising administering to the patient in need of such treatment a therapeutically effective amount of a compound of Formulas I, II, III, IIIa, IIIb, IIIc, IIId, IV, or V. In certain such embodiments, the compounds of Formulas I, II, III, IIIa, IIIb, IIIc, IIId, IV, or V inhibit GLUT1 and GLUT3.

The invention provides a method of treating an autoimmune disorder in a subject comprising administering to the subject a therapeutically effective amount of a compound of Formulas I, II, III, IIIa, IIIb, IIIc, IIId, IV, or V. Autoimmune disorders include, without limitation, rheumatoid arthritis, multiple sclerosis, systemic lupus erythematosus (SLE; lupus), psoriasis, Crohn's disease, atopic dermatitis, eczema, or graft-versus-host disease (GVHD), Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia**, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, Wegener's granulomatosis (now termed Granulomatosis with Polyangiitis (GPA)

The invention provides a method of treating inflammation in a subject comprising administering to the subject a therapeutically effective amount of a compound of Formulas I, II, III, IIIa, IIIb, IIIc, IIId, IV, or V. Inflammation includes, without limitation, asthma, cardiovascular inflammation, renal inflammation, arteriosclerosis and sepsis. Other inflammatory conditions that can be treated by methods of the invention include fibrotic conditions (including, e.g., idiopathic pulmonary fibrosis, NASH, scleroderma, systemic sclerosis, and cirrhosis).

In one aspect, the present invention provides pharmaceutically acceptable compositions which comprise a therapeutically-effective amount of one or more of the compounds of Formulas I, II, III, IIIa, IIIb, IIIc, IIId, IV, or V, formulated together with one or more pharmaceutically excipients. As described below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals with toxicity, irritation, allergic response, or other problems or complications, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10)glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19)ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, e.g., Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, e.g., Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable excipients including a pharmaceutically-acceptable carrier, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

In certain embodiments, a dose of a compound or a composition is administered to a subject every day, every other day, every couple of days, every third day, once a week, twice a week, three times a week, or once every two weeks. If desired, the effective daily dose of the active compound may be administered as two, three, four, five, six or more sub-doses administered separately at appropriate intervals throughout the day, optionally, in unit dosage forms. In some embodiments, a dose(s) of a compound or a composition is administered for 2 days, 3 days, 5 days, 7 days, 14 days, or 21 days. In certain embodiments, a dose of a compound or a composition is administered for 1 month, 1.5 months, 2 months, 2.5 months, 3 months, 4 months, 5 months, 6 months or more.

The above-described administration schedules are provided for illustrative purposes only and should not be considered limiting. A person of ordinary skill in the art will readily understand that all doses are within the scope of the invention.

While it is possible for a compound of the present invention to be administered alone, it is preferable to administer the compound as a pharmaceutical formulation (composition).

The patient receiving this treatment is any animal in need, including primates, in particular humans, and other mammals such as equines, cattle, swine and sheep; and poultry and pets in general.

The compounds for use in the methods of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

Microemulsification technology may be employed to improve bioavailability of lipophilic (water insoluble) pharmaceutical agents. Examples include Trimetrine (Dordunoo, S. K., et al., Drug Development and Industrial Pharmacy, 17(12), 1685-1713, 1991) and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-.di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). The polymers used in the present invention have a significantly smaller molecular weight, approximately 100 daltons, compared to the large MW of 5000 daltons or greater that used in standard pegylation techniques. Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

The above-described administration schedules are provided for illustrative purposes only and should not be considered limiting. A person of ordinary skill in the art will readily understand that all doses are within the scope of the invention.

Compounds of the invention can be advantageously administered with second agents to patients in need thereof. When GLUT inhibitor is administered with a second agent, the GLUT inhibitor and the second agent can be administered sequentially or concomitantly. Sequentially means that one agent is administered for a time followed by administration of the second agent, which may be followed by administration of the first agent. When agents are administered sequentially, the level or one agent may not be maintained at a therapeutically effective level when the second agent is administered, and vice versa. Concomitantly means that the first and second agent are administered according to a schedule that maintains both agents at a substantially therapeutically effective level, even though the agents are not administered simultaneously. Each agent can be administered in single or multiple doses, and the doses can be administered on any schedule, including, without limitation, twice daily, daily, weekly, every two weeks, and monthly.

The invention also includes adjunctive administration. Adjunctive administration means that a second agent is administered to a patient in addition to a first agent that is already being administered to treat a disease or disease symptom. In some embodiments, adjunctive administration involves administering a second agent to a patient in which administration of the first agent did not sufficiently treat a disease or disease symptom. In other embodiments, adjunctive administration involves administration of the second agent to a patient whose disease has been effectively treated by administration of the first agent, with the expectation that the adjunctive treatment improves the outcome of the treatment. In some embodiments, the effect of administering the first and second agents is synergistic. In some embodiments, administration of the first and second agents prevents or lengthens the time until relapse, compared to administration of either of the agents alone. In some embodiments, administration of the first and second agents allows for reduced dosage and/or frequency of administration of the first and second agent.

Anti-inflammatories and immunosuppressants that can be administer in combination with the compounds of the present invention include steroid drugs such as glucocorticoids (e.g., dexamethasone), FK506 (tacrolimus), ciclosporin, fingolimod, interferon, such as IFNβ or IFNγ, a tumor necrosis factor-alpha (TNF-α) binding protein such as infliximab (Remicade), etanercept (Enbrel), or adalimumab (Humira), mycophenolic acid, MMF, Methotrexate, NSAID, Statins, Sirolimus/temsirolimus/everolimus, abatacept (Orencia), anakinra (Kineret), certolizumab (Cimzia), golimumab (Simponi), ixekizumab (Taltz), natalizumab (Tysabri), rituximab (Rituxan), secukinumab (Cosentyx), tocilizumab (Actemra), ustekinumab (Stelara), vedolizumab (Entyvio), basiliximab (Simulect), daclizumab (Zinbryta), muromonab (Orthoclone OKT3), Jakafi (Ruxolitinib), Xeljanz (Tofacitnib), and Otezla (Apremilast).

Compounds disclosed herein may be prepared according to the following schemes. Compounds of formula E may be prepared by reacting a compound of formula A and an alkylating agent $R^1X$ in the presence of a base such as potassium carbonate to give the compound of formula B; Reduction of the said formula B compound with hydrogen in the presence of a catalyst such as palladium on carbon or with other commonly used nitro group reducing agents such as $Sn(II)Cl_2$ or Fe or Zn metals to give the compound of formula C; Reacting said formula C compound with urea to give the compound of formula D; Reacting said formula D compound with $POCl_3$ or $SOCl_2$. The reaction is shown in Scheme 1.

Scheme 1

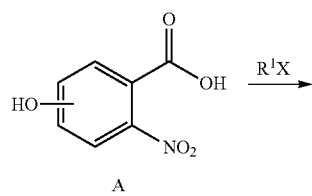

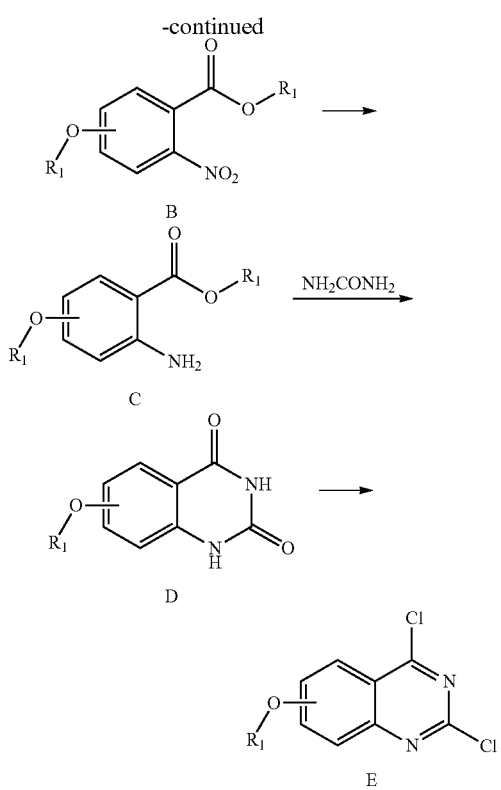

Compounds of formula H may be prepared by reacting a compound of formula F and a compound of formula G with Suzuki coupling reactions using a palladium catalyst such as $Pd(PPh_3)_4$ (Scheme 2).

Scheme 2

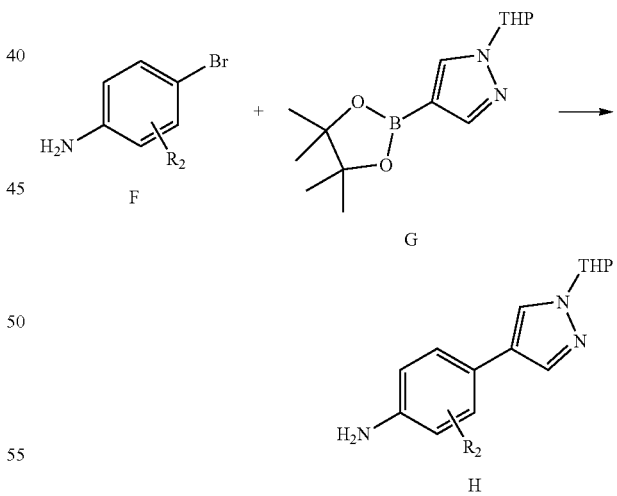

Compounds of formula M may be prepared by reacting an amine I and chloroacetyl chloride J to give the compound of formula K; Reacting said formula K compound with a compound of formula of L. Alternatively, compounds of formula M may also be prepared by reacting said formula K compound with a compound of formula N to give the compound of formula O; Reacting said formula O compound with bis(pinacolato)diboron using standard palladium-mediated coupling reactions. The reaction is shown in Scheme 3.

Scheme 3

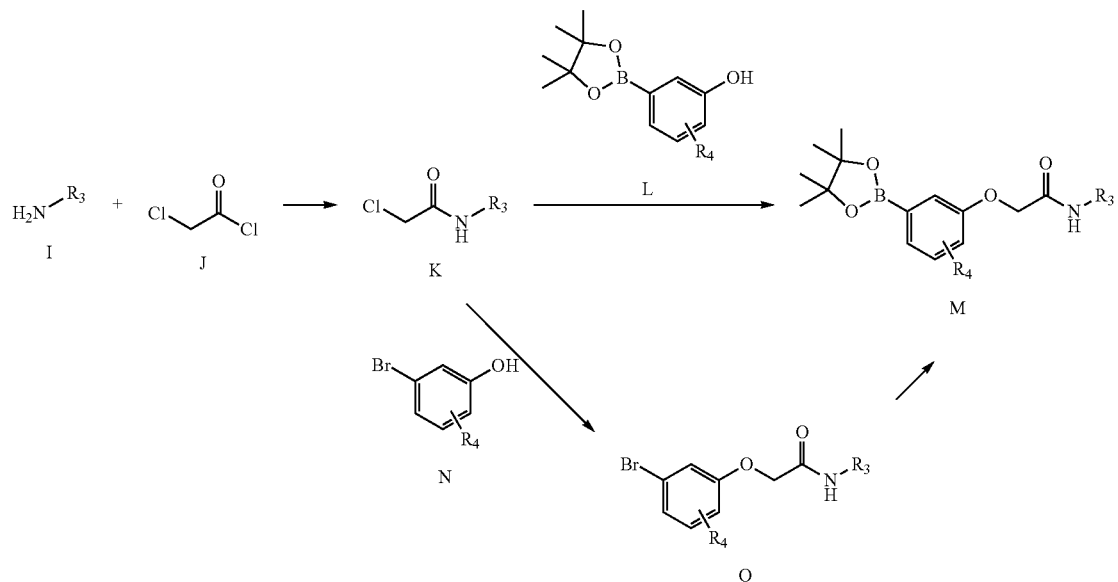

Compounds of formula S may be prepared by reacting a compound of formula P and a compound of formula H with a protecting group such as THP on the pyrazole nitrogen to give the compound of formula Q; Reacting said formula Q compound with a compound of formula of M via Suzuki couplings to give the compound of formula R; Deprotection of said formula R compound with an acid such as TFA or HCl. Alternatively, compounds of formula S may be prepared directly from a compound of formula U without a protecting group on the pyrazole nitrogen but under much harsher reaction conditions such as with elevated temperatures. The reaction is shown in the Scheme 4.

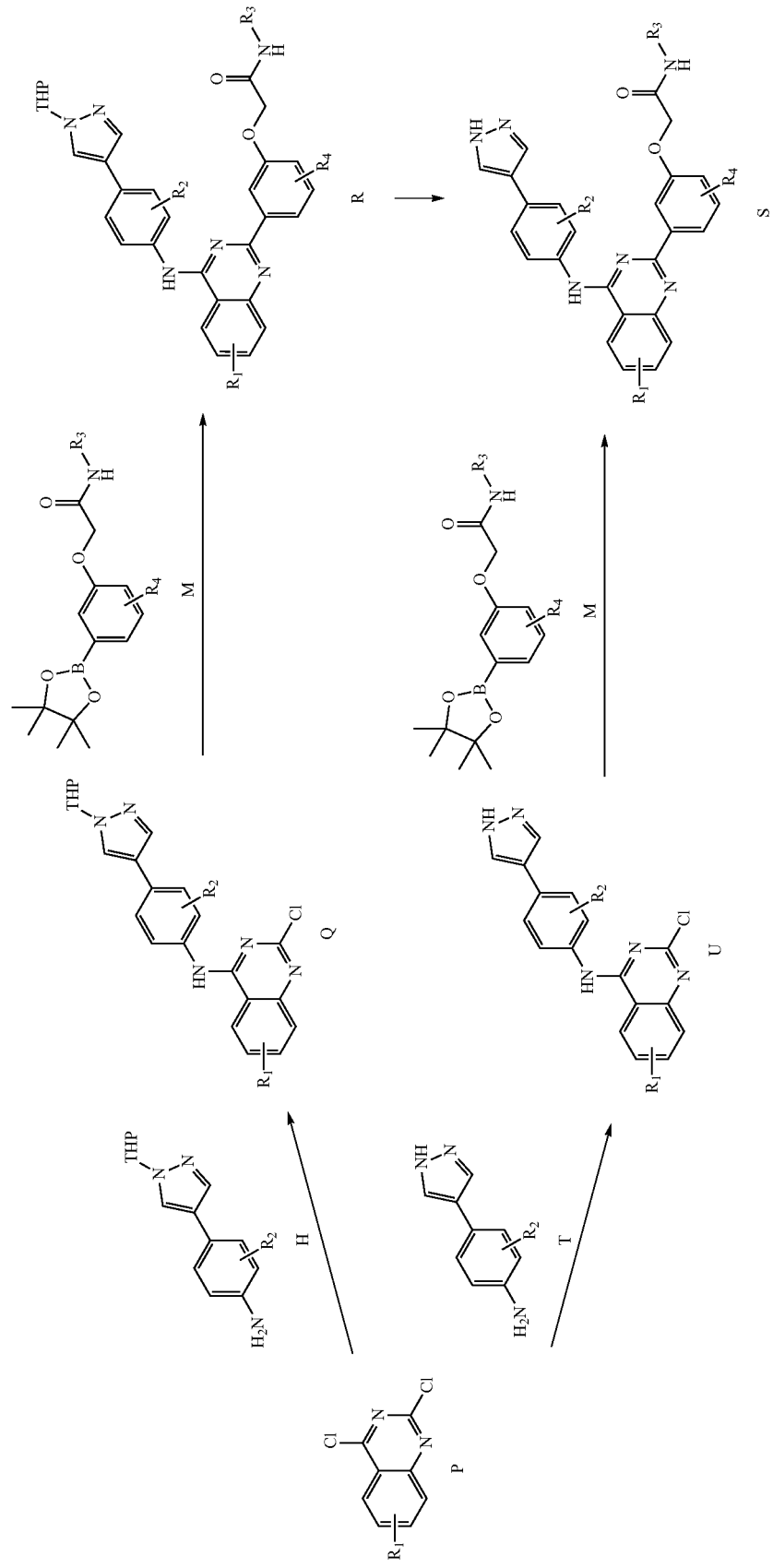

It is to be understood and expected that variations in the principles of invention herein disclosed can be made by one skilled in the art and it is intended that such modifications are to be included within the scope of the present invention. The following Examples further illustrate the invention, but should not be construed to limit the scope of the invention in any way. All references cited herein are hereby incorporated by reference in their entirety.

EXAMPLES

General experimental methods: All solvents and reagents were obtained commercially and used as received. $^1$H NNR spectra were recorded on a Bruker instrument (300 MHz or 400 MHz) in the cited deuterated solvents. Chemical shifts are given in ppm, and coupling constants are in hertz. All final compounds were purified by flash chromatography using 220-400 mesh silica gel or reverse-phase HPLC with $CH_3CN$/water as the solvents. Thin-layer chromatography was done on silica gel 60 F-254 (0.25-nm thickness) plates. Visualization was accomplished with UV light and/or 10% phosphomolybdic acid in ethanol. Nominal (low resolution) mass spectra were acquired on either a Waters LCT or an Applied Biosystems API 3000 mass spectrometer. High resolution mass spectra (HRMS) were acquired on either a Waters LCT or an Agilent TOF mass spectrometer. All other LC-MS experiments were done on an Agilent 1100 HPLC coupled with an Agilent single quadrupole mass spectrometer. Compound purity was determined by a LC-MS with 230 nM and 254 nM wavelengths. All final compounds reported here have purity≥95%.

Example 1

2-(3-(4-((4-(1H-pyrazol-4-yl)phenyl)amino)-6-ethoxyquinazolin-2-yl)phenoxy)-N-cyclopropylacetamide

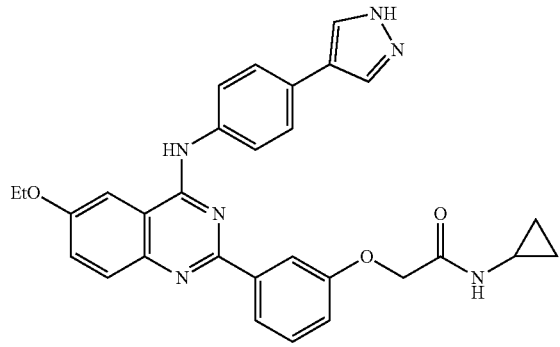 [SMILES: CCOc1ccc2nc(-c3cccc(OCC(=O)NC4CC4)c3)nc(Nc3ccc(-c4cn[nH]c4)cc3)c2c1]

Example 1A 1-(tetrahydro-2H-pyran-2-yl)-4-(4,4,5,5-tetramethyl-1,3,2-dioxaborolan-2-yl)-1H-pyrazole

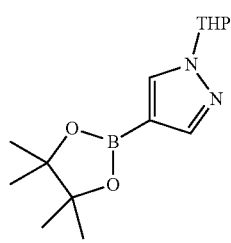

To a solution of 4-(4,4,5,5-tetramethyl-1,3,2-dioxaborolan-2-yl)-1H-pyrazole (110.00 g, 566.89 mmol) in DCM (1000 mL) was added dihydropyran (95.37 g, 1.13 mol, 103.66 mL) and $TsOH.H_2O$ (53.92 g, 283.45 mmol). The mixture was stirred at 20° C. for 4 h. TLC (petroleum ether/EtOAc=5/1) indicated starting material was consumed completely and one main new spot ($R_f$=0.4) formed. LCMS showed starting material was consumed completely and one main peak with desired mass was detected. The reaction mixture was concentrated under reduced pressure to remove volatiles. The residue was diluted with sat. $NaHCO_3$ (350 mL) and the mixture was extracted with EtOAc (2×500 mL). The combined organic layers were dried over $Na_2SO_4$, filtered, and concentrated under reduced pressure to provide a residue. The residue was purified by column chromatography with petroleum ether/ethyl acetate (from 20/1 to 15/1) to afford the title compound (142.00 g, 90%) as colorless oil. $^1$H NMR (400 MHz, DMSO-$d_6$) 400 MHz δ 8.06 (s, 1H), 7.61 (s, 1H), 5.42 (dd, J=10.0, 2.0 Hz, 1H), 3.94-3.86 (m, 1H), 3.66-3.54 (m, 1H), 2.17-2.03 (m, 1H), 1.96-1.82 (m, 2H), 1.77-1.37 (m, 3H), 1.33-1.18 (m, 12H). MS (ES+) m/e 279 (M+H)$^+$.

Example 1B 4-(1-(tetrahydro-2H-pyran-2-yl)-1H-pyrazol-4-yl)aniline

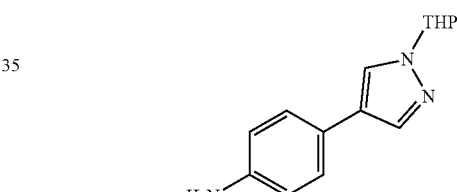

A mixture of compound 1-(tetrahydro-2H-pyran-2-yl)-4-(4,4,5,5-tetramethyl-1,3,2-dioxaborolan-2-yl)-1H-pyrazole (141.00 g, 506.92 mmol), 4-bromoaniline (87.20 g, 506.92 mmol), $K_2CO_3$ (140.12 g, 1.01 mol), Pd(dppf)$Cl_2$ (37.09 g, 50.69 mmol) in dioxane (900.00 mL) and $H_2O$ (90.00 mL) was degassed and purged with $N_2$ for 3 times, then the mixture was stirred at 100° C. for 16 hours under $N_2$ atmosphere. LCMS showed desired compound was the major product. TLC (petroleum ether/EtOAc=1:1$R_f$=0.62) showed that a small amount of starting material remained and a new major spot ($R_f$=0.20) formed. The reaction mixture was cooled to room temperature and quenched by addition water (1 L). The mixture was extracted with EtOAc (3×1 L). The combined organic layers were washed with brine (1.5 L), dried over $Na_2SO_4$, filtered and concentrated under reduced pressure to provide a residue. The residue was purified by column chromatography (SiO$_2$, Petroleum ether/EtOAc: from 10:1 to 5:1) to afford the title compound (81.00 g 66%) as a yellow solid. $^1$H NMR (400 MHz, DMSO-$d_6$ 400 MHz) δ 8.05 (s, 1H), 7.72 (s, 1H), 7.25 (d, J=8.4 Hz, 2H), 6.55 (d, J=8.4 Hz, 2H), 5.36-5.33 (m, 1H), 5.03 (s, 2H), 3.92 (d, J=12.4 Hz, 1H), 3.67-3.57 (m, 1H), 2.16-2.04 (m, 1H), 1.97-1.85 (m, 2H), 1.75-1.60 (m, 1H), 1.53 (d, J=3.2 Hz, 2H). MS (ES+) m/e 244 (M+H)$^+$.

Example 1C

Ethyl 5-ethoxy-2-nitrobenzoate

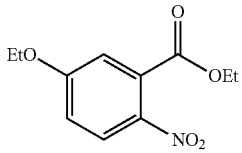

To a solution of compound 5-hydroxy-2-nitrobenzoic acid (130.00 g, 709.92 mmol) in DMF (800.00 mL) was added $K_2CO_3$ (196.24 g, 1.42 mol) and EtI (442.88 g, 2.84 mol). The mixture was stirred at 80° C. for 16 hour. LCMS showed starting material was consumed completely. The reaction mixture was cooled to room temperature and quenched by addition of water (1 L). The mixture was extracted with EtOAc (2×2 L). The combined organic layers were washed with brine (3×1 L), dried over $Na_2SO_4$, filtered, and concentrated under reduced pressure to provide the title compound (141.00 g, 83%) as a yellow solid. $^1$H NMR (400 MHz, DMSO-$d_6$) δ 8.15-8.09 (m, 1H), 7.29-7.19 (m, 2H), 4.31 (q, J=7.2 Hz, 2H), 4.20 (q, J=7.2 Hz, 2H), 1.35 (t, J=6.80 Hz, 3H), 1.27 (t, J=7.2 Hz, 3H). MS (ES+) m/e 240 (M+H)$^+$.

Example 1D

Ethyl 2-amino-5-ethoxybenzoate

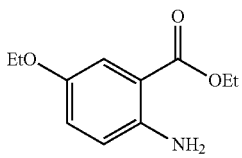

To a solution of compound ethyl 5-ethoxy-2-nitrobenzoate (75.00 g, 313.52 mmol, two batches) in MeOH (600.00 mL) was added Pd/C (8 g, 10% w/w %, wet) under $N_2$. The suspension was degassed under vacuum and purged with $H_2$ for several times. The mixture was stirred under $H_2$ (50 psi) at 40° C. for 16 hours. LCMS showed that a major peak formed and was the desired compound and TLC (petroleum ether/EtOAc=3:1 Rf=0.56) showed a new major spot. The reaction mixture was filtered and concentrated under reduced pressure to give the title compound (117.00 g, 89%) as an off-white solid. $^1$H NMR (400 MHz, DMSO-$d_6$) δ 7.18 (d, J=3.2 Hz, 1H), 6.97 (dd, J=8.8, 2.8 Hz, 1H), 6.73 (d, J=8.8 Hz, 1H), 6.25 (s, 2H), 4.25 (q, J=7.2 Hz, 2H), 3.89 (q, J=7.2 Hz, 2H), 1.28 (td, J=10.8, 7.2 Hz, 6H). MS (ES+) m/e 210 (M+H)$^+$.

Example 1E

6-ethoxyquinazoline-2,4-diol

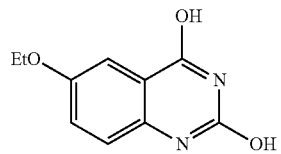 [SMILES: CCOc1ccc2nc(O)nc(O)c2c1]

Ethyl 2-amino-5-ethoxybenzoate (100.00 g, 477.92 mmol) and urea (574.08 g, 9.56 mol) was stirred at 180° C. for 4 hour. LCMS showed that the desired compound was the major peak. The reaction mixture was cooled to room temperature and diluted with water (3 L). White solid precipitated and the mixture was stirred at room temperature for 16 hours. After filtration the cake was dispersed in toluene and dried under vacuum for 4 times to provide the title compound. (158.00 g) as a white solid that was used directly for next step reaction without further purification. $^1$H NMR (400 MHz, DMSO-$d_6$) δ 7.32-7.23 (m, 1H), 7.11 (d, J=8.8 Hz, 1H), 4.04 (q, J=6.8 Hz, 2H), 1.32 (t, J=7.2 Hz, 3H). MS (ES+) m/e 207 (M+H)$^+$.

Example 1F

2,4-dichloro-6-ethoxyquinazoline

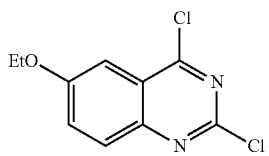 [SMILES: CCOc1ccc2nc(Cl)nc(Cl)c2c1]

To a mixture of 6-ethoxyquinazoline-2,4-diol (138.00 g, 669.25 mmol) in $POCl_3$ (350.00 mL) was added DIPEA (86.49 g, 669.25 mmol). The reaction was stirred at 90° C. for 20 hours. LCMS showed starting material was consumed completely and the desired compound was the major product. An additional batch was synthesized. The combined batches were concentrated under reduced pressure to remove volatiles. The residue was diluted with water (30 L) and basified by sat. $NaHCO_3$ at 0° C. to pH>10. The mixture was extracted with EtOAc (3×6 L). The organic layers were dried over $Na_2SO_4$, filtered, and concentrated under reduced pressure to give a residue. The residue was purified by column chromatography ($SiO_2$, Petroleum ether/Ethyl acetate: from 20/1 to 8/1) to afford the title compound as a yellow solid (90.3 g). $^1$H NMR (400 MHz, DMSO-$d_6$) δ 7.97 (d, J=9.2 Hz, 1H), 7.79 (dd, J=9.2, 2.8 Hz, 1H), 7.44 (d, J=2.8 Hz, 1H), 4.25 (q, J=6.8 Hz, 2H), 1.42 (t, J=6.8 Hz, 3H). MS (ES+) m/e 243 (M+H)$^+$.

Example 1G 2-chloro-6-ethoxy-N-(4-(1-(tetrahydro-2H-pyran-2-yl)-1H-pyrazol-4-yl)phenyl)quinazolin-4-amine

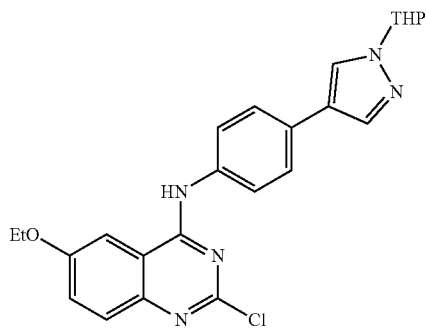

To a solution of 2,4-dichloro-6-ethoxyquinazoline (35.00 g, 143.98 mmol) and 4-(1-(tetrahydro-2H-pyran-2-yl)-1H-pyrazol-4-yl)aniline (35.03 g, 143.98 mmol) in THF (50.00 mL) and H$_2$O (50.00 mL) was added KOAc (28.26 g, 287.96 mmol). The mixture was stirred at 50° C. for 16 hours. LCMS showed that the major peak was the desired compound. The reaction mixture was cooled to room temperature and quenched by addition of water (2 L). Then the mixture was extracted with EtOAc (3×1 L). The combined organic layers were washed with brine (1.2 L), dried over Na$_2$SO$_4$, filtered, and concentrated under reduced pressure to give a residue. The residue was purified by column chromatography (SiO2, Petroleum ether/Ethyl acetate: from 20/1 to 1:1) to afford the title compound (55.00 g, 85%) as a yellow solid. $^1$H NMR (400 MHz, DMSO-d$_6$) δ 9.97 (s, 1H), 8.35 (s, 1H), 8.02-7.89 (m, 2H), 7.82-7.73 (m, 2H), 7.73-7.66 (m, 2H), 7.64 (d, J=8.8 Hz, 1H), 7.53-7.44 (m, 1H), 5.41 (d, J=9.2 Hz, 1H), 4.19 (q, J=6.4 Hz, 2H), 3.95 (d, J=10.8 Hz, 1H), 3.73-3.57 (m, 1H), 2.23-2.06 (m, 1H), 2.03-1.88 (m, 2H), 1.77-1.62 (m, 1H), 1.55 (s, 2H), 1.42 (t, J=6.8 Hz, 3H). MS (ES+) m/e 450 (M+H)$^+$.

Example 1H 2-chloro-N-cyclopropylacetamide

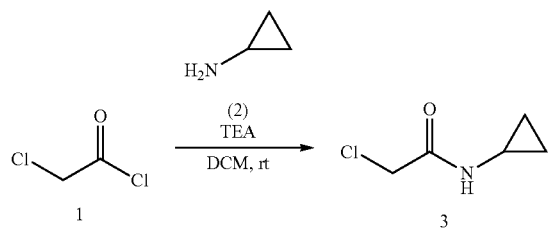

To a solution of cyclopropanamine (5.00 g, 87.58 mmol, 6.10 mL) and TEA (17.72 g, 175.16 mmol, 24.27 mL) in CH$_2$Cl$_2$ (100.00 mL) was added dropwise 2-chloroacetyl chloride (6.59 g, 58.39 mmol, 4.64 mL) at 0° C. over 0.5 hour. The mixture was then stirred at 25° C. for 3 hour. TLC (Petroleum ether/Ethyl acetate=3:1, R$_f$=0.3) indicated a major new spot formed. The reaction mixture was washed with H$_2$O (100 mL), HCl (1 N, 100 mL) and brine (100 mL), dried over Na$_2$SO$_4$, filtered, and concentrated under reduced pressure to provide the title compound (3.30 g, crude) as a black-brown solid which was used in the next step reaction without further purification.

Example 1I 2-(3-bromophenoxy)-N-cyclopropylacetamide

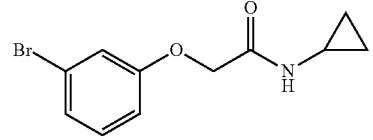 [SMILES: O=C(COc1cccc(Br)c1)NC1CC1]

To a solution of 3-bromophenol (3.42 g, 19.76 mmol) and 2-chloro-N-cyclopropylacetamide (3.30 g, 24.70 mmol) in MeCN (100.00 mL) was added K$_2$CO$_3$ (6.83 g, 49.40 mmol). The mixture was stirred at 80° C. for 16 hours. TLC (Petroleum ether/Ethyl acetate=3:1, Rf=0.2) showed that a main new spot was formed. The reaction mixture was cooled to room temperature and quenched by addition water (100 mL). The resulting was extracted with EtOAc (2×100 mL). The combined organic layers were washed with brine (2×100 mL), dried over Na$_2$SO$_4$, filtered, and concentrated under reduced pressure to give a residue. The residue was purified by column chromatography (SiO$_2$, Petroleum ether/Ethyl acetate: from 20:1 to 1:1) to provide the compound (4.40 g, 65%) as a yellow oil.

Example 1J

N-cyclopropyl-2-(3-(4,4,5,5-tetramethyl-1,3,2-dioxaborolan-2-yl)phenoxy)acetamide

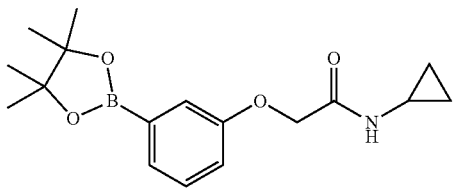 [SMILES: CC1(C)OB(c2cccc(OCC(=O)NC3CC3)c2)OC1(C)C]

A mixture of 2-(3-bromophenoxy)-N-cyclopropylacetamide (4.40 g, 16.29 mmol), 4,4,4',4',5,5,5',5'-octamethyl-2,2'-bi(1,3,2-dioxaborolane) (4.55 g, 17.92 mmol), AcOK (3.20 g, 32.58 mmol) and Pd(dppf)Cl$_2$ (1.19 g, 1.63 mmol) in dioxane (60.00 mL) was degassed and purged with N$_2$ for 3 times, and then the mixture was stirred at 85° C. for 16 hour under N$_2$ atmosphere. LCMS showed that 2-(3-bromophenoxy)-N-cyclopropylacetamide was completely consumed to give a main new peak with the desired MS. The reaction mixture was cooled to room temperature and diluted with H$_2$O (30 mL). The resulting mixture was extracted with EtOAc (3×30 mL). The combined organic layers were washed with brine (3×30 mL), dried over Na$_2$SO$_4$, filtered, and concentrated under reduced pressure to give a residue. The residue was purified by column chromatography (SiO$_2$, Petroleum ether/Ethyl acetate: from 50:1 to 5:1) to provide the title compound (4.9 g, crude) as a colorless oil. The product was difficult to purify via column chromatography. The crude product (200 mg) was used into next step without further purification. But based on the result of next step, the obtained impure product needed further purification. ¹H NMR (400 MHz, DMSO-d₆) δ 8.14 (d, J=4.0 Hz, 1H), 7.31-7.20 (m, 2H), 7.07 (m, 1H), 7.06 (d, J=8.0 Hz, 1H), 4.43 (s, 2H), 2.72-2.65 (m, 1H), 1.29 (s, 12H), 0.65-0.62 (m, 2H), 0.51-0.48 (m, 2H). MS (ES+) m/e 317 (M+H)⁺.

Example 1K

N-cyclopropyl-2-(3-(6-ethoxy-4-((4-(1-(tetrahydro-2H-pyran-2-yl)-1H-pyrazol-4-yl)phenyl)amino)quinazolin-2-yl)phenoxy)acetamide

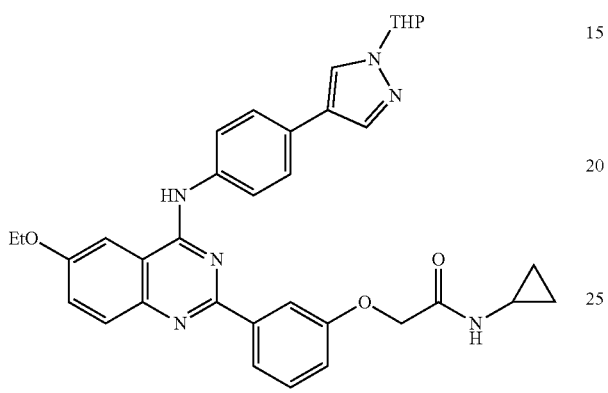

A mixture of 2-chloro-6-ethoxy-N-(4-(1-(tetrahydro-2H-pyran-2-yl)-1H-pyrazol-4-yl)phenyl)quinazolin-4-amine (59.10 mg, 131.36 umol), N-cyclopropyl-2-(3-(4,4,5,5-tetramethyl-1,3,2-dioxaborolan-2-yl)phenoxy)acetamide (50.00 mg, 157.63 umol), K₃PO₄ (55.77 mg, 262.72 umol) and Pd(PPh₃)₄ (15.18 mg, 13.14 umol) in dioxane (5.00 mL) and H₂O (500.00 uL) was degassed and purged with N₂ for 3 times, and then the mixture was stirred at 85° C. for 16 hour under N₂ atmosphere. LCMS showed that of 2-chloro-6-ethoxy-N-(4-(1-(tetrahydro-2H-pyran-2-yl)-1H-pyrazol-4-yl)phenyl)quinazolin-4-amine was consumed and the desired compound formed. The reaction mixture was cooled to room temperature and concentrated under reduced pressure to give a residue. The residue was purified by prep-TLC (SiO₂, Petroleum ether/Ethyl acetate=1:2) to give the title compound (60.00 mg, 66%) as a yellow solid.

Example 1L 2-(3-(4-((4-(1H-pyrazol-4-yl)phenyl)amino)-6-ethoxyquinazolin-2-yl)phenoxy)-N-cyclopropylacetamide

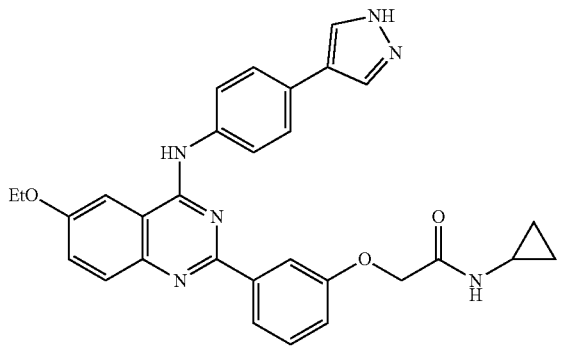 [SMILES: CCOc1ccc2nc(-c3cccc(OCC(=O)NC4CC4)c3)nc(Nc3ccc(-c4cn[nH]c4)cc3)c2c1]

To solution of N-cyclopropyl-2-(3-(6-ethoxy-4-((4-(1-(tetrahydro-2H-pyran-2-yl)-1H-pyrazol-4-yl)phenyl)amino)quinazolin-2-yl)phenoxy)acetamide (60.00 mg, 99.22 umol) in CH₂Cl₂ (3.00 mL) was added HCl/dioxane (4 N, 3.00 mL). The mixture was stirred at 50° C. for 1 hour. LCMS showed~53% peak with desired MS was detected. The reaction mixture was concentrated under reduced pressure to give a residue. The residue was purified by prep-HPLC (FA conditions) to give the title compound (34.5 mg, 61%, FA salt) as a yellow solid. ¹H NMR (400 MHz, DMSO-d₆) δ 9.72 (s, 1H), 8.40 (s, 1H), 8.21 (d, J=4.4 Hz, 1H), 8.10-8.03 (m, 4H), 8.00 (d, J=2.4 Hz, 1H), 7.96 (d, J=8.8 Hz, 2H), 7.80 (d, J=9.2 Hz, 1H), 7.72 (d, J=8.4 Hz, 2H), 7.51 (dd, J=8.8, 2.4 Hz, 1H), 7.42 (t, J=8.4 Hz, 1H), 7.05 (dd, J=9.2, 2.0 Hz, 1H), 4.54 (s, 2H), 4.25 (q, J=6.8 Hz, 1H), 2.75-2.70 (m, 1H), 1.45 (t, J=7.2 Hz, 3H), 0.66-0.61 (m, 2H), 0.55-0.53 (m, 2H). MS (ES+) m/e 521 (M+H)⁺.

Using essentially the same procedures as described for the synthesis of Example1 and using appropriate starting material, the following compounds were synthesized.

Example 2

2-(3-(4-((4-(1H-pyrazol-4-yl)phenyl)amino)-6-ethoxyquinazolin-2-yl)phenoxy)-N-isopropylacetamide

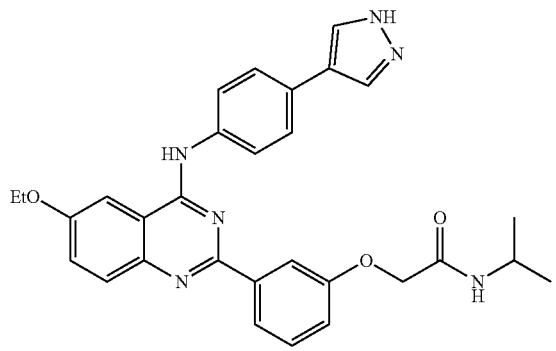 [SMILES: CCOc1ccc2nc(-c3cccc(OCC(=O)NC(C)C)c3)nc(Nc3ccc(-c4cn[nH]c4)cc3)c2c1]

¹H NMR (400 MHz, DMSO-d₆) δ 11.63 (s, 1H), 8.43-8.32 (m, 2H), 8.20 (s, 2H), 8.01-7.95 (m, 3H), 7.88-7.70 (m, 5H), 7.57 (t, J=8.0 Hz, 1H), 7.30 (d, J=8.0 Hz, 1H), 4.61 (s, 2H), 4.31 (t, J=7.2 Hz, 2H), 4.06-4.04 (m, 1H), 1.45 (t, J=6.8 Hz, 3H), 1.08 (d, J=6.4 Hz, 6H). MS (ES+) m/e 523 (M+H)+.

Example 3

2-(3-(4-((4-(1H-pyrazol-4-yl)phenyl)amino)-6-ethoxyquinazolin-2-yl)phenoxy)-N-(tert-butyl)acetamide

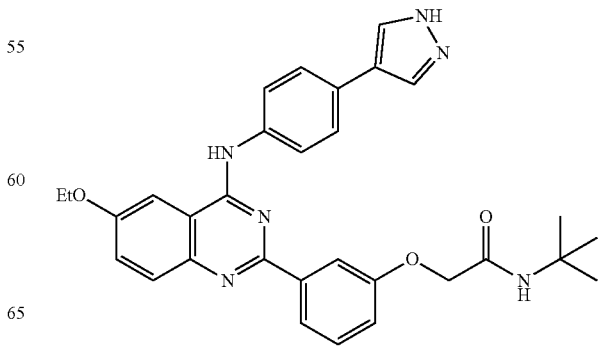

¹H NMR (400 MHz, DMSO-d₆) δ 9.71 (s, 1H), 8.34 (s, 1H), 8.05-8.03 (m, 4H), 7.99 (d, J=2.8 Hz, 1H), 7.95 (d, J=8.4 Hz, 2H), 7.79 (d, J=9.2 Hz, 1H), 7.72 (d, J=8.8 Hz, 2H), 7.52-7.50 (m, 2H), 7.41 (t, J=8.4 Hz, 1H), 7.06-7.04 (m, 1H), 4.50 (s, 2H), 4.28-4.24 (m, 2H), 1.45 (t, J=6.8 Hz, 3H), 1.31 (s, 9H). MS (ES+) m/e 537 (M+H)⁺.

Example 4

2-(3-(4-((4-(1H-pyrazol-4-yl)phenyl)amino)-6-ethoxyquinazolin-2-yl)phenoxy)-N-(tert-pentyl)acetamide

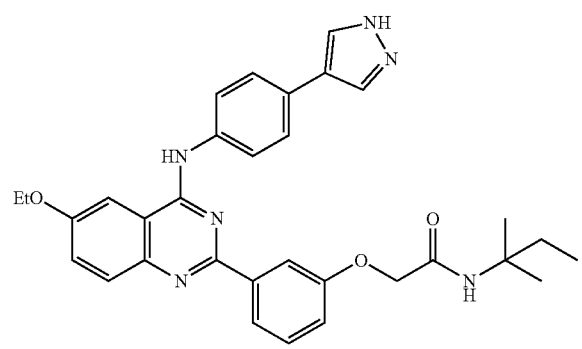 [SMILES: CCOc1ccc2nc(-c3cccc(OCC(=O)NC(C)(C)CC)c3)nc(Nc3ccc(-c4cn[nH]c4)cc3)c2c1]

¹H NMR (400 MHz, DMSO-d₆) δ 9.72 (s, 1H), 8.42 (s, 1H), 8.05-8.02 (m, 4H), 7.99 (d, J=2.8 Hz, 1H), 7.95 (d, J=8.8 Hz, 2H), 7.79 (d, J=9.2 Hz, 1H), 7.72 (d, J=8.4 Hz, 2H), 7.51 (dd, J=9.2, 2.4 Hz, 1H), 7.41 (t, J=7.6 Hz, 1H), 7.35 (s, 1H), 7.05 (dd, J=8.4, 2.0 Hz, 1H), 4.52 (s, 2H), 4.28-4.22 (m, 2H), 1.71-1.65 (m, 2H), 1.45 (t, J=7.2 Hz, 3H), 1.24 (s, 6H), 0.76 (t, J=7.2 Hz, 3H). MS (ES+) m/e 551 (M+H)⁺.

Example 5

2-(3-(4-((4-(1H-pyrazol-4-yl)phenyl)amino)-6-ethoxyquinazolin-2-yl)phenoxy)-N-cyclopentylacetamide

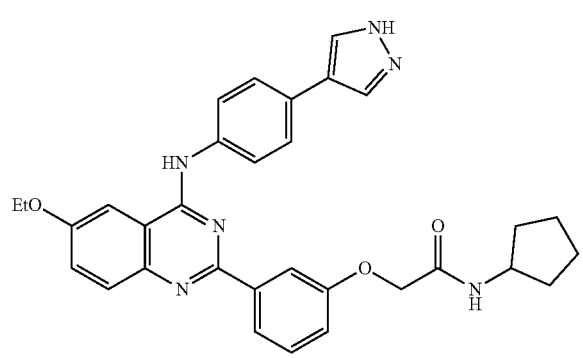 [SMILES: CCOc1ccc2nc(-c3cccc(OCC(=O)NC4CCCC4)c3)nc(Nc3ccc(-c4cn[nH]c4)cc3)c2c1]

¹H NMR (400 MHz, DMSO-d₆) δ 9.71 (s, 1H), 8.27 (s, 1H), 8.10-8.04 (m, 5H), 7.99 (d, J=2.4 Hz, 1H), 7.95 (d, J=8.8 Hz, 2H), 7.79 (d, J=9.2 Hz, 1H), 7.72 (d, J=8.8 Hz, 2H), 7.51 (dd, J=9.2, 2.4 Hz, 1H), 7.42 (t, J=8.0 Hz, 1H), 7.06 (dd, J=7.6, 2.0 Hz, 1H), 4.55 (s, 2H), 4.28-4.22 (m, 3H), 1.81-1.80 (m, 2H), 1.64 (m, 2H), 1.47-1.43 (m, 7H). MS (ES+) m/e 549 (M+H)⁺.

Example 6

2-(3-(4-((4-(1H-pyrazol-4-yl)phenyl)amino)-6-ethoxyquinazolin-2-yl)phenoxy)-N-cyclobutylacetamide

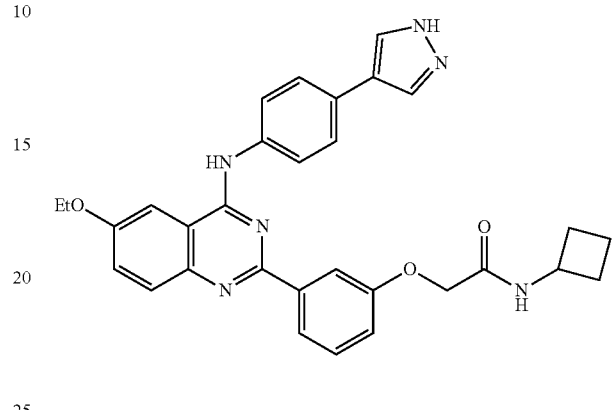

¹H NMR (400 MHz, DMSO-d₆) δ 9.72 (s, 1H), 8.38 (d, J=8.0 Hz, 1H), 8.24 (s, 1H), 8.10-8.04 (m, 4H), 7.99 (d, J=2.4 Hz, 1H), 7.96 (d, J=8.4 Hz, 1H), 7.79 (d, J=9.2 Hz, 1H), 7.73 (d, J=8.4 Hz, 2H), 7.51 (dd, J=9.2, 2.8 Hz, 1H), 7.43 (t, J=8.0 Hz, 1H), 7.07 (dd, J=8.0, 1.6 Hz, 1H), 4.54 (s, 2H), 4.34-4.22 (m, 3H), 2.15-2.13 (m, 2H), 2.06-2.04 (m, 2H), 1.63-1.61 (m, 2H), 1.45 (t, J=7.2 Hz, 3H). MS (ES+) m/e 535 (M+H)⁺.

Example 7

2-(3-(4-((4-(1H-pyrazol-4-yl)phenyl)amino)-6-ethoxyquinazolin-2-yl)phenoxy)-N-(pentan-3-yl)acetamide

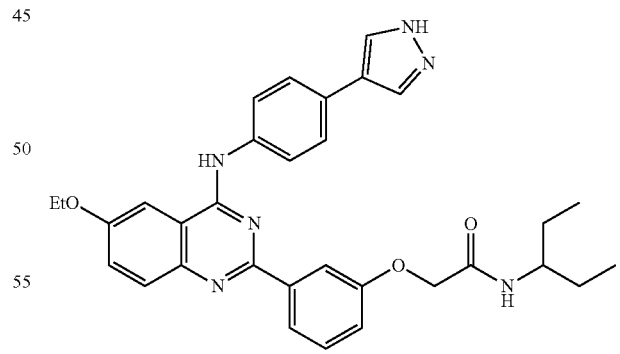

¹H NMR (400 MHz, DMSO-d₆) δ 8.35 (s, 1H), 8.09-8.07 (m, 2H), 8.04 (s, 2H), 7.97 (d, J=8.4 Hz, 2H), 7.84 (d, J=9.2 Hz, 2H), 7.81 (d, J=2.8 Hz, 1H), 7.72-7.70 (m, 3H), 7.50 (dd, J=9.2, 2.8 Hz, 1H), 7.44 (t, J=8.0 Hz, 1H), 7.15 (dd, J=8.0, 2.0 Hz, 1H), 4.67 (s, 2H), 4.30-4.25 (m, 2H), 3.83-3.77 (m, 1H), 1.59-1.45 (m, 7H), 0.88 (t, J=7.6 Hz, 6H). (ES+) m/e 551 (M+H)⁺.

Example 8

2-(3-(4-((4-(1H-pyrazol-4-yl)phenyl)amino)-6-methoxyquinazolin-2-yl)phenoxy)-N-isopropylacetamide

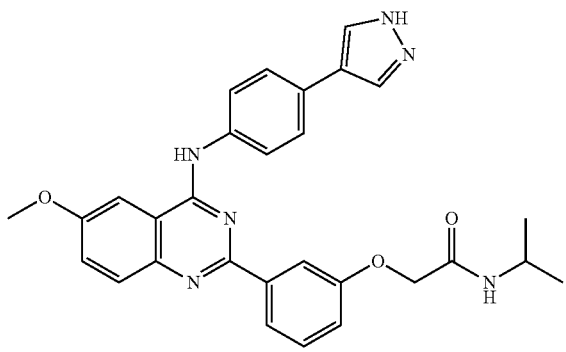 [SMILES: COc1ccc2nc(-c3cccc(OCC(=O)NC(C)C)c3)nc(Nc3ccc(-c4cn[nH]c4)cc3)c2c1]

(ES+) m/e 509 (M+H)+.

Example 9

2-(3-(4-((4-(1H-pyrazol-4-yl)phenyl)amino)-6-methoxyquinazolin-2-yl)phenoxy)-N-cyclopropylacetamide

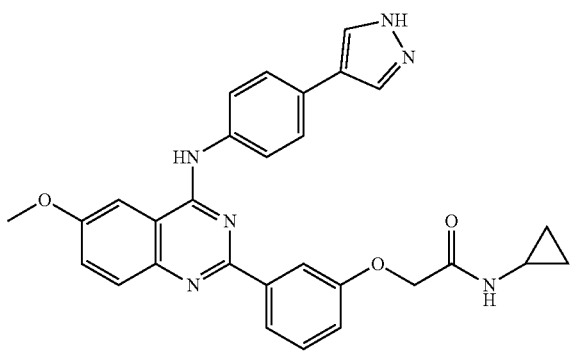 [SMILES: COc1ccc2nc(-c3cccc(OCC(=O)NC4CC4)c3)nc(Nc3ccc(-c4cn[nH]c4)cc3)c2c1]

(ES+) m/e 507 (M+H)+.

Example 10

2-(3-(4-((4-(1H-pyrazol-4-yl)phenyl)amino)-6-methoxyquinazolin-2-yl)phenoxy)-N-cyclopentylacetamide

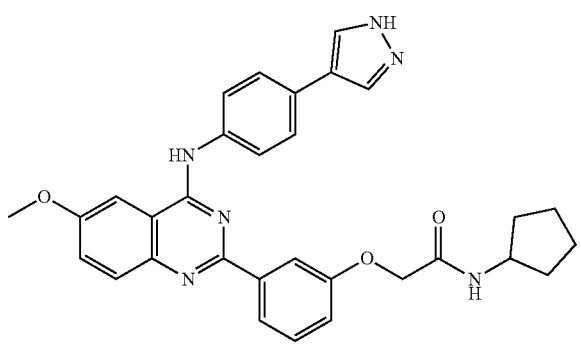 [SMILES: COc1ccc2nc(-c3cccc(OCC(=O)NC4CCCC4)c3)nc(Nc3ccc(-c4cn[nH]c4)cc3)c2c1]

(ES+) m/e 535 (M+H)+.
1H NMR (500 MHz, DMSO-d6) δ 10.75 (s, 1H), 8.14 (s, 3H), 8.07 (d, J=7.5 Hz, 1H), 8.01-7.92 (m, 3H), 7.88 (d, J=8.5 Hz, 2H), 7.82-7.77 (m, 2H), 7.68 (dd, J=9.3, 2.5 Hz, 1H), 7.54 (t, J=8.1 Hz, 1H), 7.22 (dd, J=8.6, 2.5 Hz, 1H), 6.43-6.31 (m, 1H), 4.58 (s, 2H), 4.11 (q, J=6.9 Hz, 1H), 4.01 (s, 3H), 1.89-1.74 (m, 2H), 1.73-1.57 (m, 2H), 1.55-1.40 (m, 4H). (ES+) m/e 535 (M+H)+.

Example 11

2-(3-(4-((4-(1H-pyrazol-4-yl)phenyl)amino)-6-methoxyquinazolin-2-yl)-5-fluorophenoxy)-N-isopropylacetamide 1H NMR (500 MHz, DMSO-d6) δ 10.29 (s, 2H), 8.08 (s, 1H), 8.03 (d, J=8.1 Hz, 1H), 7.94-7.84 (m, 4H), 7.75 (dd, J=20.3, 9.0 Hz, 3H), 7.62 (dd, J=9.2, 2.5 Hz, 1H), 7.05 (d, J=10.5 Hz, 1H), 4.59 (s, 2H), 4.00 (s, 4H), 1.11 (d, J=6.6 Hz, 6H). (ES+) m/e 527 (M+H)+.

Example 12

2-(3-(4-((4-(1H-pyrazol-4-yl)phenyl)amino)-6-methoxyquinazolin-2-yl)phenoxy)-N-propylacetamide 1H NMR (500 MHz, DMSO-d6) δ 10.71 (b, 1H), 8.17 (d, J=16.1 Hz, 4H), 7.97 (d, J=5.8 Hz, 3H), 7.89 (d, J=8.6 Hz, 2H), 7.84-7.76 (m, 2H), 7.68 (d, J=9.1 Hz, 1H), 7.54 (t, J=8.1 Hz, 1H), 7.22 (d, J=8.1 Hz, 1H), 4.61 (s, 2H), 4.01 (s, 3H), 3.11 (dd, J=7.4, 6.0 Hz, 2H), 1.45 (q, J=7.3 Hz, 2H), 0.83 (t, J=7.4 Hz, 3H). (ES+) m/e 509 (M+H)+.

Example 13

2-(3-(4-((4-(1H-pyrazol-4-yl)phenyl)amino)-6-methoxyquinazolin-2-yl)phenoxy)-N-(tert-butyl)acetamide

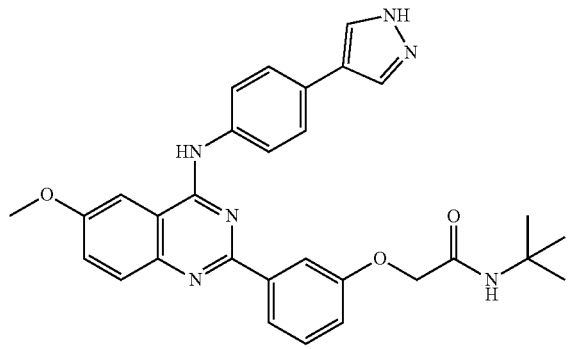 [SMILES: COc1ccc2nc(-c3cccc(OCC(=O)NC(C)(C)C)c3)nc(Nc3ccc(-c4cn[nH]c4)cc3)c2c1]

(ES+) m/e 523 (M+H)$^+$.

Example 14

2-(3-(4-((4-(1H-pyrazol-4-yl)phenyl)amino)-6-methoxyquinazolin-2-yl)phenoxy)-N-isobutylacetamide

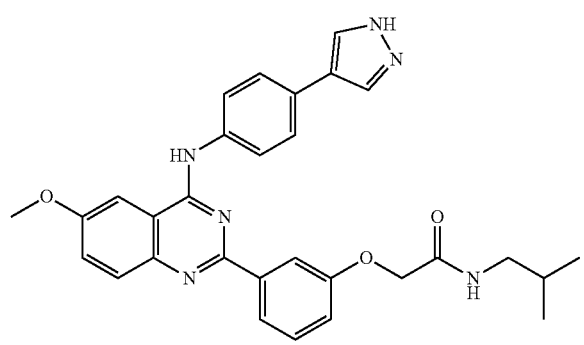 [SMILES: COc1ccc2nc(-c3cccc(OCC(=O)NCC(C)C)c3)nc(Nc3ccc(-c4cn[nH]c4)cc3)c2c1]

(ES+) m/e 523 (M+H)$^+$.

Example 15

2-(3-(4-((4-(1H-pyrazol-4-yl)phenyl)amino)-6-methoxyquinazolin-2-yl)phenoxy)-N-(3,3-difluorocyclobutyl)acetamide

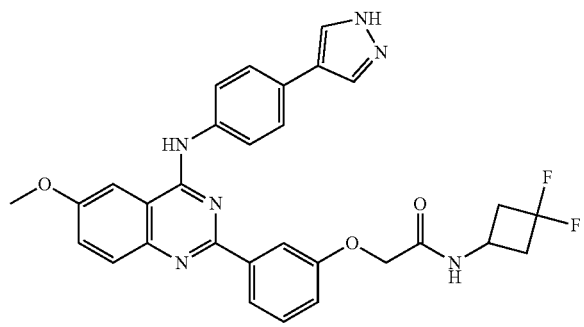 [SMILES: COc1ccc2nc(-c3cccc(OCC(=O)NC4CC(F)(F)C4)c3)nc(Nc3ccc(-c4cn[nH]c4)cc3)c2c1]

(ES+) m/e 557 (M+H)$^+$.

Example 16

2-(3-(4-((4-(1H-pyrazol-4-yl)phenyl)amino)-6-ethoxyquinazolin-2-yl)phenoxy)-N-propylacetamide

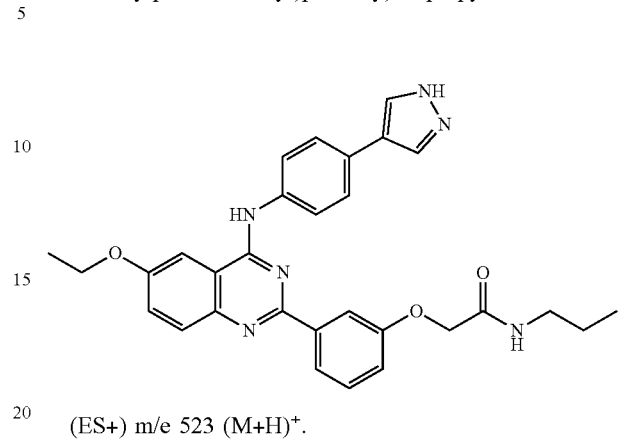

(ES+) m/e 523 (M+H)$^+$.

Example 17

2-(3-(4-((4-(1H-pyrazol-4-yl)phenyl)amino)-6-ethoxyquinazolin-2-yl)phenoxy)-N-isobutylacetamide

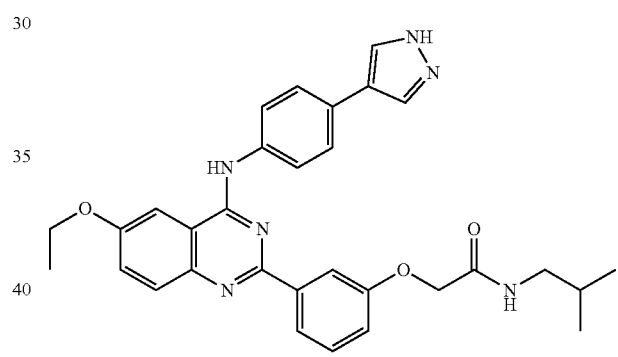

(ES+) m/e 537 (M+H)$^+$.

Example 18

2-(3-(4-((4-(1H-pyrazol-4-yl)phenyl)amino)-6-ethoxyquinazolin-2-yl)phenoxy)-N-(sec-butyl)acetamide

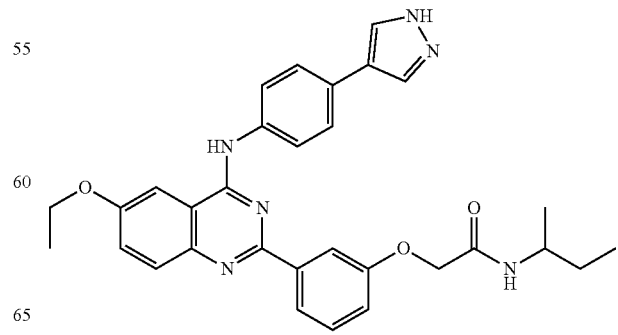 [SMILES: CCCNC(=O)COc1cccc(-c2nc(Nc3ccc(-c4cn[nH]c4)cc3)c3cc(OCC)ccc3n2)c1]

(ES+) m/e 537 (M+H)$^+$.

Example 19

2-(3-(4-((4-(1H-pyrazol-4-yl)phenyl)amino)-6-ethoxyquinazolin-2-yl)phenoxy)-N-(3,3-difluorocyclobutyl)acetamide

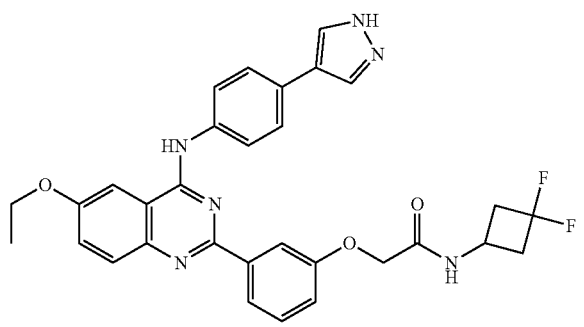 [SMILES: CCOc1ccc2nc(-c3cccc(OCC(=O)NC4CC(F)(F)C4)c3)nc(Nc3ccc(-c4cn[nH]c4)cc3)c2c1]

(ES+) m/e 571 (M+H)+.

Example 20

2-(3-(4-((2-fluoro-4-(1H-pyrazol-4-yl)phenyl)amino)-6-methoxyquinazolin-2-yl)phenoxy)-N-isopropylacetamide

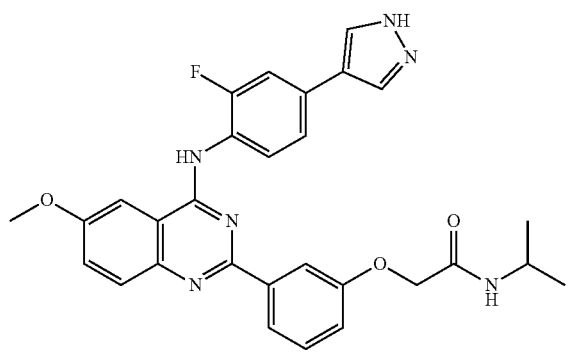 [SMILES: COc1ccc2nc(-c3cccc(OCC(=O)NC(C)C)c3)nc(Nc3ccc(-c4cn[nH]c4)cc3F)c2c1]

(ES+) m/e 527 (M+H)+.

Example 21

2-(3-(6-ethoxy-4-((2-fluoro-4-(1H-pyrazol-4-yl)phenyl)amino)quinazolin-2-yl)phenoxy)-N-isopropylacetamide

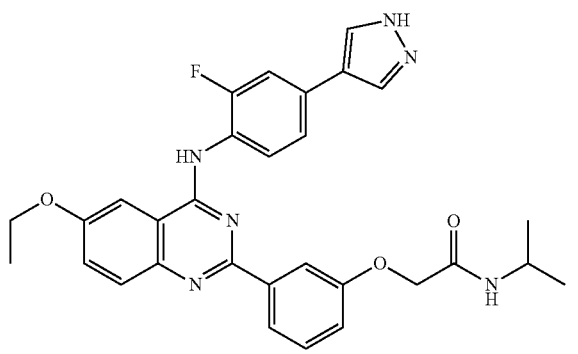 [SMILES: CCOc1ccc2nc(-c3cccc(OCC(=O)NC(C)C)c3)nc(Nc3ccc(-c4cn[nH]c4)cc3F)c2c1]

(ES+) m/e 541 (M+H)+.

Example 22

2-(3-(4-((4-(1H-pyrazol-4-yl)phenyl)amino)-6-methoxyquinazolin-2-yl)phenoxy)-N-(sec-butyl)acetamide

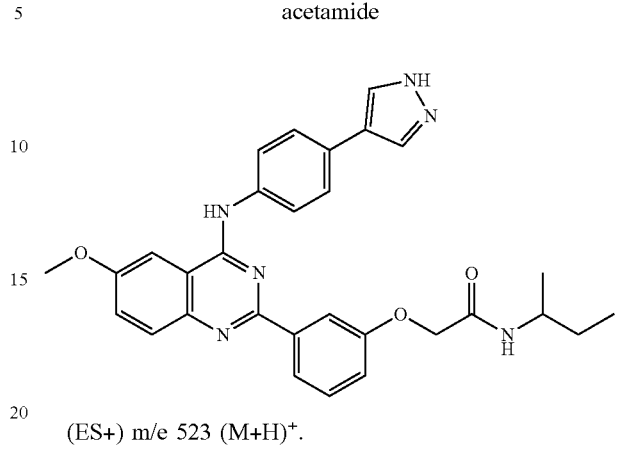

(ES+) m/e 523 (M+H)+.

Example 23

2-(3-(4-((4-(1H-pyrazol-4-yl)phenyl)amino)-6-methoxyquinazolin-2-yl)phenoxy)-N-(1,3-difluoropropan-2-yl)acetamide

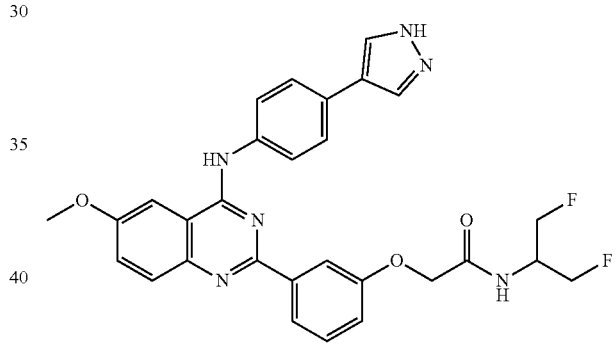

(ES+) m/e 544 (M+H)+.

Example 24

2-(3-(4-((4-(1H-pyrazol-4-yl)phenyl)amino)-6-ethoxyquinazolin-2-yl)phenoxy)-N-(2,2,2-trifluoroethyl)acetamide

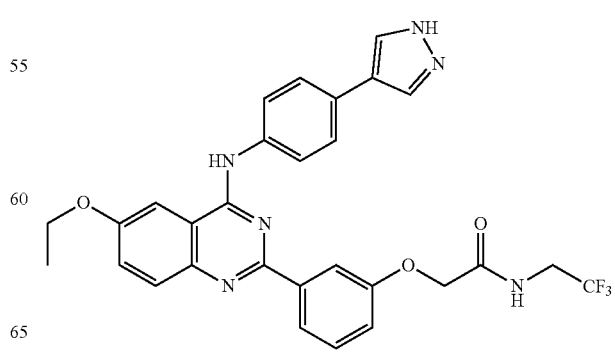

(ES+) m/e 563 (M+H)+.

Example 25

2-(3-(4-((4-(1H-pyrazol-4-yl)phenyl)amino)-6-methoxyquinazolin-2-yl)phenoxy)-N-(2,2,2-trifluoroethyl)acetamide

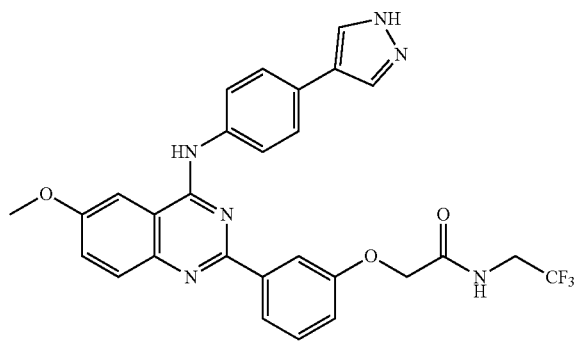 [SMILES: COc1ccc2nc(-c3cccc(OCC(=O)NCC(F)(F)F)c3)nc(Nc3ccc(-c4cn[nH]c4)cc3)c2c1]

(ES+) m/e 549 (M+H)+.

Example 26

N-(3-(4-((4-(1H-pyrazol-4-yl)phenyl)amino)-6-methoxyquinazolin-2-yl)phenyl)-2-morpholinoacetamide

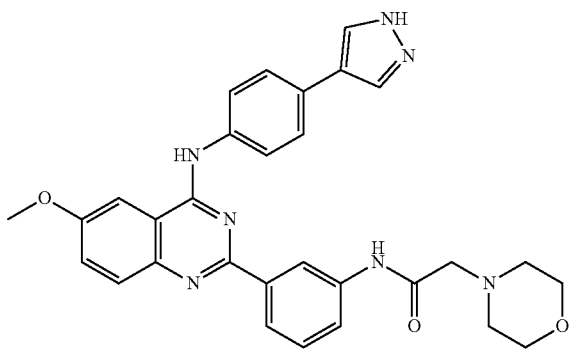 [SMILES: COc1ccc2nc(-c3cccc(NC(=O)CN4CCOCC4)c3)nc(Nc3ccc(-c4cn[nH]c4)cc3)c2c1]

Example 26A

N-(4-(1H-pyrazol-4-yl)phenyl)-2-chloro-6-methoxyquinazolin-4-amine

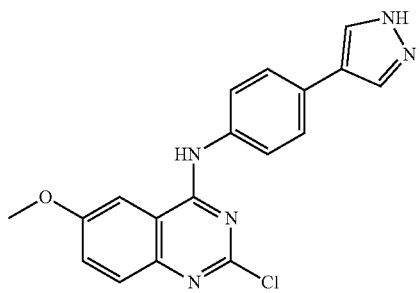 [SMILES: COc1ccc2nc(Cl)nc(Nc3ccc(-c4cn[nH]c4)cc3)c2c1]

A mixture of 2,4-dichloro-6-methoxyquinazoline (200 mg, 0.87 mmol), 4-(1H-pyrazol-4-yl)aniline (139 mg, 0.87 mmol) and diisopropylethylamine (0.30 mL, 1.75 mmol) in DMF (1.75 mL) was stirred at 100° C. for 5 h, cooled to rt, and diluted with water. The precipitate formed was collected by filtration and washed with water and dried to provide the title compound (300 mg, 98%). (ES+) m/e 352 (M+H)+.

Example 26B

N-(3-(4-((4-(1H-pyrazol-4-yl)phenyl)amino)-6-methoxyquinazolin-2-yl)phenyl)-2-morpholinoacetamide

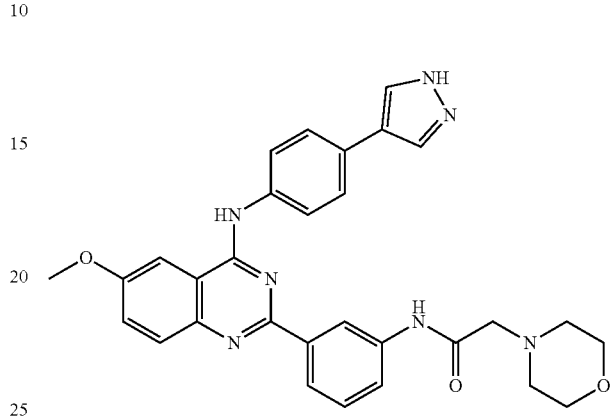

A mixture of N-(4-(1H-pyrazol-4-yl)phenyl)-2-chloro-6-methoxyquinazolin-4-amine (30 mg, 0.09 mmol), 2-morpholino-N-(3-(4,4,5,5-tetramethyl-1,3,2-dioxaborolan-2-yl)phenyl)acetamide (29 mg, 0.09 mmol), tetrakis(triphenylphosphine)palladium(0) (10 mg, 0.01 mmol), water (0.09 mL), saturated $Na_2CO_3$ (0.09 mL) and dioxane (0.9 mL) was heated in a microwave at 180° C. for 2 h. The mixture was concentrate to dryness and purified by reverse-phase HPLC to provide the title compound (20 mg, 44%). $^1$H NMR (500 MHz, DMSO-$d_6$) δ 10.91 (s, 1H), 10.42 (s, 1H), 8.35 (d, J=8.4 Hz, 2H), 8.14 (s, 2H), 8.09 (s, 1H), 7.90-7.88 (m, 3H), 7.79 (t, J=8.7 Hz, 4H), 7.64 (d, J=9.1 Hz, 1H), 4.24 (s, 2H), 3.85 (s, 3H), 3.84-4.00 (m, 4H), 3.45-3.31 (m, 4H). (ES+) m/e 536 (M+H)+.

Example 27

2-(3-(4-((4-(1H-Pyrazol-3-yl)phenyl)amino)-6-ethoxyquinazolin-2-yl)phenoxy)-N-(tert-butyl)acetamide

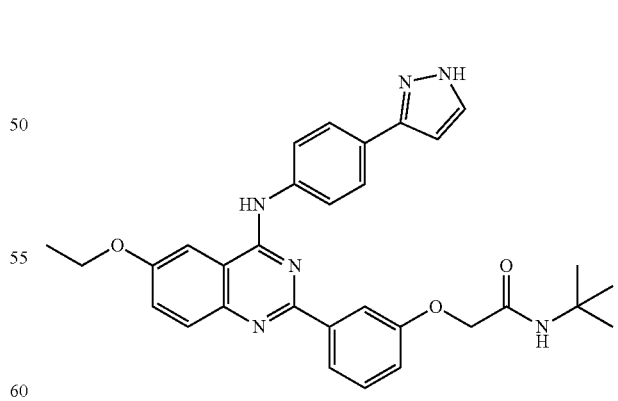

Into a 10 mL microwave vessel was added N-(tert-butyl)-2-(3-(4,4,5,5-tetramethyl-1,3,2-dioxaborolan-2-yl)phenoxy)acetamide (33.3 mg, 0.100 mmol), N-(4-(1H-pyrazol-3-yl)phenyl)-2-chloro-6-ethoxyquinazolin-4-amine (27.6 mg, 0.100 mmol), and Pd(PPh$_3$)$_4$ (11.6 mg, 0.0100 mmol). Then dioxane (1 mL), water (0.100 mL), and a solution of aqueous $Na_2CO_3$ (2M, 0.200 mmol, 0.100 mL) were added. The vessel was flushed with nitrogen and the vessel was irradiated at 180° C. for 2 h. After the reaction was cooled to rt, it was checked by LC-MS. The LC-MS of the reaction showed a peak that corresponded to the desired product mass. The mixture was transferred to a 20 mL vial with the aid of methanol and the solvent was removed in vacuo to give a residue. Then DMSO/MeOH (1.5 mL/0.2 mL) was added to the vial and the mixture was stirred for at least 30 min. The mixture was filtered through a 0.45 m syringe filter and subjected to HPLC purification (10% B/90% A to 100% B gradient where A is water (0.1% TFA) and B is ACN (0.1% TFA), 14 min gradient time and 17 min run time) to give 18.5 mg, 35%, of the title compound as a yellow solid. $^1$H NMR (500 MHz, DMSO-$d_6$) δ 8.12 (s, 1H), 8.01-7.88 (m, 7H), 7.77 (d, J=2.1 Hz, 1H), 7.67 (d, J=9.0 Hz, 1H), 7.57 (s, 1H), 7.53 (t, J=8.0 Hz, 1H), 7.18 (d, J=8.2 Hz, 1H), 6.79 (d, J=2.2 Hz, 1H), 4.52 (s, 3H), 4.28 (q, J=7.0 Hz, 2H), 1.47 (t, J=6.9 Hz, 3H), 1.30 (s, 9H). MS (ES+) m/e 537 (M+H)$^+$.

Example 28

2-(3-(4-((4-(1H-Pyrazol-3-yl)phenyl)amino)-6-ethoxyquinazolin-2-yl)phenoxy)-N-isopropylacetamide

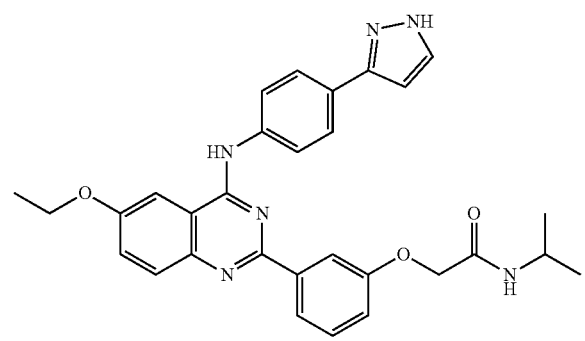 [SMILES: CCOc1ccc2nc(-c3cccc(OCC(=O)NC(C)C)c3)nc(Nc3ccc(-c4cc[nH]n4)cc3)c2c1]

Into a 10 mL microwave vessel was added N-isopropyl-2-(3-(4,4,5,5-tetramethyl-1,3,2-dioxaborolan-2-yl)phenoxy)acetamide (26.2 mg, 0.082 mmol), N-(4-(1H-pyrazol-3-yl)phenyl)-2-chloro-6-ethoxyquinazolin-4-amine (30 mg, 0.082 mmol), and Pd(PPh$_3$)$_4$ (9.5 mg, 0.0082 mmol). Then dioxane (0.820 mL), water (0.082 mL), and a solution of aqueous Na$_2$CO$_3$ (2M, 0.164 mmol, 0.082 mL) were added. The vessel was flushed with nitrogen and the vessel was irradiated at 180° C. for 2 h. After the reaction was cooled to rt, it was checked by LC-MS. The LC-MS of the reaction showed a peak that corresponded to the desired product mass. The mixture was transferred to a 20 mL vial with the aid of methanol and the solvent was removed in vacuo to give a residue. Then DMSO/MeOH (1.5 mL/0.2 mL) was added to the vial and the mixture was stirred for at least 30 min. The mixture was filtered through a 0.45 m syringe filter and subjected to HPLC purification (10% B/90% A to 100% B gradient where A is water (0.1% TFA) and B is ACN (0.1% TFA), 14 min gradient time and 17 min run time) to give 22.7 mg, 43%, of the title compound as a yellow solid. $^1$H NMR (500 MHz, DMSO-$d_6$) δ 10.52 (s, 1H), 8.20-7.44 (m, 13H), 7.20 (s, 1H), 6.79 (s, 1H), 4.56 (s, 2H), 4.28 (q, J=7.1 Hz, 2H), 4.05-3.85 (m, 1H), 1.61-1.37 (m, 3H), 1.09 (d, J=6.8 Hz, 6H). MS (ES+) m/e 523 (M+H)$^+$.

Example 29

2-(3-(4-((4-(1H-Pyrazol-4-yl)phenyl)amino)-6-fluoroquinazolin-2-yl)phenoxy)-N-(tert-butyl)acetamide

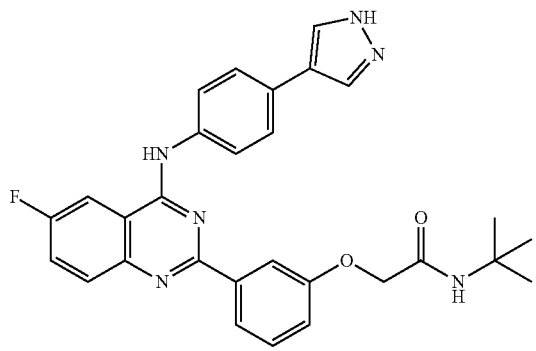 [SMILES: CC(C)(C)NC(=O)COc1cccc(-c2nc(Nc3ccc(-c4cn[nH]c4)cc3)c3cc(F)ccc3n2)c1]

Example 29A

N-(4-(1H-pyrazol-4-yl)phenyl)-2-chloro-6-fluoroquinazolin-4-amine

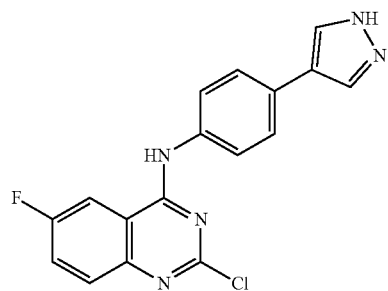 [SMILES: Fc1ccc2nc(Cl)nc(Nc3ccc(-c4cn[nH]c4)cc3)c2c1]

A mixture of 4-(1H-pyrazol-4-yl)aniline (120 mg, 0.75 mmol), 2,4-dichloro-6-fluoroquinazoline (164 mg, 0.75 mmol), and iPrNEt$_2$ (195 mg, 1.51 mmol) in DMF (2.51 mL) was stirred at 90° C. overnight, cooled to rt, diluted with water. The precipitate formed was collected by filtration and washed with water and dried in vacuo to provide the title compound (255 mg, 100%). MS (ES+) m/e 340 (M+H)$^+$.

Example 29B 2-(3-(4-((4-(1H-Pyrazol-4-yl)phenyl)amino)-6-fluoroquinazolin-2-yl)phenoxy)-N-(tert-butyl)acetamide

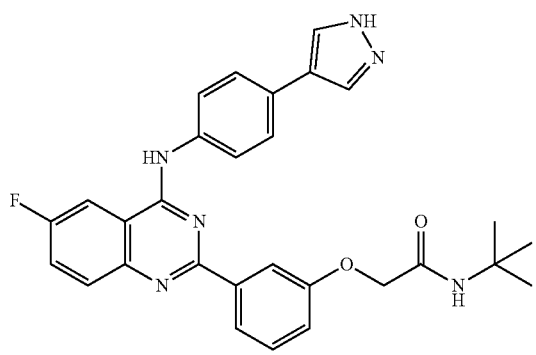 [SMILES: CC(C)(C)NC(=O)COc1cccc(-c2nc(Nc3ccc(-c4cn[nH]c4)cc3)c3cc(F)ccc3n2)c1]

To a 10 mL microwave vessel s was added N-(4-(1H-pyrazol-4-yl)phenyl)-2-chloro-6-fluoroquinazolin-4-amine (34.0 mg, 0.100 mmol), N-(tert-butyl)-2-(3-(4,4,5,5-tetramethyl-1,3,2-dioxaborolan-2-yl)phenoxy)acetamide (33.4 mg, 0.100 mmol), Pd(PPh$_3$)$_4$ (11.6 mg, 0.0100 mmol), and dioxane (2.1 mL). Then a solution of aqueous sodium carbonate (2M, 0.100 mL, 0.200 mmol) and water (0.100 mL) were added. The vessel was flushed with nitrogen then the vessel was irradiated at 180° C. for 2 h. After the reaction was cooled to rt, it was checked by LC-MS. LC-MS showed one major peak corresponding to the desired product mass. The reaction mixture was transferred to a 20 mL vial with the aid of methanol and the solvent was removed in vacuo to give a residue. The residue was stirred in DMSO/MeOH (1.5 mL/0.2 mL) for 30 min and the solution was filtered through a 0.45 m syringe filter. HPLC (10% B/90% A to 100% B gradient where A is water (0.1% TFA) and B is ACN (0.1% TFA), 14 min gradient time and 17 min run time) gave 8.9 mg, 14%, of the title compound as a yellow solid. $^1$H NMR (500 MHz, DMSO-d$_6$) δ $^1$H NMR (500 MHz, DMSO-d$_6$) δ 10.16 (s, 1H), 8.52 (dd, J=9.9, 2.8 Hz, 1H), 8.12 (s, 2H), 8.06-7.92 (m, 5H), 7.87 (td, J=9.3, 8.9, 2.7 Hz, 1H), 7.76 (d, J=8.6 Hz, 2H), 7.57 (s, 1H), 7.49 (t, J=7.9 Hz, 1H), 7.14 (dd, J=8.2, 2.6 Hz, 1H), 4.52 (s, 2H), 1.31 (s, 9H). MS (ES+) m/e 511 (M+H)$^+$.

Example 30

2-(3-(4-((4-(1H-Pyrazol-4-yl)phenyl)amino)-7-fluoroquinazolin-2-yl)phenoxy)-N-(tert-butyl)acetamide

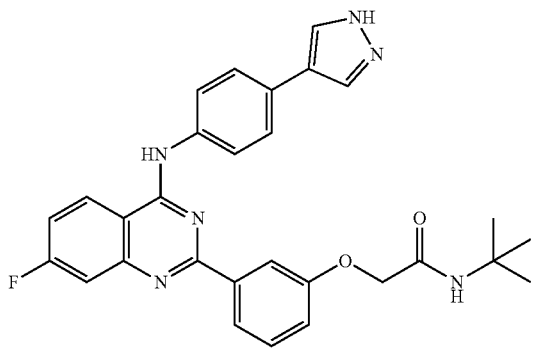 [SMILES: CC(C)(C)NC(=O)COc1cccc(-c2nc(Nc3ccc(-c4cn[nH]c4)cc3)c3ccc(F)cc3n2)c1]

Example 30A

N-(4-(1H-pyrazol-4-yl)phenyl)-2-chloro-7-fluoroquinazolin-4-amine

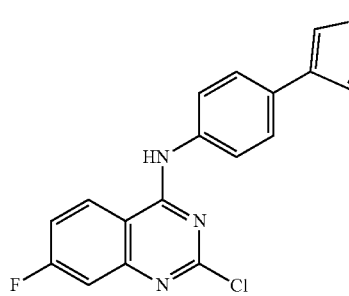

A mixture of 4-(1H-pyrazol-4-yl)aniline (120 mg, 0.75 mmol), 2,4-dichloro-7-fluoroquinazoline (164 mg, 0.75 mmol), and iPrNEt$_2$ (195 mg, 1.51 mmol) in DMF (2.51 mL) was stirred at 90° C. overnight, cooled to rt, diluted with water. The precipitate formed was collected by filtration and washed with water and dried in vacuo to provide the title compound (245 mg, 96%). MS (ES+) m/e 340 (M+H)$^+$.

Example 30B 2-(3-(4-((4-(1H-Pyrazol-4-yl)phenyl)amino)-7-fluoroquinazolin-2-yl)phenoxy)-N-(tert-butyl)acetamide

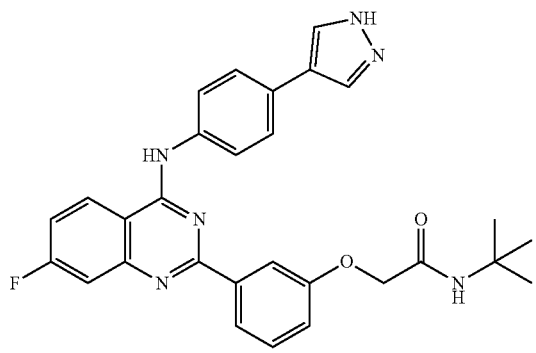 [SMILES: CC(C)(C)NC(=O)COc1cccc(-c2nc(Nc3ccc(-c4cn[nH]c4)cc3)c3ccc(F)cc3n2)c1]

To a 10 mL microwave vessel s was added N-(4-(1H-pyrazol-4-yl)phenyl)-2-chloro-7-fluoroquinazolin-4-amine (34.0 mg, 0.100 mmol), N-(tert-butyl)-2-(3-(4,4,5,5-tetramethyl-1,3,2-dioxaborolan-2-yl)phenoxy)acetamide (33.4 mg, 0.100 mmol), Pd(PPh$_3$)$_4$ (11.6 mg, 0.0100 mmol), and dioxane (2.1 mL). Then a solution of aqueous sodium carbonate (2M, 0.100 mL, 0.200 mmol) and water (0.100 mL) were added. The vessel was flushed with nitrogen then the vessel was irradiated at 180° C. for 2 h. After the reaction was cooled to rt, it was checked by LC-MS. LC-MS showed one major peak corresponding to the desired product mass. The reaction mixture was transferred to a 20 mL vial with the aid of methanol and the solvent was removed in vacuo to give a residue. The residue was stirred in DMSO/MeOH (1.5 mL/0.2 mL) for 30 min and the solution was filtered through a 0.45 m syringe filter. HPLC (10% B/90% A to 100% B gradient where A is water (0.1% TFA) and B is ACN (0.1% TFA), 14 min gradient time and 17 min run time) gave 8.9 mg, 14%, of the title compound as a yellow solid. $^1$H NMR (500 MHz, DMSO-d$_6$) δ 10.35 (s, 1H), 8.73 (dd, J=10.0, 5.6 Hz, 1H), 8.12 (s, 2H), 8.01 (t, J=6.2 Hz, 2H), 7.92 (d, J=8.1 Hz, 2H), 7.75 (d, J=8.1 Hz, 2H), 7.63 (d, J=9.2 Hz, 2H), 7.56 (s, 1H), 7.49 (t, J=7.9 Hz, 1H), 7.44-7.32 (m, 1H), 7.20-7.10 (m, 1H), 4.52 (s, 4H), 1.31 (s, 9H). MS (ES+) m/e 511 (M+H)$^+$.

Example 31

2-(3-(4-((4-(1H-Pyrazol-4-yl)phenyl)amino)-6-(2-methoxyethoxy)quinazolin-2-yl)phenoxy)-N-isopropylacetamide

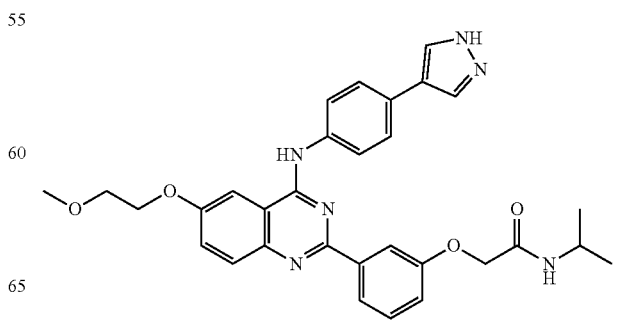

Example 31A

2-Methoxyethyl 5-(2-methoxyethoxy)-2-nitrobenzoate

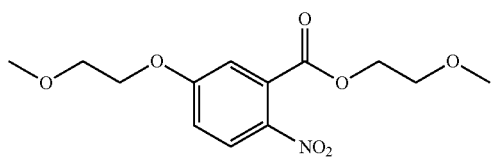

To a solution of 5-hydroxy-2-nitrobenzoic acid (915 mg, 5.00 mmol) in DMF (5.6 mL) was added $K_2CO_3$ (1.38 g, 10.00 mmol), and 2-bromomethyl methyl ether (2.08 g, 15 mmol, 1.41 mL). The reaction mixture was heated at 80° C. overnight. Tlc showed all of the starting benzoic acid was consumed and one new spot formed. No ion for the product was seen in the MS but there was one peak in the LC. The mixture was cooled to rt and poured into water. The aqueous mixture was extracted with EtOAc twice and the combined organic layers were washed with saturated NaCl, decanted from the drying agent, and concentrated in vacuo to give 1.45 g, 97%, of a yellow oil. The material is used as is in the next step.

Example 31B

2-Methoxyethyl 2-amino-5-(2-methoxyethoxy)benzoate

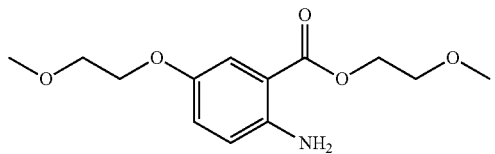

To a solution of 2-methoxyethyl 5-(2-methoxyethoxy)-2-nitrobenzoate (1.45 g, 4.84 mmol) in a 250 mL RBF in MeOH (10 mL) was added 10% Pd/C (~20 wt %). The flask was evacuated with house vacuum then filled with hydrogen. This process was done two more times then the reaction mixture was stirred under an atmosphere of hydrogen for 3 d after which LC-MS showed the reaction was complete. The mixture was filtered through a pad of Celite with MeOH to remove the catalyst. There yielded, after removal of the methanol, 1.17 g, 89%, of the desired product as a dark red oil. The product is used as is in the next step. MS (ES+) m/e 270 (M+H)$^+$.

Example 31C 6-(2-Methoxyethoxy)quinazoline-2,4(1H,3H)-dione

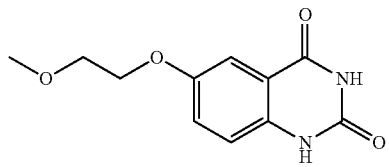 [SMILES: COCCOc1ccc2[nH]c(=O)[nH]c(=O)c2c1]

A mixture of 2-methoxyethyl 2-amino-5-(2-methoxyethoxy)benzoate (1.16 g, 4.31 mmol) and urea (3.88 g, 64.61 mmol, 15 eq.) was heated at 180° C. for 6 h after which LC-MS showed the reaction was complete. The cooled reaction mixture was diluted with water and the solid mass was broken up with a spatula then filtered and washed with water. The solid was then stirred in water for 2 h after which the solid was filtered and left on the filter overnight to dry using vacuum. The material was further dried in a desiccator for 2 d to give 852 mg, 84%, of a tan solid. This material is used as is in the next step. MS (ES+) m/e 237 (M+H)$^+$.

Example 31D 2,4-Dichloro-6-(2-methoxyethoxy)quinazoline

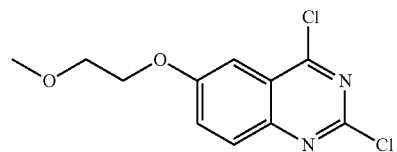 [SMILES: COCCOc1ccc2nc(Cl)nc(Cl)c2c1]

To a mixture of 6-(2-methoxyethoxy)quinazoline-2,4(1H, 3H)-dione (852 mg, 3.611 mmol) in POCl$_3$ (3.10 g, 20.23 mmol, 1.89 mL, 5.61 eq.) was added DIEA (466 mg, 3.61 mmol, 0.628 mL) then the reaction mixture was heated overnight at 90° C. after which LC-MS showed the reaction was complete. The mixture was cooled to rt and the excess solvent was removed in vacuo. The residue was cooled to 0° C. and cold water was added slowly to the stirred mixture. Approximately 50 mL of water was added to the mixture. Then, with continued cooling at 0° C., saturated NaHCO$_3$ was added slowly until the mixture was pH 9-10. The mixture was diluted with EtOAc and the biphasic mixture was shaken in a sep funnel and the layers were allowed to separate. It was noted a partial emulsion had formed (which had settled between the aqueous and organic layers). The aqueous layer was separated and the emulsion and organic layer was filtered through filter paper to leave behind a small amount of a tan solid. The aqueous layer in the filtrate was separated, combined with the main aqueous layer and extracted twice more with EtOAc. The combined organic layers were dried with sodium sulfate, decanted from the drying agent, and concentrated in vacuo to give 583 mg, 59%, of a dark yellow solid as the crude product. This material has a minor impurity in it but is used as is in the next reaction. MS (ES+) m/e 273/275/277 (M+H)$^+$.

Example 31E

N-(4-(1H-Pyrazol-4-yl)phenyl)-2-chloro-6-(2-methoxyethoxy)quinazolin-4-amine

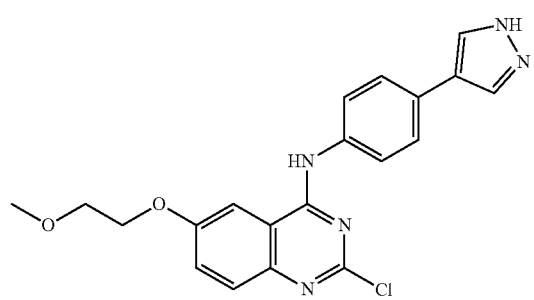 [SMILES: COCCOc1ccc2nc(Cl)nc(Nc3ccc(-c4cn[nH]c4)cc3)c2c1]

To a solution of 2,4-dichloro-6-(2-methoxyethoxy)quinazoline (273 mg, 1.00 mmol) and 4-(4-aminophenyl)pyrazole amine (159 mg, 1.00 mmol) in DMF (2 mL) in a 1-dram vial was added DIEA (258 mg, 2.00 mmol, 0.348 mL). The mixture was heated at 100° C. overnight. LC-MS showed one main peak corresponding to the desired product mass. The reaction mixture was cooled to rt and poured into water. The precipitate was filtered and washed with water. The resulting yellow solid was left to dry on the filter for 2 h to give 419 mg of crude product which was used as is in the next reaction. MS (ES+) m/e 396/398 (M+H)$^+$.

Example 31F 2-(3-(4-((4-(1H-Pyrazol-4-yl)phenyl)amino)-6-(2-methoxyethoxy)quinazolin-2-yl)phenoxy)-N-isopropylacetamide

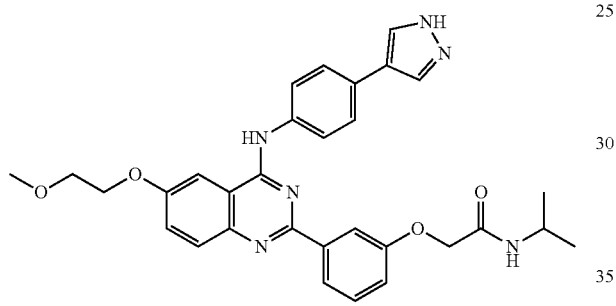

To N-(4-(1H-pyrazol-4-yl)phenyl)-2-chloro-6-(2-methoxyethoxy)quinazolin-4-amine (29.7 mg, 0.075 mmol), N-isopropyl-2-(3-(4,4,5,5-tetramethyl-1,3,2-dioxaborolan-2-yl)phenoxy)acetamide (24 mg, 0.075 mmol), and Pd(PPh$_3$)$_4$ (8.7 mg, 0.0075 mmol) in a 10 mL microwave vial was added dioxane (0.750 mL), a solution of aqueous sodium carbonate (2M, 0.075 mL, 0.15 mmol) and water (0.075 mL). The vessel was flushed with nitrogen then the vessel was irradiated at 180° C. for 2 h. After the reaction was cooled to rt, the reaction was checked by LC-MS. LC-MS showed one main peak for the reaction. The reaction mixture was transferred to a 20 mL vial with the aid of methanol. The solvent was removed in vacuo using a rotovap. The resulting residue was stirred in DMSO/MeOH (1.5 mL/0.2 mL) for 30 min then the mixture was filtered through a 45 mm syringe filter before HPLC. HPLC (10% B/90% A to 100% B gradient where A is water (0.1% TFA) and B is ACN (0.1% TFA), 14 min gradient time and 17 min run time) gave 9.5 mg, 19%, of the title compound as a yellow solid. $^1$H NMR (500 MHz, DMSO-d$_6$) δ 8.14 (s, 3H), 8.01-7.85 (m, 6H), 7.78 (d, J=8.2 Hz, 2H), 7.68 (d, J=8.5 Hz, 1H), 7.53 (t, J=7.9 Hz, 1H), 7.20 (d, J=7.8 Hz, 1H), 4.57 (s, 2H), 4.34 (t, J=4.4 Hz, 2H), 3.98 (dt, J=13.7, 7.0 Hz, 1H), 3.80 (t, J=4.6 Hz, 2H), 3.38 (s, 3H), 1.10 (d, J=6.7 Hz, 6H). $^1$H NMR (500 MHz, DMSO-d$_6$) δ. MS (ES+) m/e 553 (M+H)$^+$.

Example 32

2-(3-(4-((4-(1H-Pyrazol-4-yl)phenyl)amino)-6-propoxyquinazolin-2-yl)phenoxy)-N-isopropylacetamide

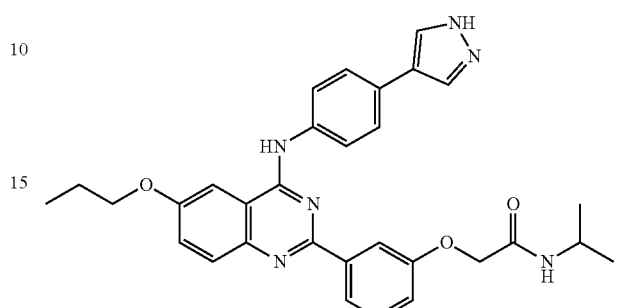

Example 32A

Propyl 2-nitro-5-propoxybenzoate

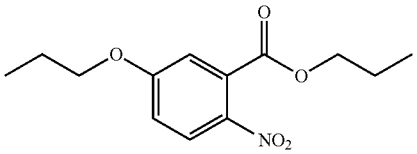 [SMILES: CCCOC(=O)c1cc(OCCC)ccc1[N+](=O)[O-]]

To a solution of 5-hydroxy-2-nitrobenzoic acid (5.00 g, 27.30 mmol) in DMF (31 mL) was added K$_2$CO$_3$ (7.54 g, 54.61 mmol), and iodopropane (13.92 g, 81.91 mmol, 8.0 mL). The reaction mixture was heated at 80° C. overnight. An LC-MS of the mixture at this point showed one major peak corresponding to the desired product (it doesn't ionize well in the MS) and a minor peak corresponding to the starting acid. Tlc (40% EtOAc/60% Hexanes) showed one major new spot was present and a minor amount of the starting acid. The mixture was cooled to rt and poured into EtOAc and diluted with water. The biphasic mixture was shaken in a seperatory funnel and the aqueous layer was separated. The aqueous layer was extracted with EtOAc twice and the combined organic layers were washed with saturated NaCl, decanted from the drying agent, and concentrated in vacuo to give 6.99 g, 96%, of a yellow oil. The material is used as is in the next step.

Example 32B

Propyl 2-amino-5-propoxybenzoate

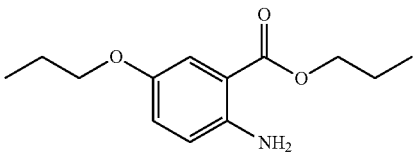 [SMILES: CCCOC(=O)c1cc(OCCC)ccc1N]

To a solution of each nitro compound (propyl 2-nitro-5-propoxybenzoate, 6.99 g, 26.16 mmol) in a 250 mL RBF in MeOH (52 mL) was added 10% Pd/C (1.4 g, ~20 wt %). The flask was evacuated with house vacuum then filled with hydrogen. This process was done two more times then the reaction mixture was stirred under an atmosphere of hydrogen for 3 d after which LC-MS showed the reaction was complete. The mixture was filtered through a pad of Celite with MeOH to remove the catalyst. There was still a significant amount of catalyst present in the filtered solution so it was concentrated in vacuo to remove most of the methanol and it was filtered through another pad of Celite. There yielded, after removal of the methanol in vacuo, 5.88 g, 95%, of the crude product as a dark red oil. The product is used as is in the next step. MS (ES+) m/e 238 (M+H)$^+$.

Example 32C

6-Propoxyquinazoline-2,4(1H,3H)-dione

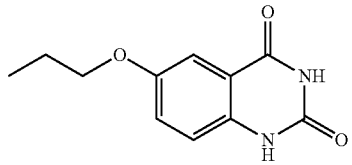 [SMILES: CCCOc1ccc2[nH]c(=O)[nH]c(=O)c2c1]

A mixture of propyl 2-amino-5-propoxybenzoate (2.59 g, 10.91 mmol) and urea (9.83 g, 163.72 mmol, 15 eq.) was heated at 180° C. for 4 h after which LC-MS showed a significant amount of the starting aniline present as well as the desired product. The mixture was heated further for 3 h after which LC-MS showed one main peak for the desired product and a very small amount of the aniline remaining. The mixture was cooled to rt and water was added. The reaction mixture had turned into a solid mass which had to be broken up by a spatula. After it was broken up, a fine precipitate had formed and much of the solid had dissolved into solution. The resulting mixture was filtered and washed with water. The filter cake was then stirred in water for 2 h after which it was filtered and dried on the filter for 3 d under vacuum. The material was further dried in a desiccator for two days to give 2.71 g, 113%, of a tan solid. The solid is used as is in the next step. MS (ES+) m/e 221 (M+H)$^+$.

Example 32D 2,4-Dichloro-6-propoxyquinazoline

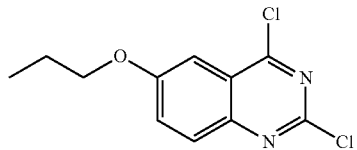 [SMILES: CCCOc1ccc2nc(Cl)nc(Cl)c2c1]

To a mixture of 6-propoxyquinazoline-2,4(1H,3H)-dione (1.10 g, 5.00 mmol) in POCl$_3$ (4.30 g, 28.05 mmol, 2.61 mL, 5.61 eq.) in a 100 mL RBF was added DIEA (646 mg, 5.00 mmol, 0.871 mL) then the reaction mixture was heated overnight at 90° C. after which LC-MS showed the reaction was complete. The reaction mixture was cooled to 0° C. then water (50 mL, cooled to below 10° C.) was added slowly with good stirring. Then saturated NaHCO$_3$ was added to basify the mixture to pH 9-10. The mixture was diluted with EtOAc and shaken in a sep funnel. A partial emulsion formed and the emulsion was vacuum filtered through filter paper. The aqueous layer was separated and extracted twice more with EtOAc. The combined organic layers were dried over sodium sulfate, decanted from the drying agent, and concentrated in vacuo to give 719 mg, 56%, of a tan solid that is used in the next step as is. MS (ES+) m/e 258/260/262 (M+H)$^+$.

Example 32E

N-(4-(1H-Pyrazol-4-yl)phenyl)-2-chloro-6-propoxy-quinazolin-4-amine

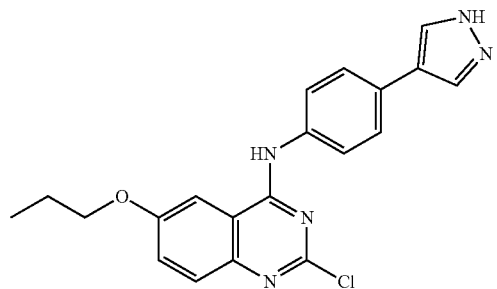 [SMILES: CCCOc1ccc2nc(Cl)nc(Nc3ccc(-c4cn[nH]c4)cc3)c2c1]

To a solution of 2,4-dichloro-6-propoxyquinazoline (257 mg, 1.00 mmol) and 4-(4-aminophenyl)pyrazole amine (159 mg, 1.00 mmol) in DMF (2 mL) in a 1-dram vial was added DIEA (258 mg, 2.00 mmol, 0.348 mL). The mixture was heated at 100° C. overnight. LC-MS showed one main peak corresponding to the desired product mass. The reaction mixture was cooled to rt and poured into water. The precipitate was filtered and washed with water. The resulting yellow solid was left to dry on the filter for 2 d to give 348 mg, 92%, of crude product which was used as is in the next reaction. MS (ES+) m/e 380/382 (M+H)$^+$.

Example 32F 2-(3-(4-((4-(1H-Pyrazol-4-yl)phenyl)amino)-6-propoxyquinazolin-2-yl)phenoxy)-N-isopropylacetamide

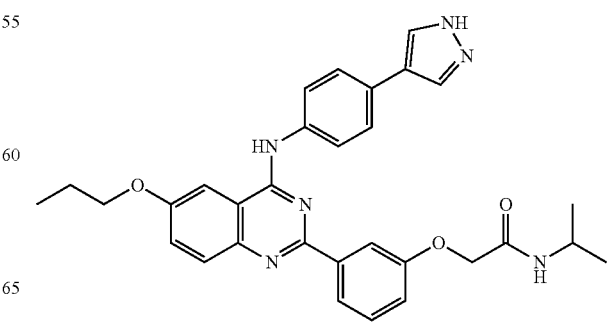

To N-(4-(1H-pyrazol-4-yl)phenyl)-2-chloro-6-propoxy-quinazolin-4-amine (28.5 mg, 0.075 mmol), N-isopropyl-2-(3-(4,4,5,5-tetramethyl-1,3,2-dioxaborolan-2-yl)phenoxy)acetamide (24 mg, 0.075 mmol), and Pd(PPh$_3$)$_4$ (8.7 mg, 0.0075 mmol) in a 10 mL microwave vial was added dioxane (0.750 mL), a solution of aqueous sodium carbonate (2M, 0.075 mL, 0.15 mmol) and water (0.075 mL). The vessel was flushed with nitrogen then the vessel was irradiated at 180° C. for 2 h. After the reaction was cooled to rt, the reaction was checked by LC-MS. LC-MS showed one main peak for the reaction. The reaction mixture was transferred to a 20 mL vial with the aid of methanol. The solvent was removed in vacuo using a rotovap. The resulting residue was stirred in DMSO/MeOH (1.5 mL/0.2 mL) for 30 min then the mixture was filtered through a 45 mm syringe filter before HPLC. HPLC (10% B/90% A to 100% B gradient where A is water (0.1% TFA) and B is ACN (0.1% TFA), 14 min gradient time and 17 min run time) gave 13.9 mg, 28%, of the compound as a yellow solid. $^1$H NMR (500 MHz, DMSO-d$_6$) δ $^1$H NMR (500 MHz, DMSO-d$_6$) δ 8.12 (d, J=18.2 Hz, 3H), 8.01-7.84 (m, 7H), 7.78 (d, J=8.2 Hz, 2H), 7.67 (d, J=8.8 Hz, 1H), 7.52 (d, J=7.4 Hz, 1H), 7.20 (d, J=8.0 Hz, 1H), 4.57 (s, 2H), 4.17 (t, J=6.6 Hz, 2H), 4.03-3.93 (m, 1H), 1.87 (q, J=7.0 Hz, 2H), 1.10 (d, J=6.8 Hz, 6H), 1.07 (d, J=7.4 Hz, 3H). MS (ES+) m/e 537 (M+H)$^+$.

Example 33

2-(3-(4-((4-(1H-pyrazol-4-yl)phenyl)amino)-6-fluoroquinazolin-2-yl)phenoxy)-N-isopropylacetamide

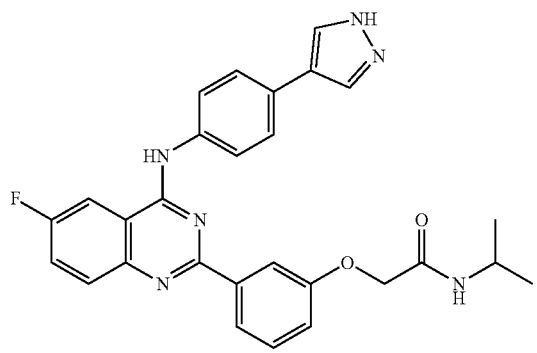 [SMILES: CC(C)NC(=O)COc1cccc(-c2nc(Nc3ccc(-c4cn[nH]c4)cc3)c3cc(F)ccc3n2)c1]

A mixture of N-(4-(1H-pyrazol-4-yl)phenyl)-2-chloro-6-fluoroquinazolin-4-amine (34 mg, 0.10 mmol), N-isopropyl-2-(3-(4,4,5,5-tetramethyl-1,3,2-dioxaborolan-2-yl)phenoxy)acetamide (32 mg, 0.10 mmol), Pd(PPh$_3$)$_4$ (11 mg, 0.01 mmol), 1M Na$_2$CO$_3$ solution (0.2 mL), and water (1.0 mL) was heated in a microwave reactor at 180° C. for 2 h. The mixture was concentrated to dryness, redissolved in DMSO, and purified by reverse-phase HPLC to provide the title compound (9.8 mg, 16%). $^1$H NMR (500 MHz, DMSO-d$_6$) δ 10.09 (s, 1H), 8.51 (dd, J=10.0, 2.8 Hz, 1H), 8.12 (s, 2H), 8.05 (d, J=6.3 Hz, 2H), 7.98 (dd, J=13.4, 8.3 Hz, 4H), 7.85 (td, J=8.9, 2.7 Hz, 1H), 7.75 (d, J=8.3 Hz, 2H), 7.49 (t, J=8.1 Hz, 1H), 7.15 (dd, J=8.1, 2.5 Hz, 1H), 4.56 (s, 2H), 4.00 (dq, J=13.6, 6.8 Hz, 1H), 1.11 (d, J=6.6 Hz, 6H). MS (ES+) m/e 497 (M+H)$^+$.

Example 34

2-(3-(4-((4-(1H-Pyrazol-4-yl)phenyl)amino)-7-fluoroquinazolin-2-yl)phenoxy)-N-isopropylacetamide

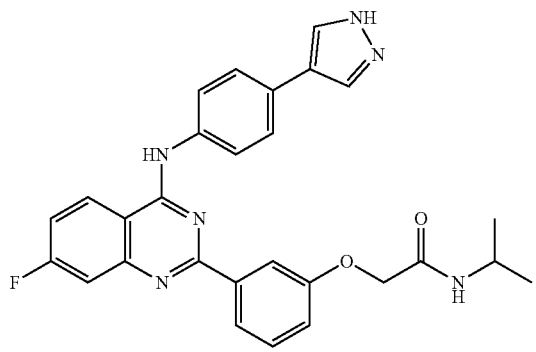 [SMILES: CC(C)NC(=O)COc1cccc(-c2nc(Nc3ccc(-c4cn[nH]c4)cc3)c3ccc(F)cc3n2)c1]

A mixture of N-(4-(1H-pyrazol-4-yl)phenyl)-2-chloro-7-fluoroquinazolin-4-amine (34 mg, 0.10 mmol), N-isopropyl-2-(3-(4,4,5,5-tetramethyl-1,3,2-dioxaborolan-2-yl)phenoxy)acetamide (32 mg, 0.10 mmol), Pd(PPh$_3$)$_4$ (11 mg, 0.01 mmol), 1M Na$_2$CO$_3$ solution (0.2 mL), and water (1.0 mL) was heated in a microwave reactor at 180° C. for 2 h. The mixture was concentrated to dryness, redissolved in DMSO, and purified by reverse-phase HPLC to provide the title compound (4.1 mg, 7%). $^1$H NMR (500 MHz, DMSO-d$_6$) δ 8.72 (dd, J=9.0, 5.9 Hz, 1H), 8.12 (s, 2H), 8.04 (d, J=6.6 Hz, 2H), 7.99 (d, J=8.1 Hz, 1H), 7.94 (d, J=8.2 Hz, 2H), 7.75 (d, J=8.3 Hz, 2H), 7.62 (dq, J=13.4, 6.3, 4.4 Hz, 2H), 7.49 (t, J=8.1 Hz, 1H), 7.16 (dd, J=8.3, 2.4 Hz, 1H), 4.56 (s, 2H), 3.99 (dp, J=13.8, 6.8 Hz, 1H), 1.11 (d, J=6.6 Hz, 6H). MS (ES+) m/e 497 (M+H)$^+$.

Example 35

(S)-2-(3-(4-((4-(1H-Pyrazol-4-yl)phenyl)amino)-6-ethoxyquinazolin-2-yl)phenoxy)-N-(sec-butyl)acetamide

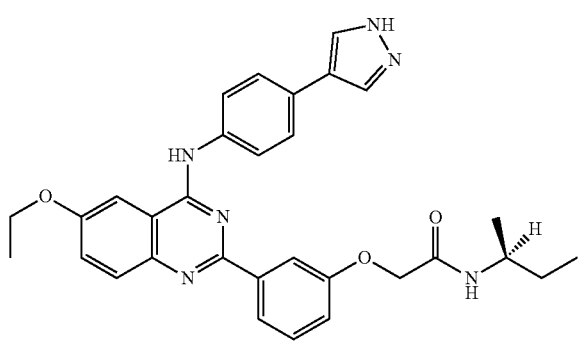 [SMILES: CCOc1ccc2nc(-c3cccc(OCC(=O)N[C@@H](C)CC)c3)nc(Nc3ccc(-c4cn[nH]c4)cc3)c2c1]

Example 35A

N-(4-(1H-Pyrazol-4-yl)phenyl)-2-chloro-6-ethoxy-quinazolin-4-amine

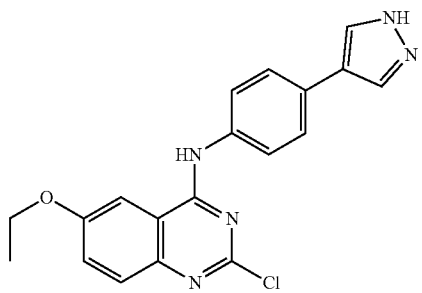 [SMILES: CCOc1ccc2nc(Cl)nc(Nc3ccc(-c4cn[nH]c4)cc3)c2c1]

A mixture of 2,4-dichloro-6-ethoxyquinazoline (328 mg, 1.60 mmol), 4-(1H-pyrazol-4-yl)aniline (255 mg, 1.60 mmol), and diisopropylethylamine (413 mg, 3.2 mmol) in DMF (3.20 mL) was heated at 100° C. for 3 h. LCMS and TLC showed the reaction was complete. The mixture was diluted with water. The precipitate formed was filtered and washed with water, and dried to provide the title compound as a yellow solid (420 mg, 72%). MS (ES+) m/e 366 (M+H)$^+$.

Example 35B (S)—N-(sec-Butyl)-2-chloroacetamide

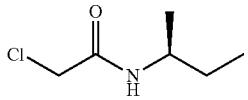

To (S)-butan-2-amine (499 mg, 6.82 mmol) in DCM (6 mL) at 0° C. was added 2-chloroacetyl chloride (350 mg, 3.10 mmol) in DCM (4 mL) dropwise. The mixture was stirred at 0° C. for 30 min followed by 2 h at rt. The mixture was diluted with EtOAc, washed with 1N HCl, water, NaHCO3 solution, and brine, dried over Na$_2$SO4, and concentrated in vacuo to provide the title compound as a white solid (361 mg, 78%). MS (ES+) m/e 150 (M+H)$^+$.

Example 35C (S)—N-(sec-butyl)-2-(3-(4,4,5,5-tetramethyl-1,3,2-dioxaborolan-2-yl)phenoxy)acetamide

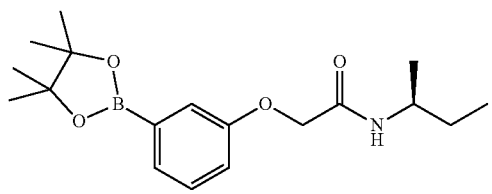 [SMILES: CC[C@H](C)NC(=O)COc1cccc(B2OC(C)(C)C(C)(C)O2)c1]

A mixture of (S)—N-(sec-butyl)-2-chloroacetamide (202 mg, 1.35 mmol), 3-(4,4,5,5-tetramethyl-1,3,2-dioxaborolan-2-yl)phenol (270 mg, 1.23 mmol), and K$_2$CO$_3$ (399 mg, 2.45 mmol) in DMF (4.09 mL) was heated at 65° C. overnight. The mixture was cooled to rt, diluted with water, and extracted with EtOAc. The organic layer was washed with water (3×) and brine, and dried over Na$_2$SO$_4$ and concentrated in vacuo to provide the title compound as a white solid (256 mg, 79%). MS (ES+) m/e 334 (M+H)$^+$.

Example 35D (S)-2-(3-(4-((4-(1H-Pyrazol-4-yl)phenyl)amino)-6-ethoxyquinazolin-2-yl)phenoxy)-N-(sec-butyl)acet-amide

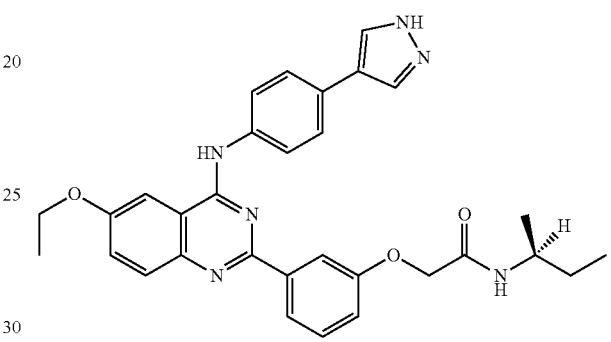

To a 10 mL microwave vessel was added 2-chloro-6-ethoxy-N-(4-(1-(tetrahydro-2H-pyran-2-yl)-1H-pyrazol-4-yl)phenyl)quinazolin-4-amine (35.8 mg, 0.080 mmol), (S)—N-(sec-butyl)-2-(3-(4,4,5,5-tetramethyl-1,3,2-dioxaborolan-2-yl)phenoxy)acetamide (26.51 mg, 0.080 mmol), Pd(PPh$_3$)$_4$ (9.2 mg, 0.0080 mmol), and dioxane (0.800 mL). Then a solution of aqueous sodium carbonate (2M, 0.080 mL, 0.160 mmol) and water (0.080 mL) were added. The vessel was flushed with nitrogen then the vessel was irradiated at 180° C. for 2 h. After the reaction was cooled to rt, the reaction was checked by LC-MS. LC-MS showed one major peak corresponding to the desired product mass for the THP protected product. The reaction mixture was transferred to a 20 mL vial with the aid of methanol and the solvent was removed in vacuo to give a residue. To the residue was added DCM (1.4 mL) and TFA (0.457 mL). The mixture was stirred for 1.5 h after LC-MS showed the deprotection was complete. The solvent was removed in vacuo then the resulting residue was stirred in DMSO/MeOH (1.5 mL/0.2 mL) for 30 min and filtered through a 45 mm syringe filter. HPLC (10% B/90% A to 100% B gradient where A is water (0.1% TFA) and B is ACN (0.1% TFA), 14 min gradient time and 17 min run time) gave 22.2 mg, 43%, of the title compound as a yellow-orange solid. $^1$H NMR (500 MHz, DMSO-d$_6$) δ 10.62 (s, 1H), 8.12 (d, J=14.6 Hz, 3H), 8.00-7.83 (m, 6H), 7.78 (d, J=8.4 Hz, 2H), 7.66 (d, J=9.2 Hz, 1H), 7.53 (t, J=8.2 Hz, 1H), 7.21 (s, 1H), 4.59 (s, 2H), 4.27 (q, J=7.1 Hz, 2H), 3.79 (m, 1H), 1.56-1.31 (m, 5H), 1.06 (d, J=6.7 Hz, 3H), 0.80 (t, J=7.4 Hz, 3H). MS (ES+) m/e 537 (M+H)$^+$. [α]$^{25°}$$_D$=+2.67 (c=0.16 in MeOH).

Example 36

(R)-2-(3-(4-((4-(1H-Pyrazol-4-yl)phenyl)amino)-6-ethoxyquinazolin-2-yl)phenoxy)-N-(sec-butyl)acetamide

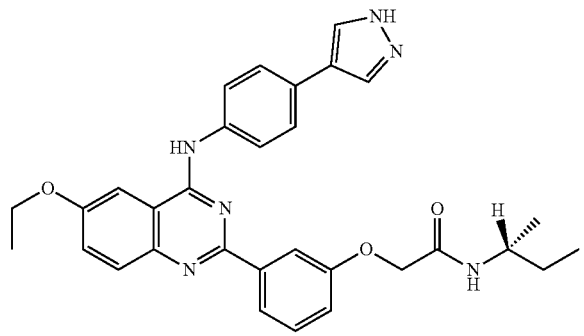 [SMILES: CCOc1ccc2nc(-c3cccc(OCC(=O)N[C@H](C)CC)c3)nc(Nc3ccc(-c4cn[nH]c4)cc3)c2c1]

Example 36A (R)—N-(sec-Butyl)-2-chloroacetamide

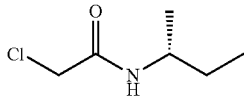

To (R)-butan-2-amine (499 mg, 6.82 mmol) in DCM (6 mL) at 0° C. was added 2-chloroacetyl chloride (350 mg, 3.10 mmol) in DCM (4 mL) dropwise. The mixture was stirred at 0° C. for 30 min followed by 2 h at rt. The mixture was diluted with EtOAc, washed with 1N HCl, water, NaHCO3 solution, and brine, dried over Na₂SO4, and concentrated in vacuo to provide the title compound as a white solid (368 mg, 78%). MS (ES+) m/e 150 (M+H)⁺.

Example 36B (R)—N-(sec-butyl)-2-(3-(4,4,5,5-tetramethyl-1,3,2-dioxaborolan-2-yl)phenoxy)acetamide

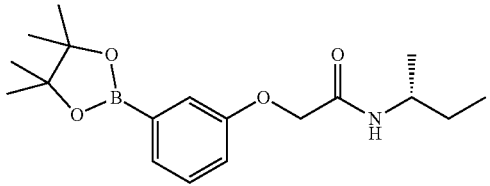 [SMILES: CC[C@@H](C)NC(=O)COc1cccc(B2OC(C)(C)C(C)(C)O2)c1]

A mixture of (R)—N-(sec-butyl)-2-chloroacetamide (135 mg, 0.9 mmol), 3-(4,4,5,5-tetramethyl-1,3,2-dioxaborolan-2-yl)phenol (180 mg, 1.42 mmol), and K₂CO₃ (226 mg, 1.64 mmol) in DMF (2.7 mL) was heated at 65° C. overnight. The mixture was cooled to rt, diluted with water, and extracted with EtOAc. The organic layer was washed with water (3×) and brine, and dried over Na₂SO₄ and concentrated in vacuo to provide the title compound as a white solid (152 mg, 70%). MS (ES+) m/e 334 (M+H)⁺.

Example 36C (R)-2-(3-(4-((4-(1H-Pyrazol-4-yl)phenyl)amino)-6-ethoxyquinazolin-2-yl)phenoxy)-N-(sec-butyl)acetamide

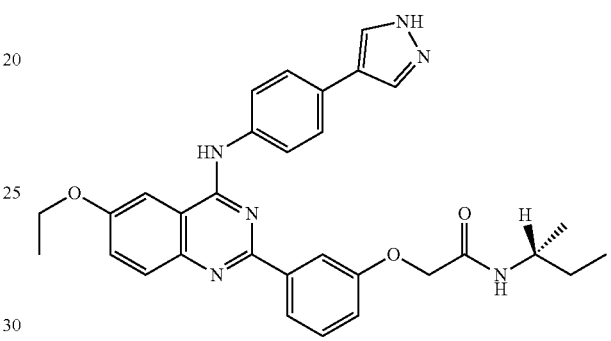

To a 10 mL microwave vessel was added 2-chloro-6-ethoxy-N-(4-(1-(tetrahydro-2H-pyran-2-yl)-1H-pyrazol-4-yl)phenyl)quinazolin-4-amine (35.8 mg, 0.080 mmol), (R)—N-(sec-butyl)-2-(3-(4,4,5,5-tetramethyl-1,3,2-dioxaborolan-2-yl)phenoxy)acetamide (26.51 mg, 0.080 mmol), Pd(PPh₃)₄ (9.2 mg, 0.0080 mmol), and dioxane (0.800 mL). Then a solution of aqueous sodium carbonate (2M, 0.080 mL, 0.160 mmol) and water (0.080 mL) were added. The vessel was flushed with nitrogen then the vessel was irradiated at 180° C. for 2 h. After the reaction was cooled to rt, the reaction was checked by LC-MS. LC-MS showed one major peak corresponding to the desired product mass for the THP protected product. The reaction mixture was transferred to a 20 mL vial with the aid of methanol and the solvent was removed in vacuo to give a residue. To the residue was added DCM (1.4 mL) and TFA (0.457 mL). The mixture was stirred for 1.5 h after LC-MS showed the deprotection was complete. The solvent was removed in vacuo then the resulting residue was stirred in DMSO/MeOH (1.5 mL/0.2 mL) for 30 min and filtered through a 45 mm syringe filter. HPLC (10% B/90% A to 100% B gradient where A is water (0.1% TFA) and B is ACN (0.1% TFA), 14 min gradient time and 17 min run time) gave 20.5 mg, 40%, of the title compound as an orange solid. ¹H NMR (500 MHz, DMSO-d₆) δ 10.62 (s, 1H), 8.13 (d, J=12.3 Hz, 3H), 7.98-7.84 (m, 6H), 7.82-7.75 (m, 2H), 7.67 (d, J=9.2 Hz, 1H), 7.54 (t, J=8.2 Hz, 1H), 7.22 (d, J=8.2 Hz, 1H), 4.59 (s, 2H), 4.27 (q, J=6.9 Hz, 2H), 3.79 (dt, J=14.3, 7.1 Hz, 1H), 1.54-1.38 (m, 5H), 1.06 (d, J=6.7 Hz, 3H), 0.80 (t, J=7.4 Hz, 3H). ¹H NMR (500 MHz, DMSO-d₆) δ. MS (ES+) m/e 537 (M+H)⁺. [α]²⁵ ᶜD=−1.49 (c=0.15 in MeOH).

Example 37

2-(3-(4-((4-(1H-Pyrazol-4-yl)phenyl)amino)-6-propoxyquinazolin-2-yl)phenoxy)-N-(tert-butyl)acetamide

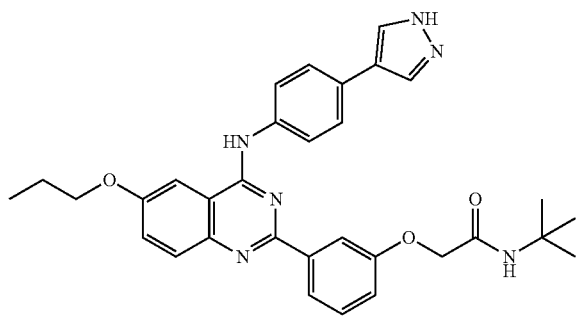 [SMILES: CCCOc1ccc2nc(-c3cccc(OCC(=O)NC(C)(C)C)c3)nc(Nc3ccc(-c4cn[nH]c4)cc3)c2c1]

To N-(tert-butyl)-2-(3-(4,4,5,5-tetramethyl-1,3,2-dioxaborolan-2-yl)phenoxy)acetamide (33.3 mg, 0.10 mmol) in a 10-mL microwave vessel was added a N-(4-(1H-pyrazol-4-yl)phenyl)-2-chloro-6-propoxyquinazolin-4-amine (38 mg, 0.100 mmol), Pd(PPh$_3$)$_4$ (11.6 mg, 0.010 mmol), and dioxane (1 mL). Then a solution of aqueous sodium carbonate (2M, 0.100 mL, 0.20 mmol) and water (0.100 mL) was added to μ μ the vial. The vial was flushed with nitrogen then irradiated at 180° C. for 2 h. After the reactions were cooled to rt, it was checked by LC-MS. The LC-MS showed the desired product mass was present in the reaction. The reaction mixture was transferred to a 20 mL vial with the aid of methanol. The solvent was removed in vacuo using a rotovap. The resulting residue was stirred in DMSO/MeOH (1.5 mL/0.2 mL) for 30 min then the mixture was filtered through a 0.45 m syringe filter before HPLC. HPLC (10% B/90% A to 100% B gradient where A is water (0.1% TFA) and B is ACN (0.1% TFA), 14 min gradient time and 17 min run time) gave 7.7 mg, 12%, of the title product as a yellow-orange solid. $^1$H NMR (500 MHz, DMSO-d$_6$) δ 10.61 (s, 1H), 8.12 (d, J=14.1 Hz, 3H), 7.98-7.84 (m, 5H), 7.78 (d, J=8.2 Hz, 2H), 7.67 (d, J=9.0 Hz, 1H), 7.57 (s, 1H), 7.52 (t, J=7.8 Hz, 1H), 7.18 (d, J=8.1 Hz, 1H), 4.53 (s, 2H), 4.17 (t, J=6.6 Hz, 2H), 1.87 (h, J=7.1 Hz, 3H), 1.30 (s, 9H), 1.08 (t, J=7.4 Hz, 3H). MS (ES+) m/e 551 (M+H)$^+$.

Example 38

2-(3-(4-((4-(1H-Pyrazol-4-yl)phenyl)amino)-6-(2-fluoroethoxy)quinazolin-2-yl)phenoxy)-N-(tert-butyl)acetamide

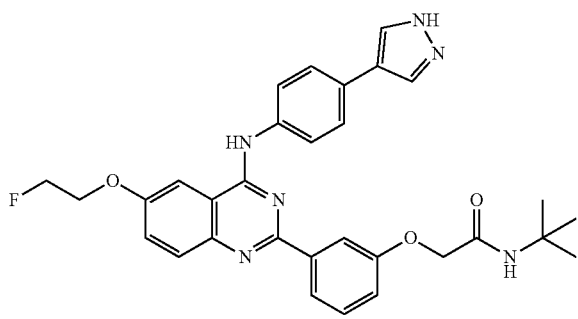 [SMILES: CC(C)(C)NC(=O)COc1cccc(-c2nc(Nc3ccc(-c4cn[nH]c4)cc3)c3cc(OCCF)ccc3n2)c1]

To N-(tert-butyl)-2-(3-(4,4,5,5-tetramethyl-1,3,2-dioxaborolan-2-yl)phenoxy)acetamide (33.3 mg, 0.10 mmol) in a 10-mL microwave vessel was added N-(4-(1H-pyrazol-4-yl)phenyl)-2-chloro-6-(2-fluoroethoxy)quinazolin-4-amine (38.3 mg, 0.100 mmol), Pd(PPh$_3$)$_4$ (11.6 mg, 0.010 mmol), and dioxane (1 mL). Then a solution of aqueous sodium carbonate (2M, 0.100 mL, 0.20 mmol) and water (0.100 mL) was added to the vial. The vial was flushed with nitrogen then irradiated at 180° C. for 2 h. After the reactions were cooled to rt, it was checked by LC-MS. The LC-MS showed the desired product mass was present in the reaction. The reaction mixture was transferred to a 20 mL vial with the aid of methanol. The solvent was removed in vacuo using a rotovap. The resulting residue was stirred in DMSO/MeOH (1.5 mL/0.2 mL) for 30 min then the mixture was filtered through a 0.45 m syringe filter before HPLC. HPLC (10% B/90% A to 100% B gradient where A is water (0.1% TFA) and B is ACN (0.1% TFA), 14 min gradient time and 17 min run time) gave 5.2 mg, 8%, of the title product as a yellow-orange solid. $^1$H NMR (500 MHz, DMSO-d$_6$) δ 10.59 (s, 1H), 8.15 (d, J=13.5 Hz, 3H), 7.94 (d, J=7.4 Hz, 3H), 7.89 (d, J=8.2 Hz, 2H), 7.79 (d, J=8.3 Hz, 2H), 7.72 (d, J=9.0 Hz, 1H), 7.57 (s, 1H), 7.53 (t, J=7.9 Hz, 1H), 7.19 (d, J=8.2 Hz, 1H), 4.95 (t, J=3.7 Hz, 1H), 4.85 (t, J=3.8 Hz, 1H), 4.52 (d, J=5.9 Hz, 3H), 4.47-4.41 (m, 1H), 1.30 (s, 9H). $^1$H NMR (500 MHz, DMSO-d$_6$) δ. MS (ES+) m/e 555 (M+H)$^+$.

Example 39

2-(3-(4-((4-(1H-Pyrazol-4-yl)phenyl)amino)-6-(2-methoxyethoxy)quinazolin-2-yl)phenoxy)-N-(tert-butyl)acetamide

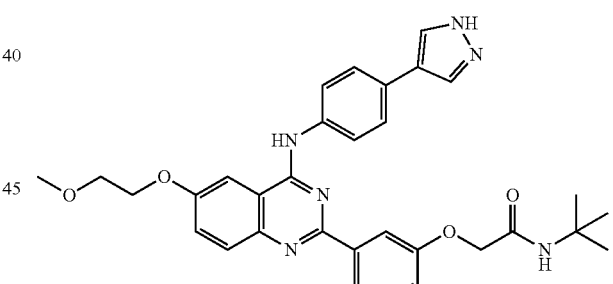

To N-(tert-butyl)-2-(3-(4,4,5,5-tetramethyl-1,3,2-dioxaborolan-2-yl)phenoxy)acetamide (33.3 mg, 0.10 mmol) in a 10-mL microwave vessel was added N-(4-(1H-pyrazol-4-yl)phenyl)-2-chloro-6-(2-methoxyethoxy)quinazolin-4-amine (39.5 mg, 0.100 mmol), Pd(PPh$_3$)$_4$ (11.6 mg, 0.010 mmol), and dioxane (1 mL). Then a solution of aqueous sodium carbonate (0.100 mL, 0.20 mmol, 2M) and water (0.10 mL) was added. The vessel was flushed with nitrogen then irradiated at 180° C. for 2 h. After the reaction was cooled to rt, it was checked by LC-MS. The LC-MS showed the desired product mass was present. The reaction mixture was transferred to a 20 mL vial with the aid of methanol. The solvent was removed in vacuo using a rotovap. The resulting residue was stirred in DMSO/MeOH (1.5 mL/0.2 mL) for 30 min then the mixture was filtered through a 0.45 mm syringe filter before HPLC. HPLC (10% B/90% A to 100% B gradient where A is water (0.1% TFA) and B is ACN (0.1% TFA), 14 min gradient time and 17 min run time) gave 9.2 mg, 14%, of the title compound as a yellow-orange solid. $^1$H NMR (500 MHz, DMSO-$d_6$) δ 10.69 (s, 1H), 8.14 (s, 3H), 7.91 (dd, J=27.6, 8.3 Hz, 5H), 7.78 (d, J=8.3 Hz, 2H), 7.70 (s, 1H), 7.55 (d, J=18.0 Hz, 2H), 7.20 (s, 1H), 4.53 (b, 2H), 4.34 (s, 2H), 3.80 (b, 2H), 3.38 (b, 3H), 1.30 (s, 9H). MS (ES+) m/e 567 (M+H)$^+$.

Example 40

2-(3-(4-((4-(1H-Pyrazol-4-yl)phenyl)amino)-6-(2-fluoroethoxy)quinazolin-2-yl)phenoxy)-N-isopropylacetamide

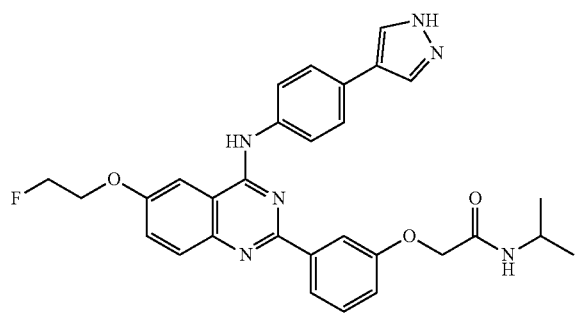

Example 40A

2-Fluoroethyl 5-(2-fluoroethoxy)-2-nitrobenzoate

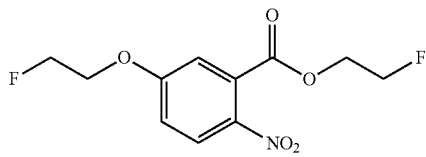 [SMILES: O=C(OCCF)c1cc(OCCF)ccc1[N+](=O)[O-]]

To a solution of 5-hydroxy-2-nitrobenzoic acid in a 100 mL RBF (3.50 g, 19.11 mmol) in DMF (22 mL) was added powered K$_2$CO$_3$ (5.28 g, 38.23 mmol). Then 1-fluoro-2-iodoethane (13.9 g, 81.91 mmol, 8.0 mL) was added to the mixture. The reaction mixture was heated at 80° C. overnight. Then the reaction was checked by LC-MS. The product doesn't ionize well. There were 3 major peaks, one of which corresponded to the starting acid, another corresponding to the desired product (the largest of the 3) and a third peak presumed to be a monoalkylated intermediate. The mixture was heated at 90° C. for 3 d after which LC-MS showed there was one peak which corresponded to the desired product. The mixture was cooled to rt and poured into EtOAc then it was diluted with water. The biphasic mixture was shaken in a sep funnel and the aqueous layer was separated. The aqueous layer was then extracted twice more with EtOAc. The combined organic layers were washed twice with saturated NaCl, dried over sodium sulfate, decanted from the drying agent, and concentrated in vacuo to give 6.10 g, 116%, of a yellow oil.

Example 40B

2-Fluoroethyl 2-amino-5-(2-fluoroethoxy)benzoate

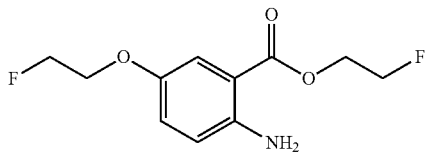 [SMILES: Nc1ccc(OCCF)cc1C(=O)OCCF]

To a solution of propyl 2-nitro-5-propoxybenzoate (6.99 g, 26.16 mmol) in a 250 mL RBF in MeOH (52 mL) was added 10% Pd/C (1.4 g, ~20 wt %). The flask was evacuated with house vacuum then filled with hydrogen. This process was done two more times then the reaction mixture was stirred under an atmosphere of hydrogen for 3 d after which LC-MS showed the reaction was complete. The mixture was filtered through a pad of Celite with MeOH to remove the catalyst. There was still some catalyst present in the filtered solution so it was concentrated in vacuo to remove most of the methanol and it was filtered through another pad of Celite. There yielded, after removal of the methanol in vacuo, 3.988 g, 73%, of the crude product as a grey solid. The product is used as is in the next step. MS (ES+) m/e 246 (M+H)$^+$.

Example 40C 6-(2-Fluoroethoxy)quinazoline-2,4(1H,3H)-dione

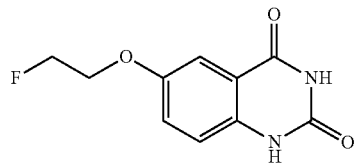 [SMILES: O=c1[nH]c(=O)c2cc(OCCF)ccc2[nH]1]

A mixture of 2-fluoroethyl 2-amino-5-(2-fluoroethoxy)benzoate (3.98 g, 16.23 mmol) and urea (14.62 g, 2.43 mmol, 15 eq.) was heated at 180° C. overnight after which LC-MS showed a main peak for the desired product mass and peaks for some impurities. The mixture was cooled to rt and water was added. The reaction mixture had turned into a solid mass which had to be broken up by a spatula. After it was broken up, a fine precipitate had formed and much of the solid had dissolved into solution. The resulting mixture was filtered and washed with water. The filter cake was then stirred in water for 2 h after which it was filtered and dried on the filter overnight under vacuum to give 5.15 g, 142%, of a tan solid. This material is used as is in the next step. MS (ES+) m/e 225 (M+H)$^+$.

Example 40D

2,4-Dichloro-6-(2-fluoroethoxy)quinazoline

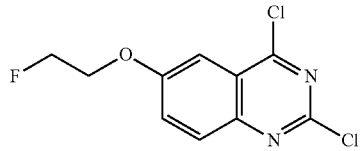 [SMILES: FCCOc1ccc2nc(Cl)nc(Cl)c2c1]

To a mixture of 6-(2-fluoroethoxy)quinazoline-2,4(1H, 3H)-dione (2.24 g, 10.00 mmol) in POCl₃ (8.60 g, 56.10 mmol, 5.2 mL, 5.61 eq.) in a 100 mL RBF was added DIEA (1.29 g, 10.00 mmol, 1.74 mL) then the reaction mixture was heated overnight at 90° C. after which LC-MS showed the reaction was complete. The mixture was cooled to rt and concentrated in vacuo to remove as much excess POCl₃ as possible. The residue was cooled to 0° C. then water (75 mL, cooled to below 10° C.) was added slowly with good stirring. The mixture was transferred to a 500 mL Erlenmeyer flask. Then saturated NaHCO₃ was added to basify the mixture to pH 9-10. Much bubbling took place during the addition. The mixture was diluted with EtOAc and stirred with a large spatula. An emulsion formed and the emulsion was vacuum filtered through filter paper. It was noted that some solid that wasn't soluble in either layer was present so that solid was also filtered off during the filtration. The aqueous layer was separated and extracted twice more with EtOAc. The combined organic layers were dried over sodium sulfate, decanted from the drying agent, and concentrated in vacuo to give 770 mg of a yellow oil that was then redissolved in EtOAc. Celite (8 g) was added and the solvent was removed in vacuo. Column chromatography (10% EtOAc/90% Hexanes to 70% EtOAc/30% Hexanes, 80 g silica gel column) gave 201 mg, 8%, of the desired product as an off-white solid. MS (ES+) m/e 262 (M+H)⁺.

Example 40E

N-(4-(1H-Pyrazol-4-yl)phenyl)-2-chloro-6-(2-fluoroethoxy)quinazolin-4-amine

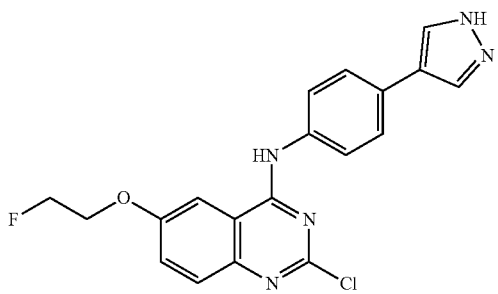 [SMILES: FCCOc1ccc2nc(Cl)nc(Nc3ccc(-c4cn[nH]c4)cc3)c2c1]

To a solution of 2,4-dichloro-6-(2-fluoroethoxy)quinazoline (201 mg, 0.77 mmol) and 4-(4-aminophenyl)pyrazole amine (122 mg, 0.77 mmol) in DMF (1.5 mL) in a 1-dram vial was added DIEA (199 mg, 1.54 mmol, 0.268 mL). The vial was flushed with nitrogen and the mixture was heated at 100° C. overnight. LC-MS showed one main peak corresponding to the desired product mass. The reaction mixture was cooled to rt and poured into water. The precipitate was filtered and washed with water. The resulting yellow solid was left to dry on the filter for 3 h to give 210 mg, 71%, of a yellow solid which was used as is in the next reaction. MS (ES+) m/e 384 (M+H)⁺.

Example 40F

2-(3-(4-((4-(1H-Pyrazol-4-yl)phenyl)amino)-6-(2-fluoroethoxy)quinazolin-2-yl)phenoxy)-N-isopropylacetamide

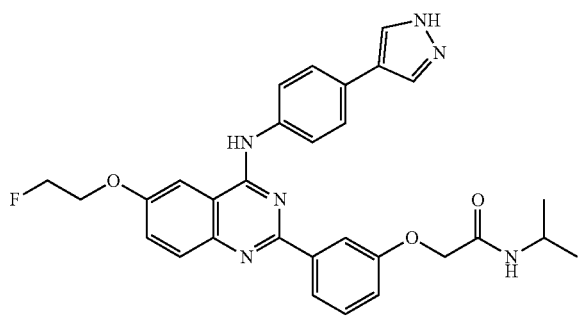 [SMILES: CC(C)NC(=O)COc1cccc(-c2nc(Nc3ccc(-c4cn[nH]c4)cc3)c3cc(OCCF)ccc3n2)c1]

To N-(4-(1H-pyrazol-4-yl)phenyl)-2-chloro-6-(2-fluoroethoxy)quinazolin-4-amine (28.7 mg, 0.075 mmol), N-isopropyl-2-(3-(4,4,5,5-tetramethyl-1,3,2-dioxaborolan-2-yl)phenoxy)acetamide (23.9 mg, 0.075 mmol), and Pd(PPh₃)₄ (8.6 mg, 0.0075 mmol) in a 10 mL microwave vial was added dioxane (0.750 mL), a solution of aqueous sodium carbonate (2M, 0.075 mL, 0.15 mmol) and water (0.075 mL). The vessel was flushed with nitrogen then the vessel was irradiated at 180° C. for 2 h. After the reaction was cooled to rt, the reaction was checked by LC-MS. LC-MS showed one main peak for the reaction. The reaction mixture was transferred to a 20 mL vial with the aid of methanol. The solvent was removed in vacuo using a rotovap. The resulting residue was stirred in DMSO/MeOH (1.5 mL/0.2 mL) for 30 min then the mixture was filtered through a 0.45 m syringe filter before HPLC purification. HPLC (10% B/90% A to 100% B gradient where A is water (0.1% TFA) and B is ACN (0.1% TFA), 14 min gradient time and 17 min run time) gave 8.7 mg, 18%, of the compound as a yellow solid. ¹H NMR (500 MHz, DMSO-d₆) δ 10.49 (s, 1H), 8.15 (d, J=8.4 Hz, 3H), 8.01-7.85 (m, 6H), 7.78 (d, J=8.2 Hz, 2H), 7.71 (d, J=8.0 Hz, 1H), 7.53 (t, J=8.1 Hz, 1H), 7.20 (d, J=7.9 Hz, 1H), 4.94 (t, J=3.7 Hz, 1H), 4.85 (t, J=3.7 Hz, 1H), 4.57 (s, 2H), 4.54-4.50 (m, 1H), 4.46 (t, J=3.8 Hz, 1H), 3.99 (dq, J=13.6, 6.8 Hz, 1H), 1.10 (d, J=6.6 Hz, 6H). MS (ES+) m/e 541 (M+H)⁺.

Example 41

2-(3-(4-((4-(1H-pyrazol-4-yl)phenyl)amino)-6-iso-propoxyquinazolin-2-yl)phenoxy)-N-isopropylacet-amide

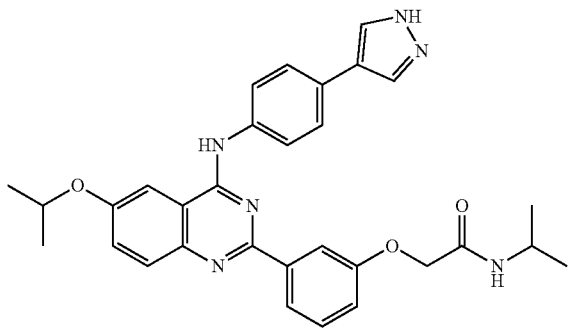 [SMILES: CC(C)NC(=O)COc1cccc(-c2nc(Nc3ccc(-c4cn[nH]c4)cc3)c3cc(OC(C)C)ccc3n2)c1]

Example 41A

Isopropyl 5-isopropoxy-2-nitrobenzoate

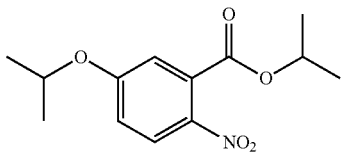 [SMILES: CC(C)OC(=O)c1cc(OC(C)C)ccc1[N+](=O)[O-]]

A mixture of 5-hydroxy-2-nitrobenzoic acid (4.0 g, 21.84 mmol), 2-iodopropane (14.85 g, 87.37 mmol), K$_2$CO$_3$ (6.0 g, 43.69 mmol) in DMF (73 mL) was stirred at 60° C. overnight, diluted with water and extracted with EtOAc. The organic layer was washed with water (3×), brine, dried over Na$_2$SO$_4$, and concentrated in vacuo to provide the title compound (5.3 g, 100%), which was used directly for next step reaction without further purification. MS (ES+) m/e 268 (M+H)$^+$.

Example 41B

Isopropyl 2-amino-5-isopropoxybenzoate

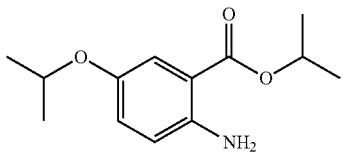

Isopropyl 5-isopropoxy-2-nitrobenzoate (5.3 g, 21.84 mmol) in MeOH (100 mL) was hydrogenated in the presence of 10% Pd/C (0.53 g) overnight. The reaction mixture was filtered through a pad of celite, and the filtrate was concentrated in vacuo to provide the title compound (4.65 g). MS (ES+) m/e 238 (M+H)$^+$.

Example 41C

6-Isopropoxyquinazoline-2,4(1H,3H)-dione

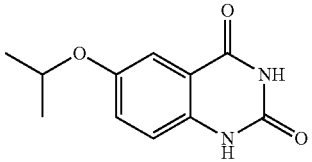 [SMILES: CC(C)Oc1ccc2[nH]c(=O)[nH]c(=O)c2c1]

A mixture of isopropyl 2-amino-5-isopropoxybenzoate (4.65 g, 19.60 mmol) and urea (17.65 g, 293.9 mmol, 15 eq.) was heated at 180° C. overnight after which LC-MS showed a main peak for the desired product mass and a minor amount of the starting aniline present. The mixture was cooled to rt and water was added. The reaction mixture had turned into a thick slurry. The slurry was filtered was filtered and washed with water. The filter cake was then stirred in water overnight after which it was filtered and dried on the filter for several hours under vacuum then in a desiccator for 3 d under vacuum to give 8.1 g of a tan solid. To this material in a 125 mL Erlenmeyer flask was added about 75 mL water and the mixture was stirred overnight then it was filtered through filter paper. Air was pulled through the filtrate for 2 h after which the solid was put into a 250 mL RBF and toluene (75 mL) was added. The toluene was removed in vacuo at 50° C. The toluene addition and removal were performed two more times to give 6.65 g of a solid that was used as is in the next step reaction. MS (ES+) m/e 221 (M+H)$^+$.

Example 41D 2,4-Dichloro-6-isopropoxyquinazoline

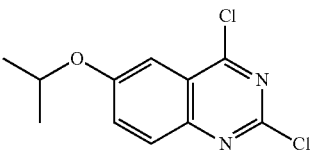 [SMILES: CC(C)Oc1ccc2nc(Cl)nc(Cl)c2c1]

To a mixture of 6-isopropoxyquinazoline-2,4(1H,3H)-dione (1.65 g, 7.50 mmol) in POCl$_3$ (6.45 g, 42.07 mmol, 3.9 mL, 5.61 eq.) in a 100 mL RBF was added DIEA (969 mg, 7.50 mmol, 1.3 mL) then the reaction mixture was heated overnight at 90° C. after which LC-MS showed the reaction was complete. The residue was cooled to 0° C. then water (25 mL, cooled to below 10° C.) was added slowly with good stirring. The mixture was transferred to a 500 mL Erlenmeyer flask. Then saturated NaHCO$_3$ was added in portions to basify the mixture to pH 9-10. Much bubbling took place during the addition. The mixture was diluted with EtOAc and stirred with a large spatula. An emulsion formed and the emulsion was vacuum filtered through filter paper. It was noted that some solid that wasn't soluble in either layer was present so that solid was also filtered off during the filtration. The aqueous layer was separated and extracted three times with EtOAc. The combined organic layers were dried over sodium sulfate, decanted from the drying agent, and concentrated in vacuo to give 857 mg, 44%, of a yellow solid that was used as is in the next reaction. MS (ES+) m/e 257 (M+H)+.

Example 41E

N-(4-(1H-Pyrazol-4-yl)phenyl)-2-chloro-6-iso-propoxyquinazolin-4-amine

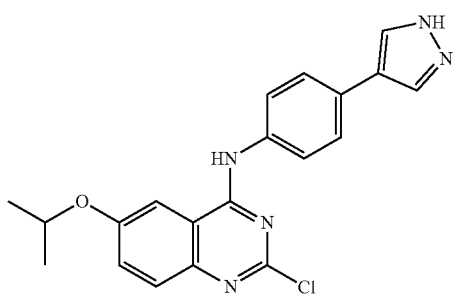 [SMILES: CC(C)Oc1ccc2nc(Cl)nc(Nc3ccc(-c4cn[nH]c4)cc3)c2c1]

To a solution of 2,4-dichloro-6-isopropoxyquinazoline (257 mg, 1.00 mmol) and 4-(4-aminophenyl)pyrazole amine (159 mg, 1.00 mmol) in DMF (2 mL) in a 1-dram vial was added DIEA (258 mg, 2.00 mmol, 0.348 mL). The mixture was heated at 100° C. overnight. LC-MS showed one main peak corresponding to the desired product mass. The reaction mixture was cooled to rt and poured into water. The precipitate was filtered and washed with water. The resulting yellow solid was left to dry on the filter overnight to give the title compound (357 mg, 94%), as a yellow solid which was used as is in the next reaction. MS (ES+) m/e 380 (M+H)+.

Example 41F 2-(3-(4-((4-(1H-Pyrazol-4-yl)phenyl)amino)-6-iso-propoxyquinazolin-2-yl)phenoxy)-N-isopropylacet-amide

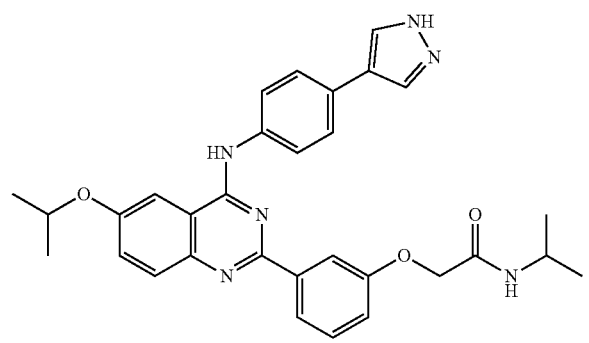

To N-(4-(1H-pyrazol-4-yl)phenyl)-2-chloro-6-iso-propoxyquinazolin-4-amine (28.4 mg, 0.075 mmol), N-iso-propyl-2-(3-(4,4,5,5-tetramethyl-1,3,2-dioxaborolan-2-yl) phenoxy)acetamide (23.9 mg, 0.075 mmol), and Pd(PPh3)4 (8.7 mg, 0.0075 mmol) in a 10 mL microwave vial was added dioxane (0.750 mL), a solution of aqueous sodium carbonate (2M, 0.075 mL, 0.15 mmol) and water (0.075 mL). The vessel was flushed with nitrogen then the vessel was irradiated in a microwave reactor at 180° C. for 2 h. After the reaction was cooled to rt, it was checked by LC-MS. LC-MS showed one main peak for the reaction. The reaction mixture was transferred to a 20 mL vial with the aid of methanol. The solvent was removed in vacuo using a rotovap. The resulting residue was stirred in DMSO/MeOH (1.5 mL/0.2 mL) for 30 min then the mixture was filtered through a 0.45 μm syringe filter before HPLC. HPLC (10% B/90% A to 100% B gradient where A is water (0.1% TFA) and B is ACN (0.1% TFA), 14 min gradient time and 17 min run time) gave 13 mg, 26%, of the title compound as a solid. $^1$H NMR (500 MHz, DMSO-$d_6$) δ 10.18 (s, 1H), 8.10 (d, J=25.4 Hz, 3H), 7.98 (d, J=7.9 Hz, 3H), 7.90 (t, J=11.8 Hz, 3H), 7.76 (d, J=8.4 Hz, 2H), 7.59 (d, J=8.5 Hz, 1H), 7.49 (t, J=7.9 Hz, 1H), 7.16 (d, J=8.0 Hz, 1H), 4.92 (hept, J=5.9 Hz, 1H), 4.56 (s, 2H), 3.99 (dp, J=8.1, 6.6 Hz, 1H), 1.40 (d, J=6.0 Hz, 6H), 1.11 (d, J=6.5 Hz, 6H). MS (ES+) m/e 537 (M+H)+.

Example 42

2-(3-(4-((4-(1H-pyrazol-4-yl)phenyl)amino)-6-(2-methoxyethoxy)quinazolin-2-yl)phenoxy)-N-(sec-butyl)acetamide

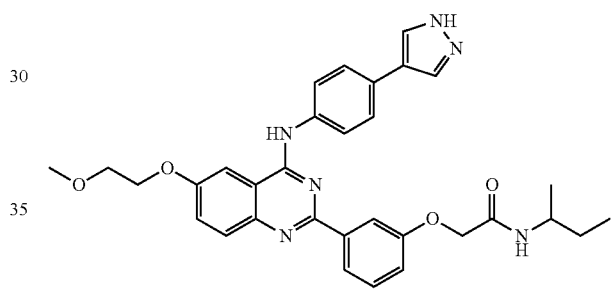

29% yield. $^1$H NMR (500 MHz, DMSO-$d_6$) δ 10.45 (s, 1H), 8.13 (s, 3H), 8.03-7.86 (m, 6H), 7.77 (d, J=8.2 Hz, 2H), 7.66 (d, J=8.9 Hz, 1H), 7.52 (d, J=10.0 Hz, 1H), 7.19 (d, J=8.0 Hz, 1H), 4.59 (s, 2H), 4.42-4.27 (m, 2H), 3.87-3.71 (m, 6H), 1.50-1.34 (m, 2H), 1.07 (d, J=6.6 Hz, 3H), 0.80 (t, J=7.3 Hz, 3H). MS (ES+) m/e 567 (M+H)+.

Example 43

2-(3-(4-((4-(1H-pyrazol-4-yl)phenyl)amino)-6-(2-fluoroethoxy)quinazolin-2-yl)phenoxy)-N-(sec-butyl)acetamide

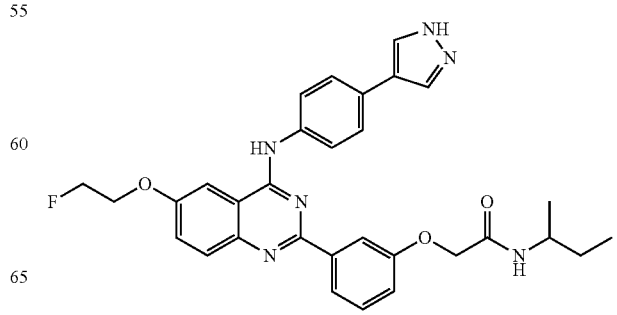

35% yield. $^1$H NMR (500 MHz, DMSO-$d_6$) δ 10.45 (s, 1H), 8.13 (s, 2H), 8.03-7.84 (m, 5H), 7.78 (d, J=8.5 Hz, 2H), 7.69 (d, J=9.0 Hz, 1H), 7.50 (d, J=9.1 Hz, 1H), 7.18 (s, 1H), 6.42-6.28 (m, 1H), 4.90 (dt, J=47.6, 3.7 Hz, 2H), 4.59 (s, 2H), 4.48 (dt, J=29.8, 3.8 Hz, 2H), 4.38 (s, 1H), 3.78 (dp, J=22.3, 7.0 Hz, 1H), 1.43 (ddd, J=13.4, 8.4, 5.3 Hz, 2H), 1.06 (t, J=7.4 Hz, 3H), 0.80 (t, J=7.5 Hz, 3H). MS (ES+) m/e 555 (M+H)$^+$.

Example 44

2-(3-(4-((4-(1H-pyrazol-4-yl)phenyl)amino)-6-fluoroquinazolin-2-yl)phenoxy)-N-(sec-butyl)acetamide

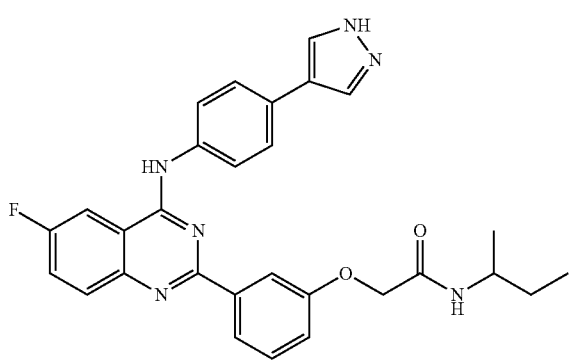 [SMILES: CCC(C)NC(=O)COc1cccc(-c2nc(Nc3ccc(-c4cn[nH]c4)cc3)c3cc(F)ccc3n2)c1]

26% yield. $^1$H NMR (500 MHz, DMSO-$d_6$) δ 9.99 (s, 1H), 8.61-8.46 (m, 1H), 8.16-8.03 (m, 5H), 7.97 (d, J=8.2 Hz, 3H), 7.90 (d, J=8.4 Hz, 1H), 7.84 (d, J=8.2 Hz, 1H), 7.75 (d, J=8.1 Hz, 2H), 7.47 (t, J=8.0 Hz, 1H), 7.19-7.10 (m, 1H), 4.59 (s, 2H), 3.87-3.77 (m, 1H), 1.43 (dt, J=13.7, 7.2 Hz, 2H), 1.08 (d, J=6.6 Hz, 3H), 0.80 (t, J=7.3 Hz, 3H). MS (ES+) m/e 511 (M+H)$^+$.

Example 45

(S)-2-(3-(4-((4-(1H-pyrazol-4-yl)phenyl)amino)-6-(2-methoxyethoxy)quinazolin-2-yl)phenoxy)-N-(sec-butyl)acetamide

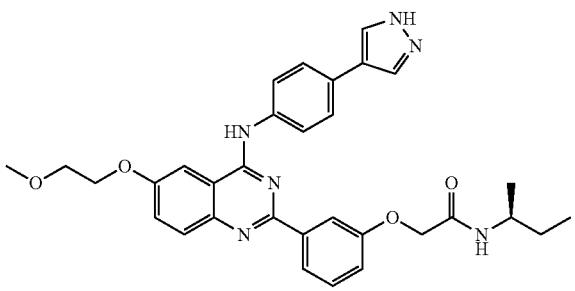 [SMILES: CC[C@H](C)NC(=O)COc1cccc(-c2nc(Nc3ccc(-c4cn[nH]c4)cc3)c3cc(OCCOC)ccc3n2)c1]

28% yield. $^1$H NMR (500 MHz, DMSO-$d_6$) δ 10.42 (s, 1H), 8.12 (d, J=9.4 Hz, 3H), 7.98 (s, 2H), 7.90 (dd, J=8.5, 4.8 Hz, 4H), 7.77 (d, J=8.5 Hz, 2H), 7.66 (d, J=9.0 Hz, 1H), 7.51 (t, J=8.0 Hz, 1H), 7.18 (d, J=8.0 Hz, 1H), 4.59 (s, 2H), 4.39-4.28 (m, 2H), 3.83-3.78 (m, 5H), 1.51-1.36 (m, 2H), 1.07 (d, J=6.6 Hz, 3H), 0.80 (t, J=7.4 Hz, 3H). MS (ES+) m/e (M+H)$^+$.

Example 46

(S)-2-(3-(4-((4-(1H-pyrazol-4-yl)phenyl)amino)-6-(2-fluoroethoxy)quinazolin-2-yl)phenoxy)-N-(sec-butyl)acetamide

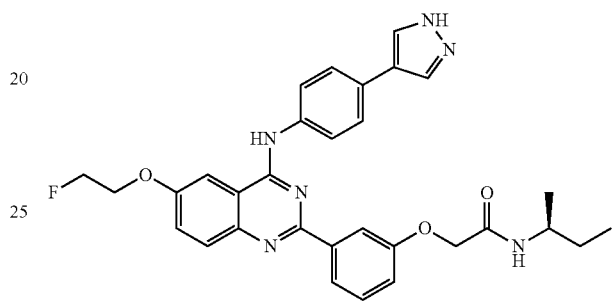

40% yield. $^1$H NMR (500 MHz, DMSO-$d_6$) δ 10.44 (s, 1H), 8.13 (s, 2H), 8.03-7.86 (m, 5H), 7.76 (dd, J=13.0, 7.7 Hz, 2H), 7.69 (s, 1H), 7.51 (s, 1H), 7.18 (d, J=8.0 Hz, 1H), 7.05 (t, J=8.0 Hz, 1H), 6.36 (ddd, J=11.3, 5.4, 2.6 Hz, 2H), 4.90 (dt, J=47.7, 3.8 Hz, 2H), 4.59 (s, 2H), 4.49 (dd, J=30.0, 4.5 Hz, 2H), 4.38 (s, 2H), 3.78 (dq, J=23.1, 7.3 Hz, 1H), 1.42 (dt, J=12.8, 4.7 Hz, 2H), 1.06 (t, J=7.4 Hz, 3H), 0.80 (t, J=7.4 Hz, 3H). MS (ES+) m/e 555 (M+H)$^+$.

Example 47

(S)-2-(3-(4-((4-(1H-pyrazol-4-yl)phenyl)amino)-6-fluoroquinazolin-2-yl)phenoxy)-N-(sec-butyl)acetamide

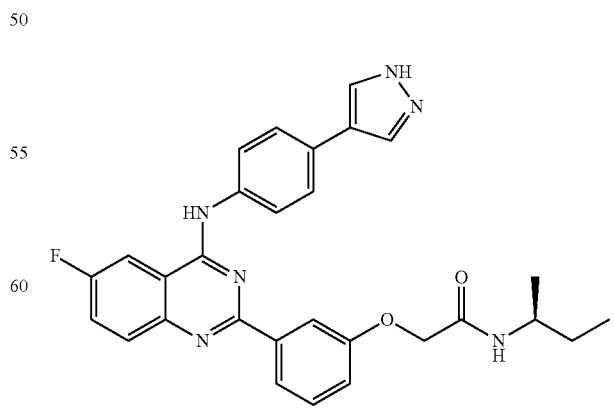

30% yield. MS (ES+) m/e 511 (M+H)$^+$.

Example 48

(S)-2-(3-(4-((4-(1H-pyrazol-4-yl)phenyl)amino)-6-methoxyquinazolin-2-yl)phenoxy)-N-(sec-butyl)acetamide

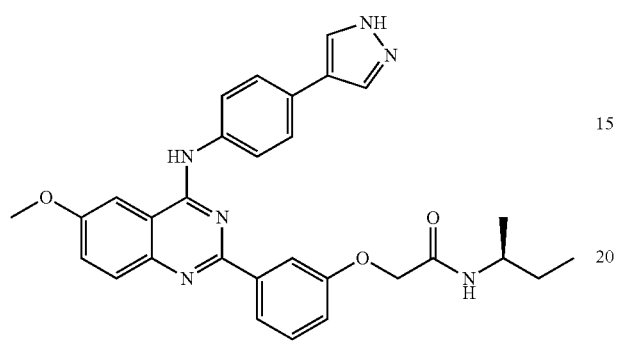

25% yield. $^1$H NMR (500 MHz, DMSO-d$_6$) δ 10.64 (s, 1H), 8.13 (d, J=14.6 Hz, 4H), 8.02-7.85 (m, 8H), 7.78 (d, J=8.2 Hz, 2H), 7.67 (d, J=9.0 Hz, 1H), 7.53 (s, 1H), 7.20 (d, J=8.0 Hz, 1H), 4.59 (s, 2H), 4.01 (s, 3H), 3.80 (t, J=7.5 Hz, 1H), 1.50-1.35 (m, 2H), 1.07 (d, J=6.4 Hz, 3H), 0.80 (t, J=7.3 Hz, 3H). MS (ES+) m/e 523 (M+H)$^+$.

Example 49

(R)-2-(3-(4-((4-(1H-pyrazol-4-yl)phenyl)amino)-6-(2-methoxyethoxy)quinazolin-2-yl)phenoxy)-N-(sec-butyl)acetamide

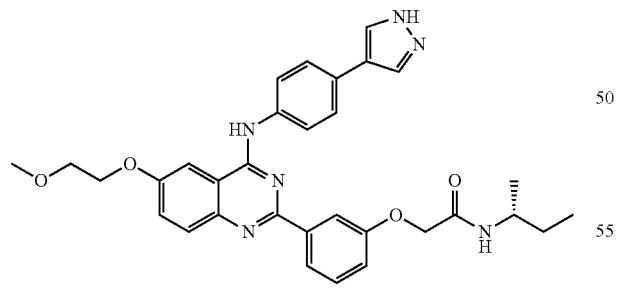

28% yield. $^1$H NMR (500 MHz, DMSO-d$_6$) δ 10.35 (s, 1H), 8.12 (d, J=9.3 Hz, 3H), 7.98 (s, 2H), 7.90 (dd, J=8.4, 4.9 Hz, 4H), 7.81-7.73 (m, 2H), 7.66 (d, J=9.2 Hz, 1H), 7.51 (t, J=8.1 Hz, 1H), 7.18 (d, J=8.0 Hz, 1H), 4.59 (s, 2H), 4.37-4.25 (m, 2H), 3.83-3.78 (m, 1H), 3.38 (s, 5H), 1.42 (qd, J=7.3, 3.9 Hz, 2H), 1.07 (d, J=6.6 Hz, 3H), 0.80 (t, J=7.4 Hz, 3H). MS (ES+) m/e 567 (M+H)$^+$.

Example 50

(R)-2-(3-(4-((4-(1H-pyrazol-4-yl)phenyl)amino)-6-(2-fluoroethoxy)quinazolin-2-yl)phenoxy)-N-(sec-butyl)acetamide

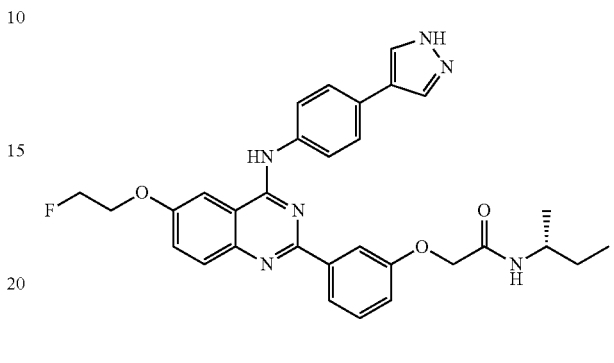

36% yield. $^1$H NMR (500 MHz, DMSO-d$_6$) δ 9.41 (s, 1H), 8.14 (d, J=7.6 Hz, 3H), 7.93 (dd, J=34.0, 7.0 Hz, 6H), 7.83-7.65 (m, 3H), 7.53 (s, 1H), 7.20 (s, 1H), 4.98-4.77 (m, 2H), 4.59 (s, 2H), 4.49 (dt, J=30.3, 4.1 Hz, 2H), 4.38 (s, 1H), 3.83-3.77 (m, 1H), 1.52-1.37 (m, 2H), 1.06 (t, J=6.8 Hz, 3H), 0.80 (t, J=7.3 Hz, 3H). MS (ES+) m/e 555 (M+H)$^+$.

Example 51

(R)-2-(3-(4-((4-(1H-pyrazol-4-yl)phenyl)amino)-6-fluoroquinazolin-2-yl)phenoxy)-N-(sec-butyl)acetamide

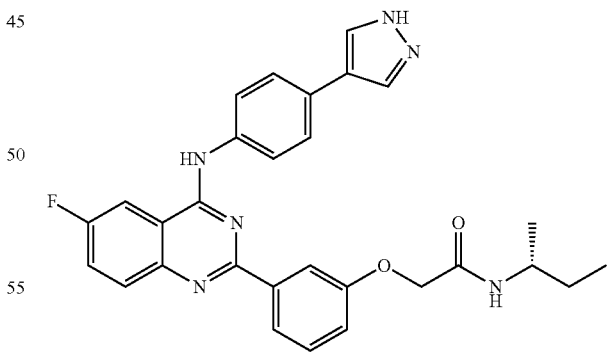

30% yield. $^1$H NMR (500 MHz, DMSO-d$_6$) δ 9.95 (s, 1H), 8.50 (dd, J=10.0, 2.7 Hz, 1H), 8.19-8.04 (m, 4H), 8.01-7.93 (m, 3H), 7.90 (d, J=8.4 Hz, 1H), 7.87-7.80 (m, 1H), 7.74 (d, J=8.4 Hz, 2H), 7.47 (t, J=8.1 Hz, 1H), 7.13 (dd, J=8.6, 2.4 Hz, 1H), 4.58 (s, 2H), 3.88-3.75 (m, 1H), 1.52-1.35 (m, 2H), 1.08 (d, J=6.7 Hz, 3H), 0.80 (t, J=7.4 Hz, 3H). MS (ES+) m/e 511 (M+H)$^+$.

Example 52

(R)-2-(3-(4-((4-(1H-pyrazol-4-yl)phenyl)amino)-6-methoxyquinazolin-2-yl)phenoxy)-N-(sec-butyl)acetamide

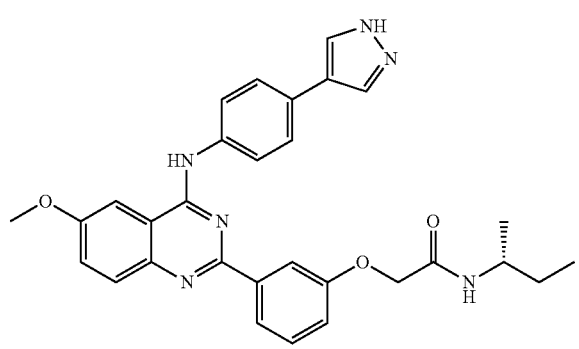 [SMILES: CC[C@@H](C)NC(=O)COc1cccc(-c2nc(Nc3ccc(-c4cn[nH]c4)cc3)c3cc(OC)ccc3n2)c1]

54% yield. $^1$H NMR (500 MHz, DMSO-d$_6$) δ 9.43 (s, 1H), 8.12 (d, J=18.3 Hz, 3H), 8.03-7.84 (m, 6H), 7.78 (d, J=8.3 Hz, 2H), 7.65 (s, 1H), 7.52 (s, 1H), 7.19 (s, 1H), 4.59 (s, 2H), 4.00 (s, 3H), 3.80 (m, 1H), 1.52-1.36 (m, 2H), 1.06 (t, J=6.8 Hz, 3H), 0.80 (t, J=7.3 Hz, 3H). MS (ES+) m/e (M+H)$^+$.

Example 53

2-(3-(4-((4-(1H-pyrazol-4-yl)phenyl)amino)-7-fluoroquinazolin-2-yl)phenoxy)-N-(sec-butyl)acetamide

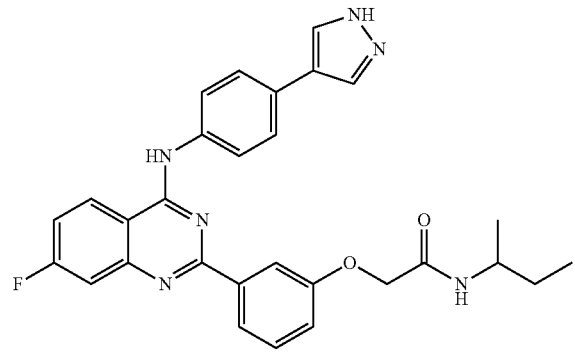 [SMILES: CC[C@@H](C)NC(=O)COc1cccc(-c2nc(Nc3ccc(-c4cn[nH]c4)cc3)c3ccc(F)cc3n2)c1]

24% yield. $^1$H NMR (500 MHz, DMSO-d$_6$) δ 10.12 (s, 1H), 8.71 (dd, J=9.1, 5.9 Hz, 1H), 8.17-8.01 (m, 4H), 7.92 (dd, J=22.9, 8.4 Hz, 3H), 7.74 (d, J=8.3 Hz, 2H), 7.59 (ddt, J=11.2, 8.7, 4.3 Hz, 2H), 7.47 (t, J=8.1 Hz, 1H), 7.14 (dd, J=8.2, 2.5 Hz, 1H), 4.58 (s, 2H), 3.81 (m, 1H), 1.43 (m, 2H), 1.07 (d, J=6.6 Hz, 3H), 0.80 (t, J=7.3 Hz, 3H). MS (ES+) m/e 511 (M+H)$^+$.

Example 54

(S)-2-(3-(4-((4-(1H-pyrazol-4-yl)phenyl)amino)-7-fluoroquinazolin-2-yl)phenoxy)-N-(sec-butyl)acetamide

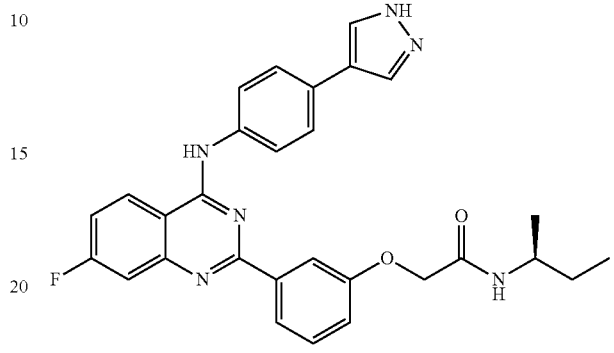

20% yield. $^1$H NMR (500 MHz, DMSO-d$_6$) δ 10.15 (s, 1H), 8.71 (dd, J=9.0, 5.9 Hz, 1H), 8.18-8.03 (m, 4H), 8.00-7.86 (m, 3H), 7.79-7.73 (m, 2H), 7.67-7.56 (m, 2H), 7.47 (t, J=8.2 Hz, 1H), 7.21-7.09 (m, 1H), 4.58 (s, 2H), 3.81 (m, 1H), 1.55-1.33 (m, 2H), 1.07 (d, J=6.6 Hz, 3H), 0.80 (t, J=7.4 Hz, 3H). MS (ES+) m/e 511 (M+H)$^+$.

Example 55

(R)-2-(3-(4-((4-(1H-pyrazol-4-yl)phenyl)amino)-7-fluoroquinazolin-2-yl)phenoxy)-N-(sec-butyl)acetamide

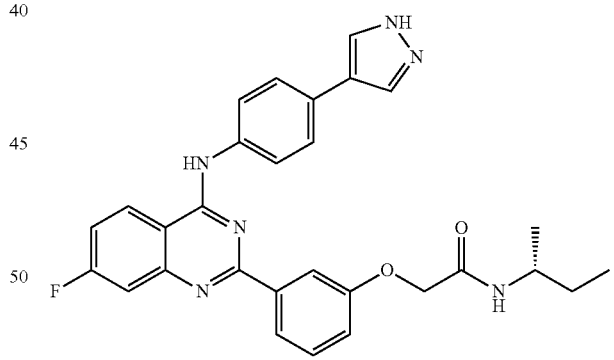

16% yield. $^1$H NMR (500 MHz, DMSO-d$_6$) δ 10.10 (s, 1H), 8.71 (dd, J=9.1, 5.9 Hz, 1H), 8.16-8.01 (m, 4H), 7.99-7.92 (m, 2H), 7.90 (d, J=8.5 Hz, 1H), 7.77-7.69 (m, 2H), 7.65-7.56 (m, 2H), 7.47 (t, J=8.1 Hz, 1H), 7.14 (dd, J=8.4, 2.5 Hz, 1H), 4.58 (s, 2H), 3.81 (m, 1H), 1.50-1.35 (m, 2H), 1.07 (d, J=6.6 Hz, 3H), 0.80 (t, J=7.4 Hz, 3H). MS (ES+) m/e 511 (M+H)$^+$.

Example 56 (Assays)

The combination of inhibitors of both oxidative phosphorylation and glycolysis synergistically suppress cellular ATP levels. Therefore, our assay utilizes the combination of our glucose uptake inhibitors with oligomycin, a well-characterized inhibitor of ATP synthase. Because oligomycin inhibits ATP derived from oxidative phosphorylation, any remaining ATP production is derived from glycolysis. By reading out cellular ATP levels using the Promega Titer Glo kit, we can assess the extent of glycolysis inhibition by our glucose uptake inhibitors. Using this experimental set-up in HT1080 cancer cells, we determined the IC50 of glycolysis inhibition for the compounds.

Example 57 (GLUT1/3 Selectivity)

The GLUT selectivity of the compounds disclosed herein was determined by analyzing the ability of these compounds to inhibit glycolysis in DLD1 WT or DLD GLUT−/−cancer cells that rely on GLUT1 and GLUT3, respectively, for glucose uptake (see FIG. 1). This assay revealed that the compounds disclosed herein inhibit both GLUT1 and GLUT3, while Bay876 is selective for GLUT1. A control compound thought to inhibit both GLUT1 and GLUT3 was shown to do so in this assay. Using this experimental set-up, it was determined the $IC_{50}$ of glycolysis inhibition for the compounds listed in the table in FIG. 1B.

Example 58 (Activated T Cells)

Figure 2:
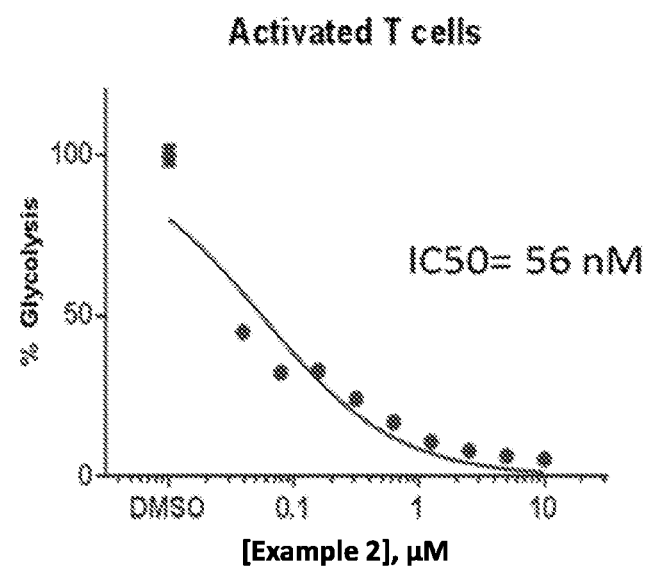
FIG. 2 shows that the metabolism, function and proliferation of activated T cells are suppressed by compounds disclosed herein.
Figure 2:
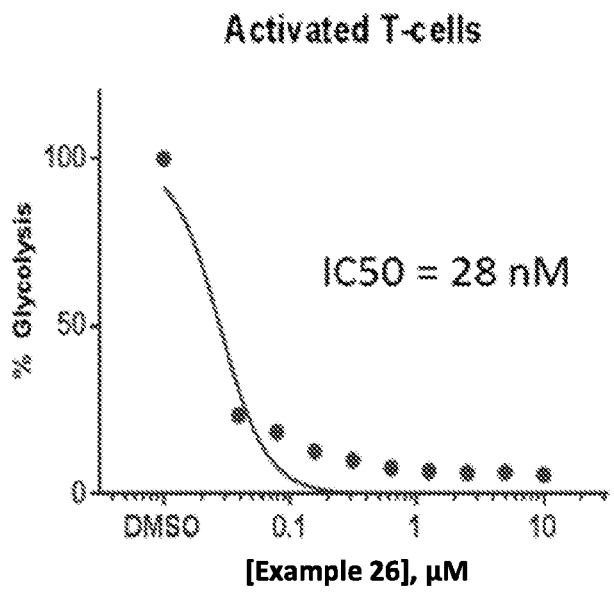
Figure 2:
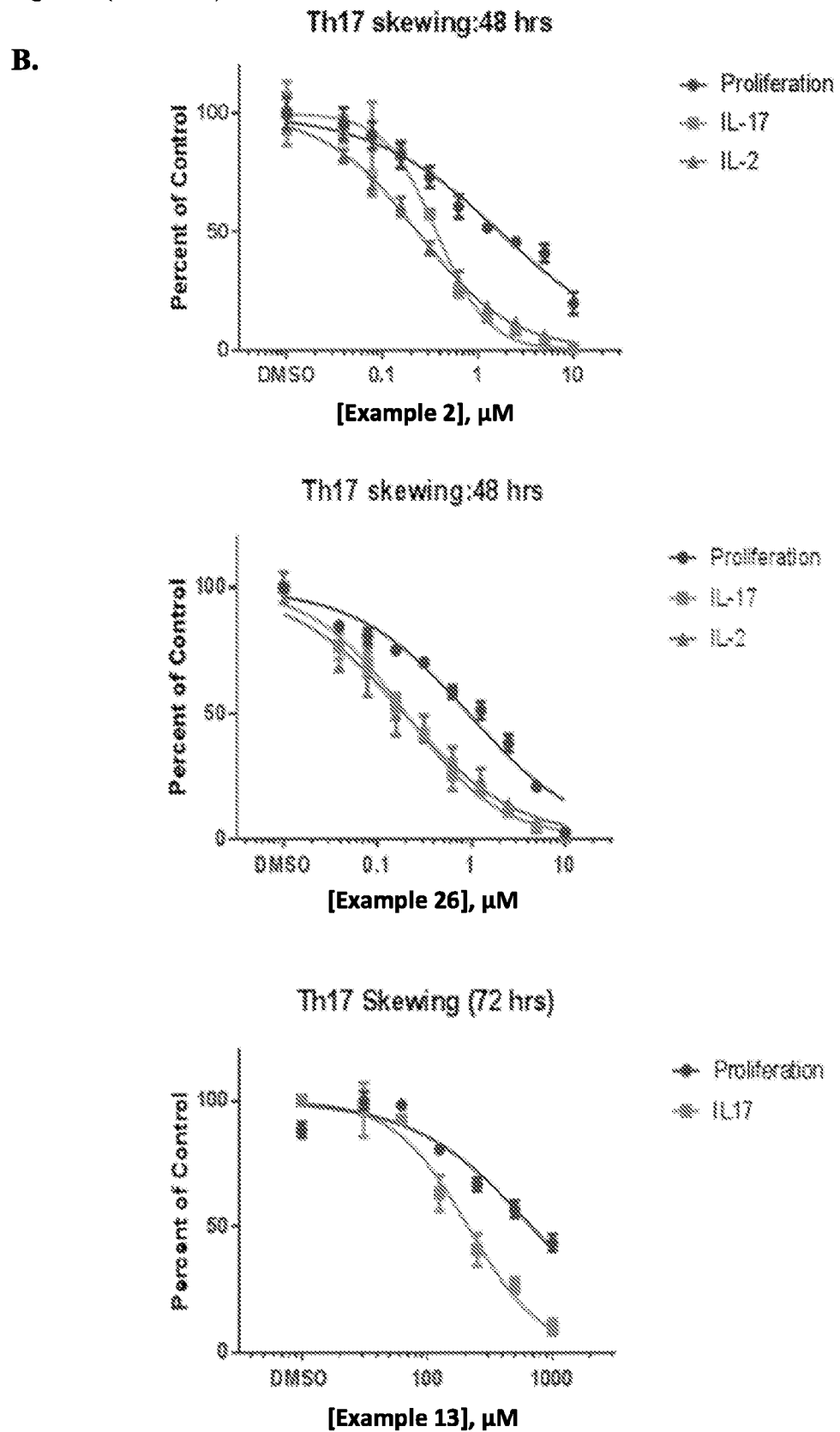
Figure 3:
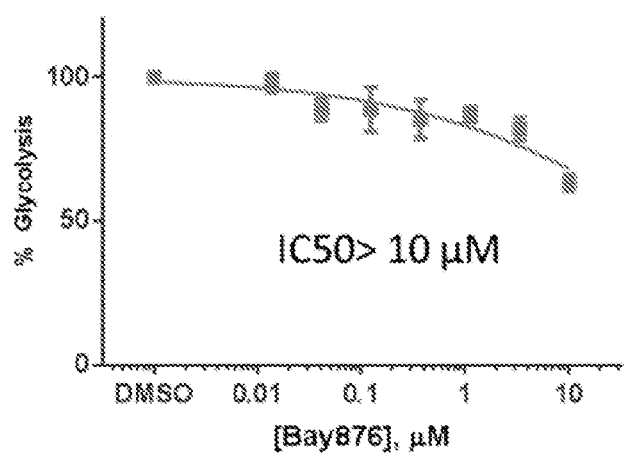
FIG. 3 shows that the metabolism, function and proliferation of activated T cells are unaffected by a selective GLUT1 inhibitor.
Figure 3:
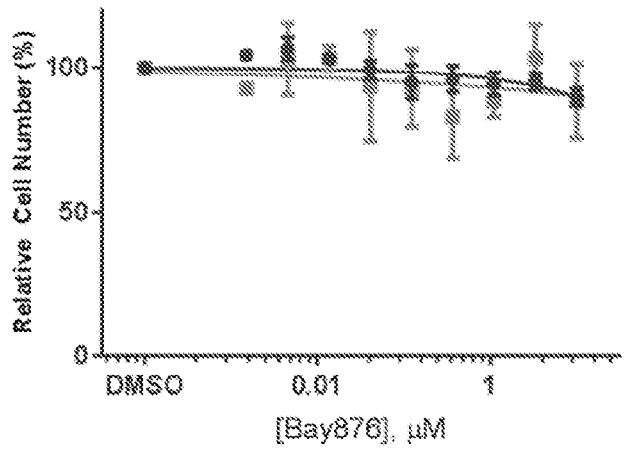

Activated T cells rely on aerobic glycolysis to meet their energetic demands. As shown below, the glucose uptake inhibitors disclosed herein down-regulate glycolysis of activated T cells and inhibit their effector function. In FIG. 2, human CD4 positive T cells were activated by anti-CD3 and anti-CD28 antibodies in the presence of IL1β and TGFβ (activating conditions). Under these conditions, CD4+ T cells rapidly divide and produce many cytokines, including IL-17. 24 hours post-activation, the glucose uptake inhibitors disclosed herein were applied in the one-hour glycolysis assay described above for HT1080 cells. As can be seen in FIG. 2A, these inhibitors potentially suppressed glycolysis in activated T cells. Alternatively, resting T cells were activated and treated simultaneously with the glucose uptake inhibitors disclosed herein for 48 hours. At this time, secreted IL-17, IL-2 and relative cell number were measured (FIG. 2B, right panel). The glucose uptake inhibitors disclosed herein down-regulated both IL-17 secretion and proliferation (at higher concentrations). In contrast, the GLUT1 selective compound Bay876 neither inhibited glycolysis nor IL17 secretion/proliferation (FIG. 3). Therefore, the glucose uptake inhibitors disclosed herein that inhibit both GLUT1 and GLUT3 are likely to have utility against inflammatory disorders and autoimmune disease, including but not limited to diseases characterized by highly glycolytic immune cells and/or Th17/IL-17 driven pathologies.

Example 59 (Activated T Cells)

Figure 4:
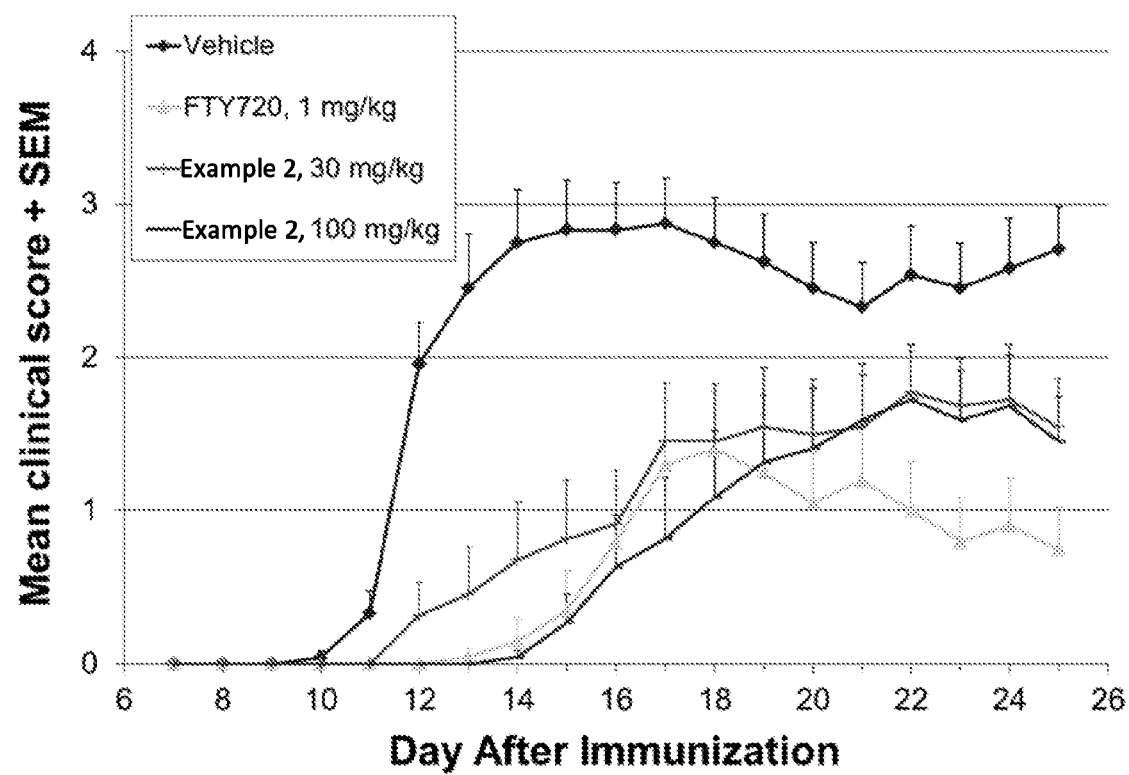
FIG. 4 demonstrates in vivo efficacy for the compound of Example 2 ("Example 2") in a model of mouse Myelin Oligodendrocyte Glycoprotein (MOG)-induced experimental autoimmune encephalitis (EAE). Example 2 dose daily 30 mg/kg and 100 mg/kg p.o. both delayed onset and lowered the end clinical score compared to the vehicle control in this model.

As described above, the glucose uptake inhibitors disclosed herein possess anti-inflammatory properties and inhibit metabolism, effector function and proliferation of activated T cells. In FIG. 4, Example 2 is shown to have efficacy against an in vivo mouse model of inflammation, MOG-induced experimental autoimmune encephalitis. Example 2 both delays the onset and lowers the end clinical score of inflammation in this model. These in vivo data confirm the observations made in cell-based assays and further demonstrate the utility of these compounds against inflammatory disorders, including but not limited to those driven by Th17 CD4+ T cells.

Figure 7:
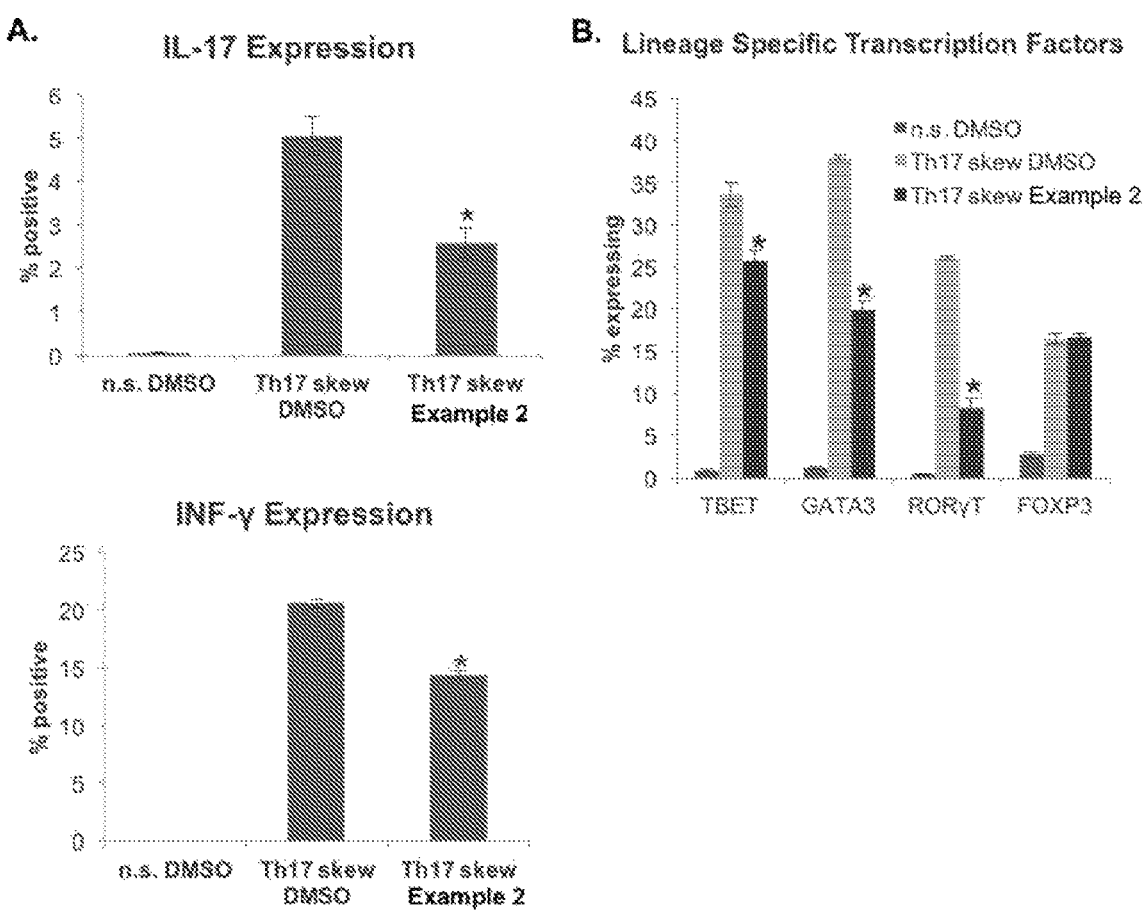
FIG. 7. GLUT inhibitors of the present invention downregulate markers of Teff but not Treg cells.

GLUT1 and GLUT3 inhibitors downregulate the markers of T effector cells but not T regulatory cells. In, CD4 T cells were activated for 48 hrs in the presence of IL-13, TGF-β and 1 μM of compound Example 2. See FIG. 7A,B. For the last 5 hrs, PMA/Ionomycin/Brefeldin A was added and intracellular staining for cytokines was performed. Flow cytometry was used to assess INFγ and IL-17A levels (gated on live cells) and quantification of percent positive cells positive is shown in FIG. 7A. Cells were also cultured and treated as in FIG. 7A, excluding PMA/Ionomycin/Brefeldin A treatment. Flow cytometry was used to assess levels of CD4 T cell lineage defining transcription factors, TBET, GATA3, RORγT, and FOXP3. See FIG. 7B.

Figure 8:
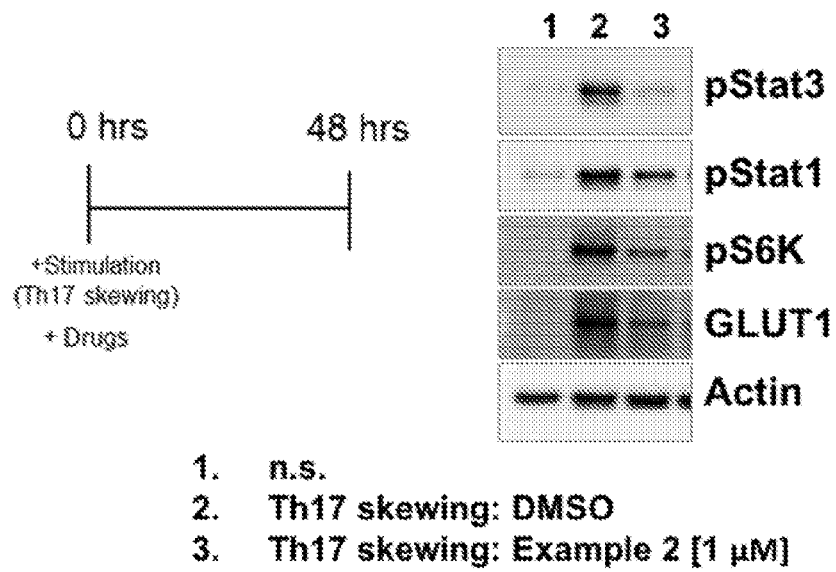
FIG. 8. GLUT inhibitors of the present invention downregulate the phosphorylation of STAT1 and STAT3.
Figure 8:
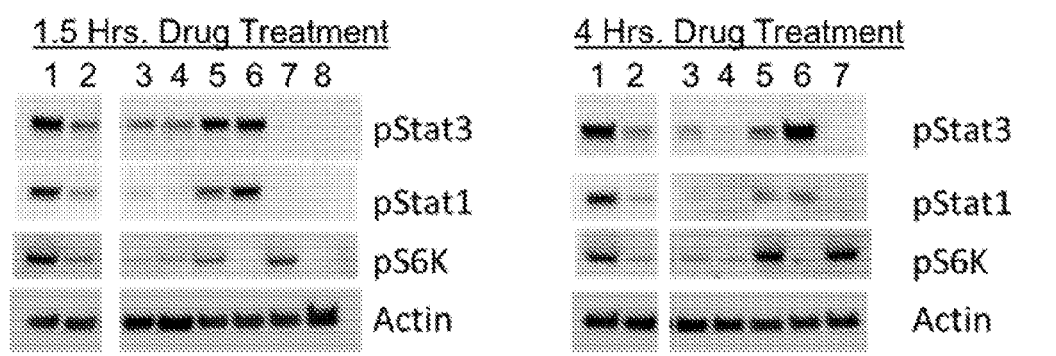

GLUT1/3 inhibitors downregulate phosphorylation of STAT1 and STAT3, key signaling molecules in activated T cells. In FIG. 8A. CD4 T cells were activated for 48 hrs in the presence of IL-1β, TGF-β and 1 μM of the Example 2 compound. Western blotting analysis was used to determine the activation status of Stat3, Stat1 and pS6K (as a marker of mTORC1 activity) and the expression of GLUT1 protein. See FIG. 8A. CD4 T cells were activated for 48 hrs and treated with the indicated compounds in FIG. 8B for 1.5 or 4 hrs. Western blotting analysis was used to determine the activation status of Stat3, Stat1 and pS6K (as a marker of mTORC1 activity). See FIG. 8B.

Example 60 (Monocytes)

Figure 5:
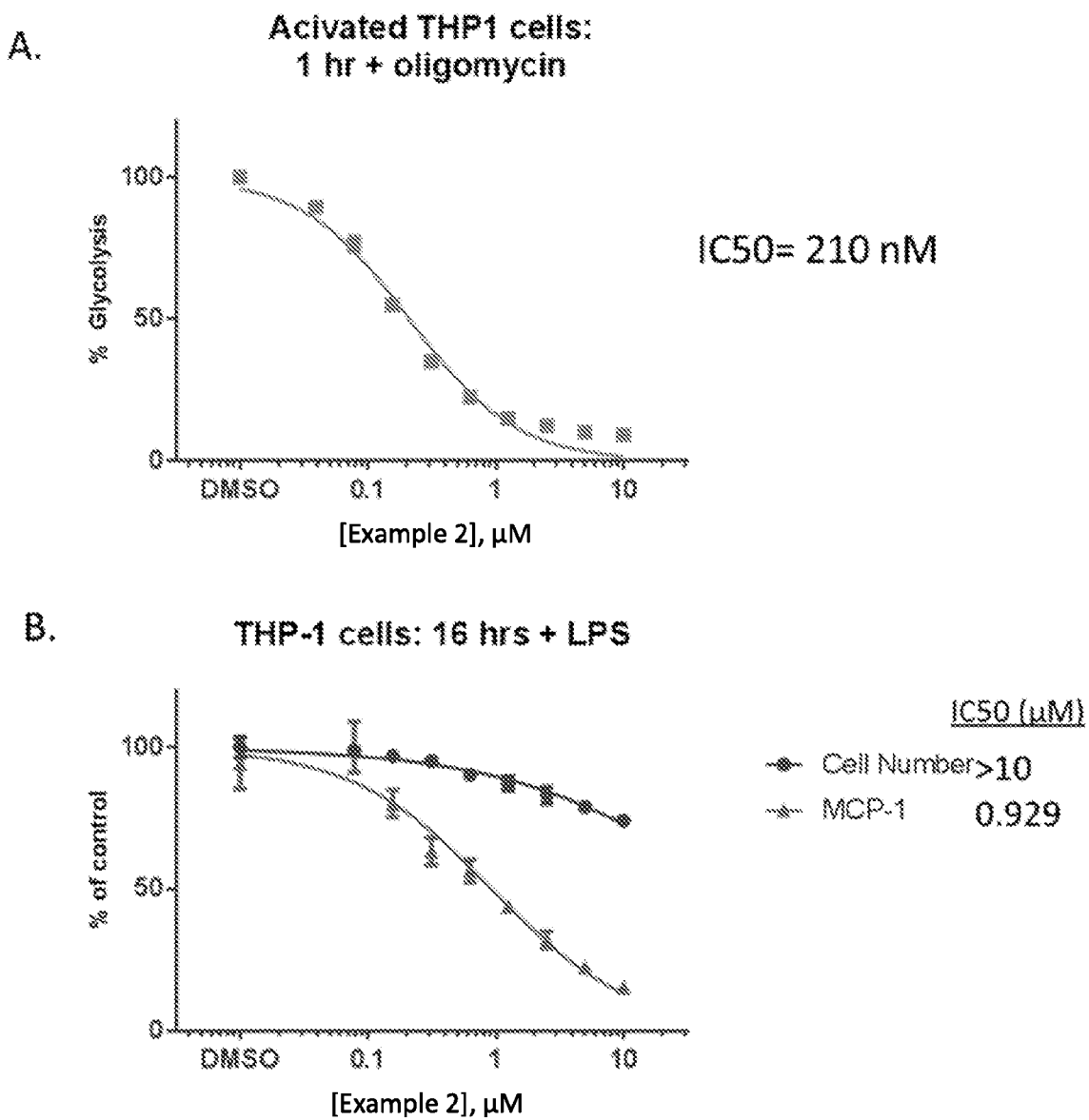
FIG. 5 shows that the metabolism and function of THP1 monocytes are inhibited by Example 2.

Because other pro-inflammatory immune cells rely on enhanced glycolysis (including but not limited to innate immune cells such as monocytes, macrophages and dendritic cells), we assessed the ability of the compounds disclosed herein to inhibit glycolysis and function of THP1 monocytes. In FIG. 5, Example 2 is shown to inhibit glycolysis in LPS stimulated THP1 monocytes. In addition, Example 2 inhibits cytokine/chemokine secretion of select cytokines/chemokines, exemplified here by MCP-1.

Example 61 (Innate Immune Cells)

Figure 6:
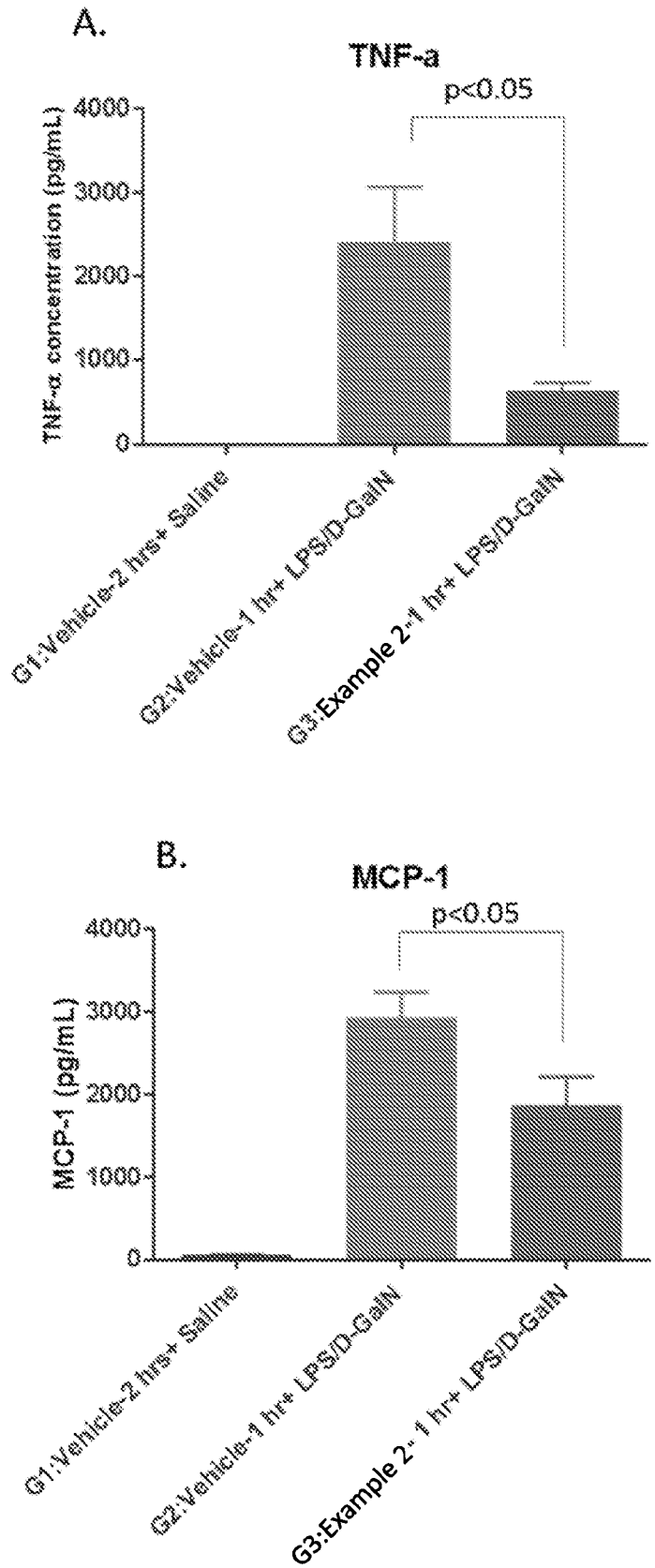
FIG. 6 shows that Example 2 (100 mg/kg p.o.) inhibits the increase of TNFalpha (FIG. 6A) and MCP-1 (FIG. 6B) one hour following LPS/Galn treatment of mice. 100 μg LPS and 18 mg D-galactosamine were used to induce cytokine production. Shown is the one hour time-point, however, Example 2 was unable to prevent a statistically significant increase of MCP-1 levels at 2 hours post LPS/Galn (not shown).

As described above, the glucose uptake inhibitors disclosed herein possess anti-inflammatory properties and inhibit metabolism, effector function and proliferation of activated monocytes. In FIG. 6, Example 2 is shown to modulate cytokine/chemokine production in response to LPS/D-galactosamine (mouse model of sepsis and liver damage). Example 2 prevents the dramatic increase of TNFalpha (FIG. 6A), a cytokine well-established as a major driver of inflammation. In line with in vitro results, Example 2 abrogates an initial increase in MCP-1 (FIG. 6B), but is unable to statistically suppress MCP1 induction at later time points (not shown).

Example 62—Methods

Determination of glucose uptake/GLUT activity (glycolysis assay): HT1080 cells, DLD1 cells (WT and GLUT1−/−) and human CD4+ T cells were plated in 96-well plates. Cells were exposed to the combination of 10 μM Oligomycin (to block mitochondrial-derived ATP) and the glucose uptake inhibitors disclosed herein for one-hour, after which glycolytically-derived ATP was measured with the Cell Titer-Glo assay kit (Promega). Dose-response curves of the glucose uptake inhibitors disclosed herein were used to determine the $IC_{50}$ for GLUT activity.

T cell assays: Human CD4 T cells were purified using RossetteSep Human CD4 T cell Enrichment Cocktail. Resting T cells were activated with 5 μg/ml plate-bound anti-CD3 and anti-CD28, −/+50 ng/ml IL-1β and 5 ng/ml TGF-β. The previously described glycolysis assay was performed 24 hours post-activation. IL-17 levels were measured by ELISA (R&D systems, Human IL-17 Quantikine ELISA kit). Proliferation was measured by Cell Titer Glo (Promega). Intracellular staining was performed and analyzed using the Guava EasyCyte flow cytometer. Antibodies were purchased from eBiosciences. Protein levels and phosphorylation status were assessed by western blot analysis using antibodies purchased from Cell Signaling.

Mouse Prophylactic MOG-EAE Model: Performed at Hooke laboratories.

THP1 Monocyte assay: THP1 monocytic cancer cells were activated with 1 ug/ml LPS (Sigma-Aldrich). The previously described glycolysis assay was performed 16 hrs post-activation. For cytokine secretion, cells were pre-treated for one hour with GLUT inhibitors prior to 16 hours of 1 μg/ml LPS treatment.

LPS Mouse Model: Performed at Pharmalegacy.

| Example No. | GLUT IC50 (nM) HT1080 cells | GLUT1 IC50 (nM) DLD1-WT cells | GLUT3 IC50 (nM) DLD1-KO cells |
|---|---|---|---|
| Ex. 1 | 242 | 52 | 128.9 |
| Ex. 2 | 149 | 115 | 60.9 |
| Ex. 3 | 44 | 59.63 | 33.64 |
| Ex. 4 | 50 | 86 | 148.4 |
| Ex. 5 | 92 | 81 | 104.4 |
| Ex. 6 | 141 | 94 | 120.2 |
| Ex. 7 | 128 | 98 | 232.9 |
| Ex. 8 | 173 | 260.8 | 97.6 |
| Ex. 9 | 367 | 529 | 76.13 |
| Ex. 10 | 58.9 | 40.51 | 109.9 |
| Ex. 11 | 1352 | 3480 | 325 |
| Ex. 12 | 248 | 598 | 165.8 |
| Ex. 13 | 54 | 86.87 | 38.91 |
| Ex. 14 | 189 | 47 | 133.8 |
| Ex. 15 | 183 | 352.2 | 86.56 |
| Ex. 16 | 536 | 1015 | 126.7 |
| Ex. 17 | 166 | 334.1 | 92.16 |
| Ex. 18 | 89 | 99.5 | 43.95 |
| Ex. 19 | 169 | 257 | 66.09 |
| Ex. 20 | 423 | 709.2 | 177.1 |
| Ex. 21 | 408 | 786.1 | 248.2 |
| Ex. 22 | 112 | 104.9 | 66.83 |
| Ex. 23 | 258 | 462.8 | 110.3 |
| Ex. 24 | 454 | 801.1 | 85.97 |
| Ex. 25 | 433 | 1074 | 68.4 |
| Ex. 27 | 310.1 | 252.1 | 115.7 |
| Ex. 28 | 545.3 | 496.3 | 104.6 |
| Ex. 29 | 123.4 | 123.6 | 141.6 |
| Ex. 30 | 425 | 624.3 | 195.4 |
| Ex. 31 | 53.51 | 62.1 | 59.21 |
| Ex. 32 | 188.4 | 177.9 | 304.9 |
| Ex. 33 | 424.3 | 802.2 | 183.2 |
| Ex. 34 | 418.1 | 797.3 | 196.9 |
| Ex. 35 | 133.7 | 129.7 | 94.15 |
| Ex. 36 | 136.8 | 115.7 | 130.2 |
| Ex. 37 | 127.9 | 89.3 | 158.4 |
| Ex. 38 | 60.77 | 65.72 | 51.47 |
| Ex. 39 | 34.11 | 40.63 | 34.25 |
| Ex. 40 | 98.04 | 159.7 | 68.32 |
| Ex. 41 | 106.6 | 48.82 | 191.3 |
| Ex. 42 | 31.19 | 30.73 | 41.58 |
| Ex. 43 | 45.97 | 34.37 | 58.87 |
| Ex. 44 | 122.8 | 91.22 | 158.6 |
| Ex. 45 | 25.05 | 25.18 | 40.63 |
| Ex. 46 | 37.08 | 34.84 | 87.02 |
| Ex. 47 | 111.1 | 94.92 | 133.2 |
| Ex. 48 | 81.53 | 71.62 | 109.7 |
| Ex. 49 | 30.72 | 30.26 | 50.9 |
| Ex. 50 | 44.68 | 38.53 | 72.08 |
| Ex. 51 | 112.6 | 105.9 | 125.3 |
| Ex. 52 | 92.08 | 81.61 | 117.7 |
| Ex. 53 | 282.9 | 222.4 | 271.1 |
| Ex. 54 | 196.2 | 146.1 | 290.2 |
| Ex. 55 | 190.5 | 192.3 | 238.2 |

The invention claimed is:

1. A compound having the structure:

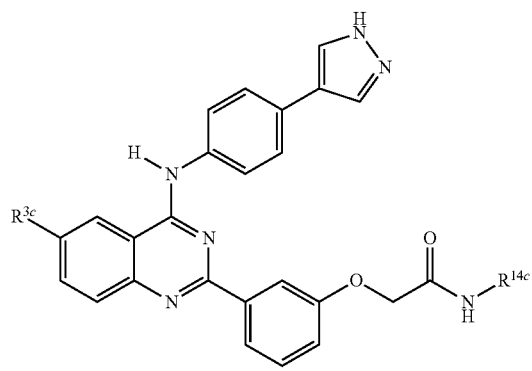

IIIc or a pharmaceutically acceptable salt thereof, wherein:
$R^{14c}$ is $C_4$-$C_6$ alkyl, which may be branched, straight chain or cyclic, and which is optionally substituted with 1 to 3 substituents selected from halo and hydroxy; and
$R^{3c}$ is selected from the group consisting of H and lower alkoxy, which may be unsubstitiued or substituted by halo or lower alkoxy.

2. The compound according to claim 1, having the structure:

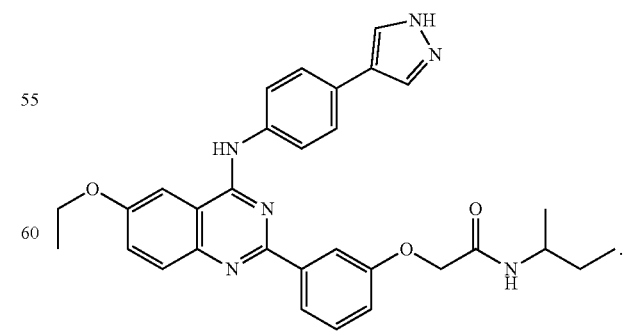

3. The compound according to claim 2, having the structure

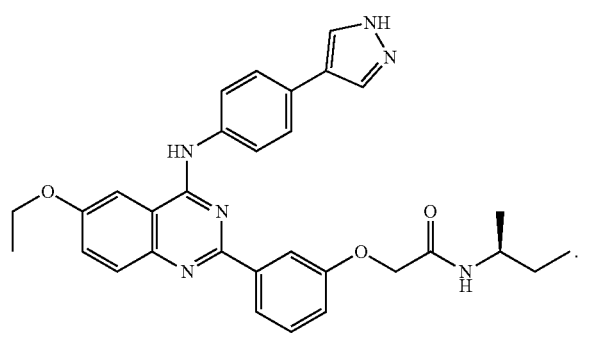

4. The compound according to claim 2, having the structure

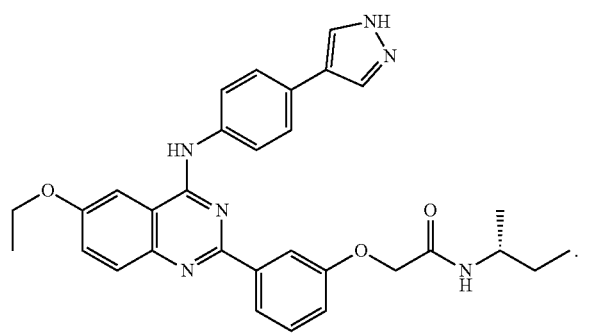 [SMILES: CCOc1ccc2nc(-c3cccc(OCC(=O)NC(C)CC)c3)nc(Nc3ccc(-c4cn[nH]c4)cc3)c2c1]

5. A method of treating an autoimmune disease or an inflammatory disease comprising administering to a patient in need thereof a therapeutically effective amount of a compound the formula I:

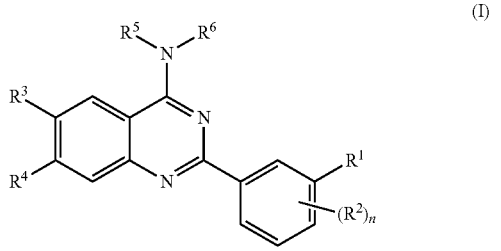

or a pharmaceutically acceptable salt thereof, wherein:
$R^1$ is selected from the group consisting of aryl, —$(CH_2)_y$—$NR^{13}R^{14}$, —X—$R^{12}$, —$(CH_2)_y$—C(=O)$NR^{13}R^{14}$, —O—$(CH_2)_y$—$CO_2R^{12}$, —O—$(CH_2)_y$—C(=O)$NR^{13}R^{14}$, —O—$(CH_2)_y$-cycloalkyl, —$(CH_2)_y$—O—C(=O)—$NR^{13}R^{14}$, —NH—C(=O)—$(CH_2)_y$—$NR^{13}R^{14}$, —NH—C(=O)—X—$R^{15}$, —$(CH_2)_y$—S(=O)$_2NR^{13}R^{14}$, —O—$(CH_2)_y$—S(=O)$_2NR^{13}R^{14}$, —NH—S(=O)$_2$—X—$R^{15}$, —NH—$(CH_2)_y$—$NR^{13}R^{14}$, —O—$(CH_2)_y$-heteroaryl, —O—C(=O)—$(CH_2)_y$—$NR^{13}R^{14}$, and —O—$(CH_2)_z$—$NR^{13}R^{14}$;
$R^{12}$ is selected from the group consisting of $C_1$-$C_{10}$ alkyl, —($C_1$-$C_6$ alkyl)-O—($C_1$-$C_6$ alkyl), —($C_1$-$C_6$ alkyl)-C(=O)$NR^{16}R^{17}$, —($C_1$-$C_6$ alkyl)-O—($C_1$-$C_6$ alkyl)-O—($C_1$-$C_6$ alkyl), —($C_1$-$C_6$ alkyl)-$NR^{16}R^{17}$, aryl, —($C_1$-$C_6$ alkyl)-O-(aryl), aralkyl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkyl, $C_1$-$C_6$ alkoxy, hydroxy, cyano, and $C_1$-$C_3$ perfluoro alkyl;
$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-C(=O)$NR^{16}R^{17}$, —($C_1$-$C_6$ alkyl)-$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, —$SO_2$-alkyl, hydroxy, amino, cyano and $C_1$-$C_3$ perfluoro alkyl;
or $R^{13}$ and $R^{14}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, —$SO_2$-alkyl, oxo, hydroxy, cyano and $C_1$-$C_3$ perfluoro alkyl;
X is selected from a covalent bond, O, and $C_1$-$C_6$ alkyl;
$R^{15}$ is selected from the group consisting of H, $C_1$-$C_8$ alkyl, aryl, heteroaryl, $C_3$-$C_7$ cycloalkyl, —($C_1$-$C_6$ alkyl)-O—($C_1$-$C_6$ alkyl), —($C_1$-$C_6$ alkyl)-O-(aryl), —($C_1$-$C_6$ alkyl)-C(=O)$NR^{16}R^{17}$, —O—$(CH_2)_x$—$CO_2R^{18}$, —O—$(CH_2)_x$—C(=O)$NR^{16}R^{17}$, —($C_1$-$C_6$ alkyl)-$CO_2R^{18}$, and a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, cyano and $C_1$-$C_3$ perfluoro alkyl;
$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, cyano and $C_1$-$C_3$ perfluoro alkyl;
or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, cyano and $C_1$-$C_3$ perfluoro alkyl;
$R^{18}$ is selected from the group consisting of aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, cyano and $C_1$-$C_3$ perfluoroalkyl;
x is selected from 1 to 6;
y is selected from 0 to 6;
z is selected from 2 to 6;
each $R^2$ is independently selected from the group consisting of lower alkyl, CN, halo, hydroxy, lower alkoxy, amino, and perfluoro lower alkyl;
n is selected from 0 to 4;
$R^3$ is selected from the group consisting of H, lower alkyl, CN, halo, hydroxy, lower alkoxy, amino, perfluoro lower alkyl, —$(CH_2)_a$—$NR^{33}R^{34}$, —Y—$R^{32}$, —O—

$(CH_2)_a$—$CO_2R^{32}$, —O—$(CH_2)_a$—C(=O)$NR^{33}R^{34}$, —O—$(CH_2)_a$-heteroaryl, —O—$(CH_2)_a$-cycloalkyl, —O—C(=O)—$(CH_2)_a$—$NR^{33}R^{34}$, —O—$(CH_2)_c$—$NR^{33}R^{34}$, —NH—C(=O)—$(CH_2)_a$—$NR^{33}R^{34}$, —NH—C(=O)—Y—$R^{35}$, —NH—C(=O)—$(CH_2)_a$—$NR^{33}R^{34}$;

$R^{32}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{36}R^{37}$, —($C_1$-$C_6$ alkyl)-C(=O)$NR^{36}R^{37}$, —($C_1$-$C_6$ alkyl)-O—($C_1$-$C_6$ alkyl)-O—($C_1$-$C_6$ alkyl), each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{33}$ and $R^{34}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{36}R^{37}$, —($C_1$-$C_6$ alkyl)-C(=O)$NR^{36}R^{37}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{33}$ and $R^{34}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

Y is selected from a covalent bond, O, NH, and $C_1$-$C_6$ alkyl;

$R^{35}$ is selected from the group consisting of H, aryl, —($C_1$-$C_6$ alkyl)-O—($C_1$-$C_6$ alkyl), —($C_1$-$C_6$ alkyl)-$NR^{36}R^{37}$, —$CO_2R^{38}$, —O—$(CH_2)_b$—$CO_2R^{38}$, and —C(=O)$NR^{36}R^{37}$, $R^{36}$ and $R^{37}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{36}$ and $R^{37}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{38}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{36}R^{37}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

$R^4$ is selected from the group consisting of H, lower alkyl, CN, halo, hydroxy, lower alkoxy, amino, perfluoro lower alkyl, —$(CH_2)_a$—$NR^{43}R^{44}$, —Z—$R^{42}$, —O—$(CH_2)_a$—$CO_2R^{42}$, —O—$(CH_2)_a$—C(=O)$NR^{43}R^{44}$, —O—$(CH_2)_a$-heteroaryl, —O—$(CH_2)_a$-cycloalkyl, —O—C(=O)—$(CH_2)_a$—$NR^{43}R^{44}$, —O—$(CH_2)_c$—$NR^{43}R^{44}$, —NH—C(=O)—$(CH_2)_a$—$NR^{43}R^{44}$, —NH—C(=O)—Z—$R^{45}$, —NH—C(=O)—$(CH_2)_a$—$NR^{43}R^{44}$;

$R^{42}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-C(=O)$NR^{46}R^{47}$, —($C_1$-$C_6$ alkyl)-O—($C_1$-$C_6$ alkyl)-O—($C_1$-$C_6$ alkyl), each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{43}$ and $R^{44}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-C(=O)$NR^{46}R^{47}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{43}$ and $R^{44}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

Z is selected from a covalent bond, O, NH, and $C_1$-$C_6$ alkyl;

$R^{45}$ is selected from the group consisting of H, aryl, —($C_1$-$C_6$ alkyl)-O—($C_1$-$C_6$ alkyl), —($C_1$-$C_6$ alkyl)-$NR^{46}R^{47}$, —$CO_2R^{48}$, —O—$(CH_2)_b$—$CO_2R^{48}$, and —C(=O)$NR^{46}R^{47}$;

$R^{46}$ and $R^{47}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{46}$ and $R^{47}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{48}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

each a is independently selected from 0 to 6;

each b is independently selected from 0 to 6;

each c is independently selected from 2 to 6;

$R^5$ is selected from the group consisting of H and $C_1$-$C_6$ alkyl;

$R^6$ is selected from the group of formula (IA) and (IB):

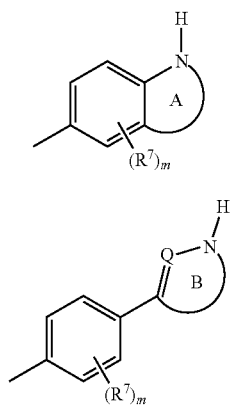

wherein

Ring A is a 5- or 6-membered ring which may comprise 0-2 additional ring heteroatoms selected from N, O and S, and may be unsubstituted or may be substituted with 1 to 3 substituents selected from halo, CN, oxo, hydroxy, amino, lower alkyl, perfluoro lower alkyl, and lower alkoxy;

Ring B is a 5- or 6-membered ring which may comprise 0-2 additional ring heteroatoms selected from N, O and S, and may be unsubstituted or may be substituted with 1 to 3 substituents selected from halo, CN, oxo, hydroxy, amino, lower alkyl, perfluoro lower alkyl, and lower alkoxy;

$R^7$ is selected from the group consisting of halo, CN, oxo, hydroxy, amino, lower alkyl, perfluoro lower alkyl, and lower alkoxy; and m is 0 to 2.

6. The method according to claim 5, wherein the disease is an autoimmune disease.

7. The method according to claim 6, wherein the autoimmune disease is selected from the group consisting of rheumatoid arthritis, multiple sclerosis, systemic lupus erythematosus (SLE; lupus), psoriasis, Crohn's disease, ulcerative colitis, atopic dermatitis, eczema, and graft-versus-host disease (GVHD).

8. The method according to claim 5, wherein the disease is an inflammatory disease.

9. The method according to claim 8, wherein the inflammatory disease is selected from the group consisting of asthma, cardiovascular inflammation, renal inflammation, arteriosclerosis and sepsis.

10. The method according to claim 8, wherein the inflammatory disease is a fibrotic condition.

11. The method according to claim 10, wherein the fibrotic condition is selected from the group consisting of idiopathic pulmonary fibrosis, NASH, scleroderma, systemic sclerosis, and cirrhosis.

12. The method according to claim 5, wherein the group of formula IA is selected from:

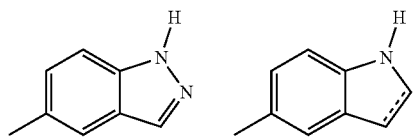

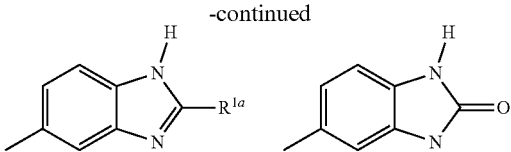

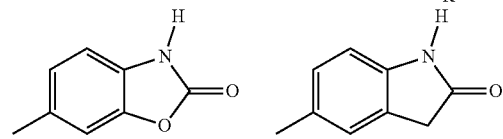

wherein the dotted line represents an optional double bond; $R^{1a}$ is selected from the group consisting of H, lower alkyl, and perfluoro lower alkyl; and $R^{2a}$ is selected from the group consisting of H and lower alkyl.

13. The method according to claim 5, wherein formula IB is selected from:

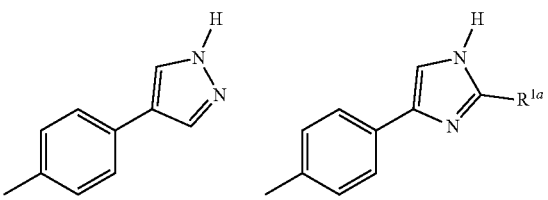

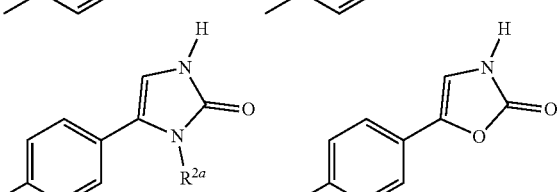

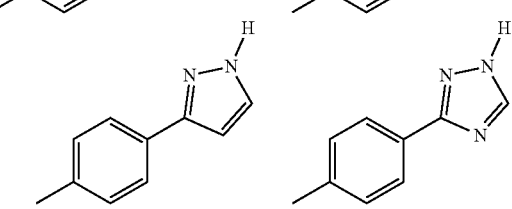

wherein $R^{1a}$ is selected from the group consisting of H, lower alkyl, and perfluoro lower alkyl;

and $R^{2a}$ is selected from the group consisting of H and lower alkyl.

14. The method according to claim 5, comprising administering a compound of the formula II:

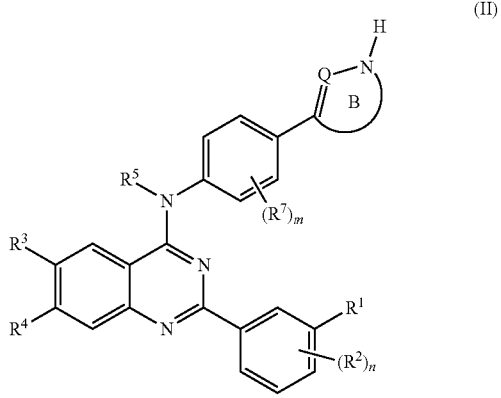

or a pharmaceutically acceptable salt thereof, wherein R$^1$, R$^2$, R$^3$, R$^4$, R$^5$, R$^7$, Ring B, n and m are as stated above for formula I.

15. The method according to claim 5, comprising administering a compound of the formula III:

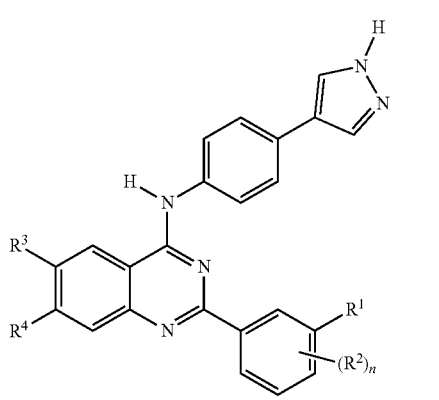

(III)

or a pharmaceutically acceptable salt thereof, wherein R$^1$, R$^2$, R$^3$, R$^4$, n and m are as stated above for formula I.

16. The method according to claim 5, comprising administering a compound of the formula IV:

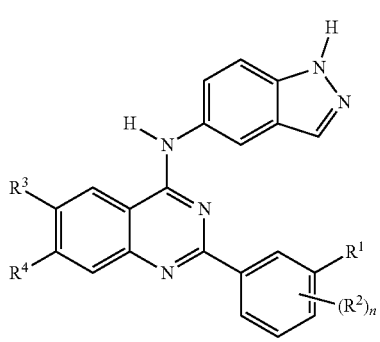

(IV)

or a pharmaceutically acceptable salt thereof, wherein R$^1$, R$^2$, R$^3$, R$^4$, n and m are as stated above for formula I.

17. The method according to claim 5, comprising administering a compound of the formula V:

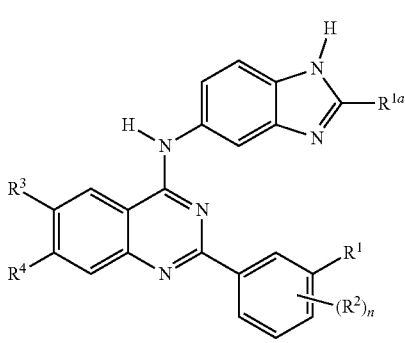

(V)

or a pharmaceutically acceptable salt thereof, wherein R$^{1a}$ is selected from the group consisting of H, lower alkyl, and perfluoro lower alkyl; and R$^1$, R$^2$, R$^3$, R$^4$, n and m are as stated above for formula I.

18. The method according to claim 5, comprising administering a compound of the formula IIIa:

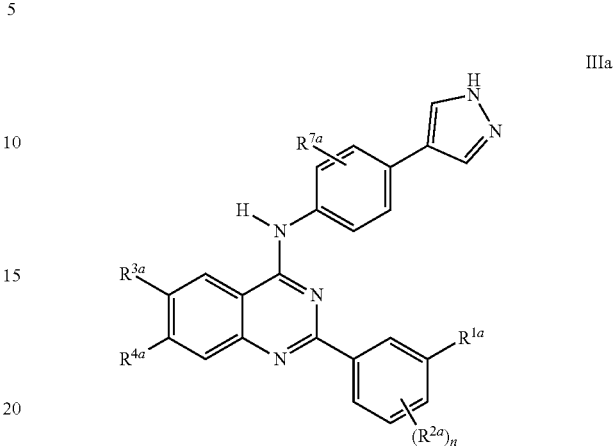

IIIa or a pharmaceutically acceptable salt thereof, wherein:

R$^{1a}$ is selected from the group consisting of O—(CH$_2$)$_y$—C(=O)—NR$^{13a}$R$^{14a}$ and —NH—C(=O)—(CH$_2$)$_y$—NR$^{13a}$R$^{14a}$;

R$^{13a}$ and R$^{14a}$ are independently selected from the group consisting of H, C$_1$-C$_8$ alkyl, C$_2$-C$_8$ alkenyl, C$_2$-C$_8$ alkynyl, —(C$_1$-C$_6$ alkyl)-O—(C$_1$-C$_6$ alkyl), each of which may be optionally substituted by from 1 to 3 substituents independently selected from halo, hydroxy, amino, cyano and C$_1$-C$_3$ perfluoro alkyl;

alternatively, R$^{13a}$ and R$^{14a}$ may be taken together to form a three to six membered heterocyclic ring having 1 to 3 heteroatoms, and which is optionally substituted by from 1 to 3 substituents independently selected from halo, C$_1$-C$_6$ alkyl, C$_2$-C$_6$ alkenyl, C$_1$-C$_6$ alkoxy, —SO$_2$-alkyl, oxo, hydroxy, cyano and C$_1$-C$_3$ perfluoro alkyl;

y is 0 to 6;

R$^{2a}$ is selected from the group consisting of H, lower alkyl, halo, lower alkoxyl, hydroxy, and perfluoro lower alkyl;

R$^{3a}$ is selected from the group consisting of H, lower alkyl, halo, hydroxy, lower alkoxy, amino, and perfluoro lower alkyl, and wherein the lower alkyl or lower alkoxy may be optionally substituted with halo or lower alkoxy;

R$^{4a}$ is selected from the group consisting of H, lower alkyl, halo, hydroxy, lower alkoxy, amino, and perfluoro lower alkyl, and wherein the lower alkyl or lower alkoxy may be optionally substituted with halo or lower alkoxy; and R$^{7a}$ is selected from the group consisting of H and halo.

19. The method according to claim 18, wherein y is 1 to 3.

20. The method according to claim 19, wherein R$^{13a}$ and R$^{14a}$ are independently selected from the group consisting of H and C$_1$-C$_8$ alkyl.

21. The method according to claim 20, wherein R$^{14a}$ is C$_1$ to C$_6$ alkyl.

22. The method according to claim 20, wherein R$^{14a}$ is C$_4$ to C$_8$ alkyl.

23. The method according to claim 20, wherein R$^{14a}$ is C$_4$ to C$_6$ alkyl.

24. The method according to claim 20, wherein $R^{14a}$ is H.

25. The method according to claim 18, wherein $R^{2'}$ is selected from the group consisting of H and halo.

26. The method according to claim 18, wherein $R^{3a}$ is selected from the group consisting of H and lower alkoxy.

27. The method according to claim 18, wherein $R^{4a}$ is H.

28. The method according to claim 5, comprising administering a compound of the IIIb:

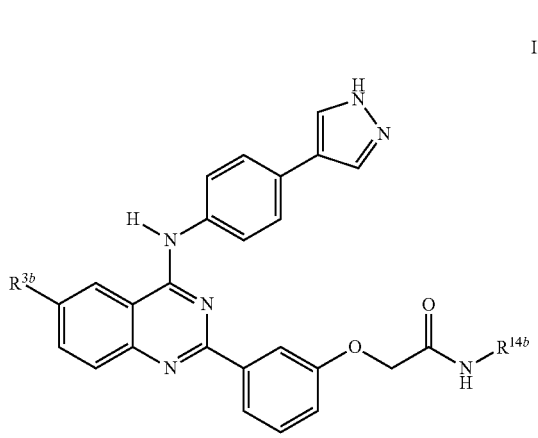

IIIb or a pharmaceutically acceptable salt thereof, wherein:
$R^{14b}$ is $C_1$-$C_6$ alkyl, which may be branched, straight chain or cyclic, and which is optionally substituted with 1 to 3 substituents selected from halo and hydroxy; and
$R^{3b}$ is selected from the group consisting of H and lower alkoxy, wherein the lower alkoxy may be optionally substituted with halo or lower alkoxy.

29. The method according to claim 28, wherein the optional substituents, if present on $R^{14b}$ are halo, and most preferably are F.

30. The method according to claim 28, wherein $R^{14b}$ is $C_4$-$C_6$ alkyl, which may be branched, straight chain or cyclic, and which is optionally substituted with 1 to 3 substituents selected from halo and hydroxy.

31. The method according to claim 28, wherein $R^{3b}$ is lower alkoxy.

32. The method according to claim 5, comprising administering a compound of the formula IIIc:

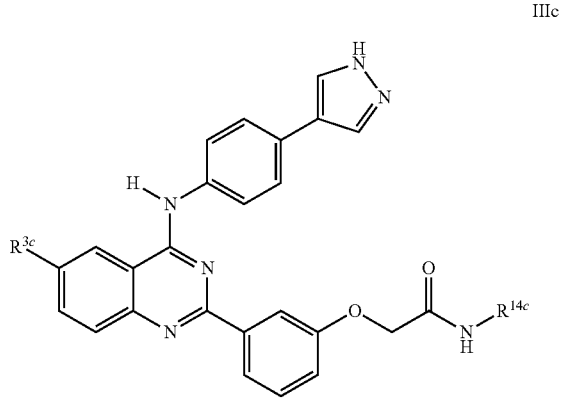

IIIc or a pharmaceutically acceptable salt thereof, wherein:
$R^{14c}$ is $C_4$-$C_6$ alkyl, which may be branched, straight chain or cyclic, and which is optionally substituted with 1 to 3 substituents selected from halo and hydroxy; and
$R^{3c}$ is selected from the group consisting of H and lower alkoxy, which may be unsubstitiued or substituted by halo or lower alkoxy.

33. The method according to claim 5, comprising administering a compound of the formula IIId:

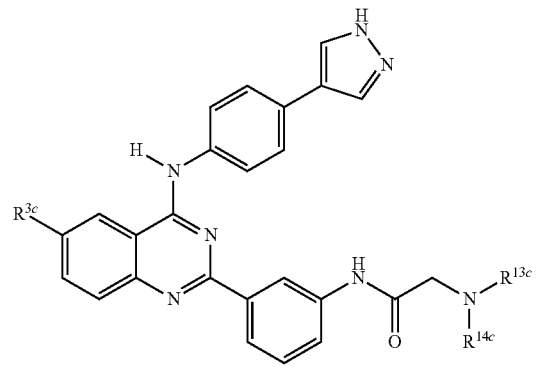

IIId or a pharmaceutically acceptable salt thereof, wherein:
$R^{13c}$ and $R^{14c}$ are independently selected from the group consisting of H and $C_1$-$C_6$ alkyl, which may be branched, straight chain or cyclic, and which is optionally substituted with 1 to 3 substituents selected from halo and hydroxy;
alternatively, $R^{13c}$ and $R^{14c}$ may be taken together to form a five or six membered heterocyclic ring having 1 to 3 heteroatoms, and which is optionally substituted by from 1 to 3 substituents independently selected from halo, $C_1$-$C_3$ alkyl, $C_1$-$C_3$ alkoxy, oxo, and hydroxy; and
$R^{3c}$ is selected from the group consisting of H and lower alkoxy, wherein lower alkoxy may be optionally substituted with halo or lower alkoxy.

34. The method according to claim 33, wherein $R^{13c}$ and $R^{14c}$ are be taken together form a morpholine group.

35. The method according to claim 5, comprising administering a compound selected from the group consisting of:
2-(3-(4-((4-(1H-pyrazol-4-yl)phenyl)amino)-6-ethoxyquinazolin-2-yl)phenoxy)-N-cyclopropylacetamide;
2-(3-(4-((4-(1H-pyrazol-4-yl)phenyl)amino)-6-ethoxyquinazolin-2-yl)phenoxy)-N-isopropylacetamide;
2-(3-(4-((4-(1H-pyrazol-4-yl)phenyl)amino)-6-ethoxyquinazolin-2-yl)phenoxy)-N-(tert-butyl)acetamide;
2-(3-(4-((4-(1H-pyrazol-4-yl)phenyl)amino)-6-ethoxyquinazolin-2-yl)phenoxy)-N-(tert-pentyl)acetamide;
2-(3-(4-((4-(1H-pyrazol-4-yl)phenyl)amino)-6-ethoxyquinazolin-2-yl)phenoxy)-N-cyclopentylacetamide;
2-(3-(4-((4-(1H-pyrazol-4-yl)phenyl)amino)-6-ethoxyquinazolin-2-yl)phenoxy)-N-cyclobutylacetamide;
2-(3-(4-((4-(1H-pyrazol-4-yl)phenyl)amino)-6-ethoxyquinazolin-2-yl)phenoxy)-N-(pentan-3-yl)acetamide;
2-(3-(4-((4-(1H-pyrazol-4-yl)phenyl)amino)-6-methoxyquinazolin-2-yl)phenoxy)-N-isopropylacetamide;
2-(3-(4-((4-(1H-pyrazol-4-yl)phenyl)amino)-6-methoxyquinazolin-2-yl)phenoxy)-N-cyclopropylacetamide;
2-(3-(4-((4-(1H-pyrazol-4-yl)phenyl)amino)-6-methoxyquinazolin-2-yl)phenoxy)-N-cyclopentylacetamide;
2-(3-(4-((4-(1H-pyrazol-4-yl)phenyl)amino)-6-methoxyquinazolin-2-yl)-5-fluorophenoxy)-N-isopropylacetamide;
2-(3-(4-((4-(1H-pyrazol-4-yl)phenyl)amino)-6-methoxyquinazolin-2-yl)phenoxy)-N-propylacetamide;

2-(3-(4-((4-(1H-pyrazol-4-yl)phenyl)amino)-6-methoxy-quinazolin-2-yl)phenoxy)-N-(tert-butyl)acetamide;
2-(3-(4-((4-(1H-pyrazol-4-yl)phenyl)amino)-6-methoxy-quinazolin-2-yl)phenoxy)-N-isobutylacetamide;
2-(3-(4-((4-(1H-pyrazol-4-yl)phenyl)amino)-6-methoxy-quinazolin-2-yl)phenoxy)-N-(3,3-difluorocyclobutyl)acetamide;
2-(3-(4-((4-(1H-pyrazol-4-yl)phenyl)amino)-6-ethoxy-quinazolin-2-yl)phenoxy)-N-propylacetamide;
2-(3-(4-((4-(1H-pyrazol-4-yl)phenyl)amino)-6-ethoxy-quinazolin-2-yl)phenoxy)-N-isobutylacetamide;
2-(3-(4-((4-(1H-pyrazol-4-yl)phenyl)amino)-6-ethoxy-quinazolin-2-yl)phenoxy)-N-(sec-butyl)acetamide;
2-(3-(4-((4-(1H-pyrazol-4-yl)phenyl)amino)-6-ethoxy-quinazolin-2-yl)phenoxy)-N-(3,3-difluorocyclobutyl)acetamide;
2-(3-(4-((2-fluoro-4-(1H-pyrazol-4-yl)phenyl)amino)-6-methoxyquinazolin-2-yl)phenoxy)-N-isopropylacetamide;
2-(3-(6-ethoxy-4-((2-fluoro-4-(1H-pyrazol-4-yl)phenyl)amino)quinazolin-2-yl)phenoxy)-N-isopropylacetamide;
2-(3-(4-((4-(1H-pyrazol-4-yl)phenyl)amino)-6-methoxy-quinazolin-2-yl)phenoxy)-N-(sec-butyl)acetamide;
2-(3-(4-((4-(1H-pyrazol-4-yl)phenyl)amino)-6-methoxy-quinazolin-2-yl)phenoxy)-N-(1,3-difluoropropan-2-yl)acetamide;
2-(3-(4-((4-(1H-pyrazol-4-yl)phenyl)amino)-6-ethoxy-quinazolin-2-yl)phenoxy)-N-(2,2,2-trifluoroethyl)acetamide;
2-(3-(4-((4-(1H-pyrazol-4-yl)phenyl)amino)-6-methoxy-quinazolin-2-yl)phenoxy)-N-(2,2,2-trifluoroethyl)acetamide;
N-(3-(4-((4-(1H-Pyrazol-4-yl)phenyl)amino)-6-methoxy-quinazolin-2-yl)phenyl)-2-morpholinoacetamide;
2-(3-(4-((4-(1H-Pyrazol-3-yl)phenyl)amino)-6-ethoxy-quinazolin-2-yl)phenoxy)-N-(tert-butyl)acetamide;
2-(3-(4-((4-(1H-Pyrazol-3-yl)phenyl)amino)-6-ethoxy-quinazolin-2-yl)phenoxy)-N-isopropylacetamide;
2-(3-(4-((4-(1H-Pyrazol-4-yl)phenyl)amino)-6-fluoroquinazolin-2-yl)phenoxy)-N-(tert-butyl)acetamide;
2-(3-(4-((4-(1H-Pyrazol-4-yl)phenyl)amino)-7-fluoroquinazolin-2-yl)phenoxy)-N-(tert-butyl)acetamide;
2-(3-(4-((4-(1H-Pyrazol-4-yl)phenyl)amino)-6-(2-methoxyethoxy)quinazolin-2-yl)phenoxy)-N-isopropylacetamide;
2-(3-(4-((4-(1H-Pyrazol-4-yl)phenyl)amino)-6-propoxy-quinazolin-2-yl)phenoxy)-N-isopropylacetamide;
2-(3-(4-((4-(1H-Pyrazol-4-yl)phenyl)amino)-6-fluoroquinazolin-2-yl)phenoxy)-N-isopropylacetamide;
2-(3-(4-((4-(1H-Pyrazol-4-yl)phenyl)amino)-7-fluoroquinazolin-2-yl)phenoxy)-N-isopropylacetamide;
(S)-2-(3-(4-((4-(1H-Pyrazol-4-yl)phenyl)amino)-6-ethoxyquinazolin-2-yl)phenoxy)-N-(sec-butyl)acetamide;
(R)-2-(3-(4-((4-(1H-Pyrazol-4-yl)phenyl)amino)-6-ethoxyquinazolin-2-yl)phenoxy)-N-(sec-butyl)acetamide;
2-(3-(4-((4-(1H-Pyrazol-4-yl)phenyl)amino)-6-propoxy-quinazolin-2-yl)phenoxy)-N-(tert-butyl)acetamide;
2-(3-(4-((4-(1H-Pyrazol-4-yl)phenyl)amino)-6-(2-fluoroethoxy)quinazolin-2-yl)phenoxy)-N-(tert-butyl)acetamide;
2-(3-(4-((4-(1H-Pyrazol-4-yl)phenyl)amino)-6-(2-methoxyethoxy)quinazolin-2-yl)phenoxy)-N-(tert-butyl)acetamide;
2-(3-(4-((4-(1H-Pyrazol-4-yl)phenyl)amino)-6-(2-fluoroethoxy)quinazolin-2-yl)phenoxy)-N-isopropylacetamide;
2-(3-(4-((4-(1H-Pyrazol-4-yl)phenyl)amino)-6-isopropoxyquinazolin-2-yl)phenoxy)-N-isopropylacetamide;
2-(3-(4-((4-(1H-Pyrazol-4-yl)phenyl)amino)-6-isopropoxyquinazolin-2-yl)phenoxy)-N-isopropylacetamide;
2-(3-(4-((4-(1H-Pyrazol-4-yl)phenyl)amino)-6-(2-methoxyethoxy)quinazolin-2-yl)phenoxy)-N-(sec-butyl)acetamide;
2-(3-(4-((4-(1H-Pyrazol-4-yl)phenyl)amino)-6-(2-fluoroethoxy)quinazolin-2-yl)phenoxy)-N-(sec-butyl)acetamide;
2-(3-(4-((4-(1H-Pyrazol-4-yl)phenyl)amino)-6-fluoroquinazolin-2-yl)phenoxy)-N-(sec-butyl)acetamide;
(S)-2-(3-(4-((4-(1H-pyrazol-4-yl)phenyl)amino)-6-(2-methoxyethoxy)quinazolin-2-yl)phenoxy)-N-(sec-butyl)acetamide;
(S)-2-(3-(4-((4-(1H-pyrazol-4-yl)phenyl)amino)-6-(2-fluoroethoxy)quinazolin-2-yl)phenoxy)-N-(sec-butyl)acetamide;
(S)-2-(3-(4-((4-(1H-pyrazol-4-yl)phenyl)amino)-6-fluoroquinazolin-2-yl)phenoxy)-N-(sec-butyl)acetamide;
(S)-2-(3-(4-((4-(1H-pyrazol-4-yl)phenyl)amino)-6-methoxyquinazolin-2-yl)phenoxy)-N-(sec-butyl)acetamide;
(R)-2-(3-(4-((4-(1H-pyrazol-4-yl)phenyl)amino)-6-(2-methoxyethoxy)quinazolin-2-yl)phenoxy)-N-(sec-butyl)acetamide;
(R)-2-(3-(4-((4-(1H-pyrazol-4-yl)phenyl)amino)-6-(2-fluoroethoxy)quinazolin-2-yl)phenoxy)-N-(sec-butyl)acetamide;
(R)-2-(3-(4-((4-(1H-pyrazol-4-yl)phenyl)amino)-6-fluoroquinazolin-2-yl)phenoxy)-N-(sec-butyl)acetamide;
(R)-2-(3-(4-((4-(1H-pyrazol-4-yl)phenyl)amino)-6-methoxyquinazolin-2-yl)phenoxy)-N-(sec-butyl)acetamide;
2-(3-(4-((4-(1H-pyrazol-4-yl)phenyl)amino)-7-fluoroquinazolin-2-yl)phenoxy)-N-(sec-butyl)acetamide;
(S)-2-(3-(4-((4-(1H-pyrazol-4-yl)phenyl)amino)-7-fluoroquinazolin-2-yl)phenoxy)-N-(sec-butyl)acetamide; and
(R)-2-(3-(4-((4-(1H-pyrazol-4-yl)phenyl)amino)-7-fluoroquinazolin-2-yl)phenoxy)-N-(sec-butyl)acetamide.

36. The method according to claim 5, comprising administering a compound selected from the group consisting of:
2-(3-(4-((4-(1H-pyrazol-4-yl)phenyl)amino)-6-ethoxy-quinazolin-2-yl)phenoxy)-N-isopropylacetamide;
2-(3-(4-((4-(1H-pyrazol-4-yl)phenyl)amino)-6-methoxy-quinazolin-2-yl)phenoxy)-N-cyclopentylacetamide;
2-(3-(4-((4-(1H-pyrazol-4-yl)phenyl)amino)-6-ethoxy-quinazolin-2-yl)phenoxy)-N-cyclopentylacetamide;
2-(3-(4-((4-(1H-pyrazol-4-yl)phenyl)amino)-6-ethoxy-quinazolin-2-yl)phenoxy)-N-(sec-butyl)acetamide;
2-(3-(4-((4-(1H-pyrazol-4-yl)phenyl)amino)-6-methoxy-quinazolin-2-yl)phenoxy)-N-(sec-butyl)acetamide;
2-(3-(4-((4-(1H-Pyrazol-3-yl)phenyl)amino)-6-ethoxy-quinazolin-2-yl)phenoxy)-N-(tert-butyl)acetamide;
2-(3-(4-((4-(1H-Pyrazol-3-yl)phenyl)amino)-6-ethoxy-quinazolin-2-yl)phenoxy)-N-isopropylacetamide;
2-(3-(4-((4-(1H-Pyrazol-4-yl)phenyl)amino)-6-fluoroquinazolin-2-yl)phenoxy)-N-(tert-butyl)acetamide;
2-(3-(4-((4-(1H-Pyrazol-4-yl)phenyl)amino)-6-(2-methoxyethoxy)quinazolin-2-yl)phenoxy)-N-isopropylacetamide;

(S)-2-(3-(4-((4-(1H-pyrazol-4-yl)phenyl)amino)-6-ethoxyquinazolin-2-yl)phenoxy)-N-(sec-butyl)acetamide;

(R)-2-(3-(4-((4-(1H-pyrazol-4-yl)phenyl)amino)-6-ethoxyquinazolin-2-yl)phenoxy)-N-(sec-butyl)acetamide;

2-(3-(4-((4-(1H-pyrazol-4-yl)phenyl)amino)-6-(2-fluoroethoxy)quinazolin-2-yl)phenoxy)-N-(tert-butyl)acetamide;

2-(3-(4-((4-(1H-pyrazol-4-yl)phenyl)amino)-6-(2-methoxyethoxy)quinazolin-2-yl)phenoxy)-N-(tert-butyl)acetamide;

2-(3-(4-((4-(1H-pyrazol-4-yl)phenyl)amino)-6-(2-fluoroethoxy)quinazolin-2-yl)phenoxy)-N-isopropylacetamide;

2-(3-(4-((4-(1H-pyrazol-4-yl)phenyl)amino)-6-isopropoxyquinazolin-2-yl)phenoxy)-N-isopropylacetamide;

2-(3-(4-((4-(1H-pyrazol-4-yl)phenyl)amino)-6-(2-methoxyethoxy)quinazolin-2-yl)phenoxy)-N-(sec-butyl)acetamide;

2-(3-(4-((4-(1H-pyrazol-4-yl)phenyl)amino)-6-fluoroquinazolin-2-yl)phenoxy)-N-(sec-butyl)acetamide;

(S)-2-(3-(4-((4-(1H-pyrazol-4-yl)phenyl)amino)-6-(2-methoxyethoxy)quinazolin-2-yl)phenoxy)-N-(sec-butyl)acetamide; and (R)-2-(3-(4-((4-(1H-pyrazol-4-yl)phenyl)amino)-6-(2-methoxyethoxy)quinazolin-2-yl)phenoxy)-N-(sec-butyl)acetamide.

* * * * *